US010472410B2

(12) United States Patent
Barelle et al.

(10) Patent No.: US 10,472,410 B2
(45) Date of Patent: Nov. 12, 2019

(54) ISOLATION OF THERAPEUTIC TARGET SPECIFIC VNAR DOMAINS TO ICOSL

(71) Applicant: THE UNIVERSITY COURT OF THE UNIVERSITY OF ABERDEEN, Aberdeen (GB)

(72) Inventors: Caroline Jane Barelle, Aberdeen (GB); William James Jonathan Finlay, Dublin (IE); Alfredo Darmanin-Sheehan, Dublin (IE)

(73) Assignee: THE UNIVERSITY COURT OF THE UNIVERSITY OF ABERDEEN, Aberdeen (GB)

( * ) Notice: Subject to any disclaimer, the term of this patent is extended or adjusted under 35 U.S.C. 154(b) by 696 days.

(21) Appl. No.: 14/785,975

(22) PCT Filed: Apr. 23, 2014

(86) PCT No.: PCT/EP2014/058276
§ 371 (c)(1),
(2) Date: Oct. 21, 2015

(87) PCT Pub. No.: WO2014/173975
PCT Pub. Date: Oct. 30, 2014

(65) Prior Publication Data
US 2016/0068600 A1 Mar. 10, 2016

Related U.S. Application Data

(60) Provisional application No. 61/815,043, filed on Apr. 23, 2013.

(51) Int. Cl.
C07K 16/00 (2006.01)
C07K 16/18 (2006.01)
C07K 16/28 (2006.01)
A61K 49/00 (2006.01)
G01N 33/68 (2006.01)
C07K 16/40 (2006.01)
C12N 15/10 (2006.01)
A61K 39/00 (2006.01)

(52) U.S. Cl.
CPC ........ C07K 16/005 (2013.01); A61K 49/0002 (2013.01); C07K 16/18 (2013.01); C07K 16/28 (2013.01); C07K 16/2803 (2013.01); C07K 16/2827 (2013.01); C07K 16/40 (2013.01); C12N 15/1037 (2013.01); G01N 33/6872 (2013.01); A61K 2039/505 (2013.01); C07K 2317/14 (2013.01); C07K 2317/20 (2013.01); C07K 2317/24 (2013.01); C07K 2317/565 (2013.01); C07K 2317/567 (2013.01); C07K 2317/569 (2013.01); C07K 2317/73 (2013.01); C07K 2317/76 (2013.01); C07K 2317/92 (2013.01); G01N 2333/70532 (2013.01)

(58) Field of Classification Search
None
See application file for complete search history.

(56) References Cited

U.S. PATENT DOCUMENTS

| 7,728,114 B2 * | 6/2010 | Mach ................. C07K 16/2809 |
| | | 530/388.15 |
| 7,977,071 B2 | 7/2011 | Nuttal et al. |
| 9,475,870 B2 | 10/2016 | Barelle et al. |
| 2011/0129473 A1 | 6/2011 | Taniagua-Solis |
| 2016/0176951 A1 | 6/2016 | Barelle et al. |

FOREIGN PATENT DOCUMENTS

| EP | 2281837 A2 | 8/2002 |
| EP | 2202243 A2 | 6/2010 |
| EP | 2277913 A2 | 1/2011 |
| EP | 2277914 A2 | 1/2011 |
| JP | 2009-501549 A | 1/2009 |
| WO | 03/014161 A2 | 2/2003 |
| WO | 2005/118629 A1 | 12/2005 |
| WO | 2006/003999 A1 | 1/2006 |
| WO | 2006122787 A2 | 11/2006 |
| WO | 2008028977 A2 | 9/2007 |
| WO | 2008043821 A1 | 4/2008 |
| WO | 2008096158 A2 | 8/2008 |
| WO | 2009/026638 A1 | 3/2009 |
| WO | 2011/056056 A2 | 5/2011 |
| WO | 2013/167883 A1 | 11/2013 |
| WO | 2014/173959 A1 | 10/2014 |

OTHER PUBLICATIONS

Robert W. Bahr, Deputy Commissioner for Patent Examination Policy Memorandum of Feb. 22, 2018, 2 pages. (Year: 2018).*
Edwards et al. (J. Mol. Biol. (2003) 334, 103-118). (Year: 2003).*
Harlow et al. (Antibodies, A Laboratory Manual, Cold Spring Harbor laboratory, 1988, pp. 37-47). (Year: 1988).*
Lloyd et al. (Protein Engineering, Design & Selection vol. 22 No. 3 pp. 159-168, 2009) (Year: 2009).*
Brown et al. (J Immunol. May 1, 1996;156(9):3285-91). (Year: 1996).*
Bedouelle et al. (FEBS J. Jan. 2006;273(1):34-46). (Year: 2006).*
Vajdos et al. (J Mol Biol. Jul. 5, 2002;320(2):415-28). (Year: 2002).*

(Continued)

Primary Examiner — Zachary S Skelding
(74) Attorney, Agent, or Firm — Arrigo, Lee, Guttman & Mouta-Bellum LLP

(57) ABSTRACT

The present invention provides ICOSL specific antigen binding molecules which are isolated from immunized and synthetic Elasmobranchii derived libraries. In particular, the present invention relates to shark Variable New Antigen Receptor (VNAR) domains that specifically bind and neutralize the activity of human Induced Co-Stimulatory Ligand (ICOSL). The neutralizing VNAR domains are isolated from two independent sources; an immunized nurse shark library and a synthetic spiny dogfish framework fusion library. The molecules may be formulated as pharmaceutical compositions and used in medicine.

Figure 1:
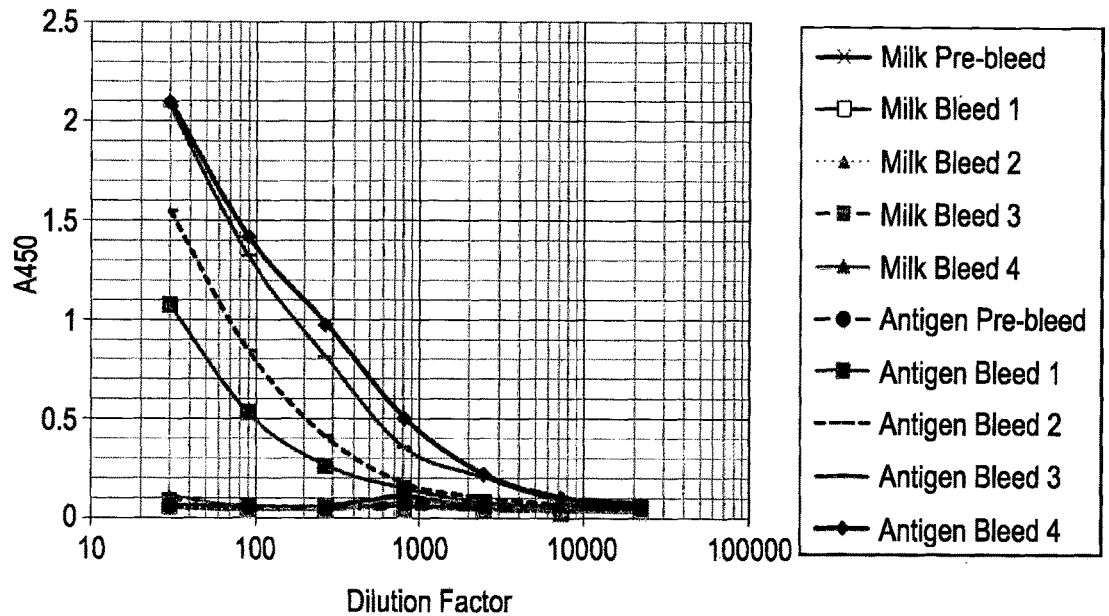

6 Claims, 24 Drawing Sheets
Specification includes a Sequence Listing.

(56) References Cited

OTHER PUBLICATIONS

Colman (Research in Immunology, 145:33-36, 1994) (Year: 1994).*
Rudikoff et al. (Proc. Natl. Acad. Sci. USA, 79: 1979-1983, Mar. 1982). (Year: 1982).*
Alt, Margitta, et. al., FEBS Letters, vol. 454, pp. 90-94 (1999).
Coppieters, Ken, et al., Arthritis & Rheumatism, vol. 54, No. 6, pp. 1856-1866 (2006).
Dennis, Mark S., et. al., The Journal of Biological Chemistry, vol. 277, No. 38, pp. 35035-35043 (2002).
Henderson et al., "Structure of an IgNAR-AMA1 Complex: Targeting a Conserved Hydrophobic Cleft Broadens Malarial Strain Recognition," Structure, vol. 15, pp. 1452-1466, (2007).
The International Search Report and Written Opinion for International Application No. PCT/GB2013/051183.
Stanfield, R.L. et al., Sciene, vol. 305, pp. 1770-1773 (2004).
Greenberg, Andrew S., Nature, vol. 374, pp. 168-173 (1995).
Holt, Lucy J., et al., Protein Engineering, Design & Selection, vol. 21, No. 5, pp. 283-288 (2008).
Wunder, Andreas, et. al., J Immunol., vol. 170, pp. 4793-4801 (2003).
Muller, Dafne, et. al., The Journal of Biological Chemistry, vol. 282, No. 17, pp. 12650-12660 (2007).
Muller, Mischa et al., mAbs, vol. 4, No. 6, pp. 673-685 (2012).
Nguyen, Allen, et al., Protein Engineering, Design & Selection. vol. 19, No. 7, pp. 291-297 (2006).
Wunder, Andreas, et. al., Int. J. Cancer, vol. 76, pp. 884-890 (1998).
Pedley, R.B., et al., Br. J. Cancer, vol. 70, pp. 1136-1131 (1994).
Smith, Bryan J., el. al., Bioconjugate Chem., vol. 12, pp. 750-756 (2001).
Stork, Roland, Protein Engineering, Design & Selection, vol. 20, No. 11, pp. 569-576 (2007).
Stork, Roland, The Journal of Biological Chemistry, vol. 283, No. 12,, pp. 7804-7812 (2008).
Atschul et al., J. Mol. Biol. (1990) 215, 403-410.
Aicher, A., et al., J. Immunol., 2000. 164(9): p. 4689-4696.
Barelle, C. J., et al., Adv. Ex. Med. Biol., 2009. 655: p. 49-62.
Bojalil, R., BMC Immunol., 2013: 14(7): p. 14-17.
Camacho-Villegas, T., mAbs., 2013. 5(1): p. 80-85.
Chattopadhyay, K., J. Immunol., 2006. 177(6): p. 3920-3929.
Devereux, et al., Nucleic acids Research, 12, 387 (1984).
Dooley, H. and Flajnik, M. F., Eur. J. Immunol., 2005. 35(3): p. 936-945.
Dooley, H., M.F. Flajnik, and A.J. Porter, Mol Immunol, 2003. 40(1): p. 25-33.
Enshell-Seijffers et al, Nucleic Acids Res. (2001); 29(10).
Faget, J., et al., Cancer Research, 2012. 72(23): p. 6130-6141.
Flajnik, M. F., and Dooley, H., Methods Mol. Biol. 2009. 562: p. 71-82.
Frey, O., et al., Ann. Rheum. Dis., 2010. 69(8): p. 1495-1501.
Gobert M, et al., Cancer Res., 2009. 69: p. 2000-2009.
Greenberg A. S., et al., Nature, 1995. 374(6518): p. 168-173.
Griffiths, K., et al., Antibodies, 2012. 2: p. 66-81.
Hu, Y., L., et al., J. Immunol., 2009. 182(3): p. 1421-1428.
Hufton et al, J Immunol Methods. (1999), 231, (1-2): 39-51.
Iwai, H., et al., J. Immunol, 2002. 169(8): p. 4332-4339.
Kovalenka, O. V., et al., J. Biol. Chem., 2012. 288(24): p. 17408-17419.
Larimore, K., et al., BMC Immunol., 2012. 13(29); p. 1-17.
Liu, J.L., et al., Mol Immunol., 2007. 44(7): p. 1775-8.
Liu, J.L., G.P. Anderson, and E.R. Goldman, BMC Biotechnol, 2007. 7: p. 78.
Ménétrier-Caux, C. et al., Targ. Oncol., 2012. 7: p. 15-28.
Müller, M.R., et al., mAbs, 2012. 4(6): p. 673-685.
Müller, M.R., et al., Methods Mol. Biol. 2012. 907: p. 177-194.
Nuttall, S. D., et al., Mol. Biol. 2001: 38: p. 313-326.
Nuttall, S.D., et al., FEBS Lett, 2002. 516(1-3): p. 80-6.
Pereboev et al J Virol. (2001); 75(15): 7107-13.
Rondot et al Nat Biotechnol. (2001); 19(1): 75-8.
Stanfield, R. L., et al Science, 2004. 305(5691): p. 1770-1773.
Stanfield, R. L., et al., J Mol. Biol., 2007. 367(2): p. 358-372).
Strauss L., et al., J Immunol., 2008. 180: p. 2967-2980.
Streltsov, V.A., et al, Protein Sci., 2005. 14(11): p. 2901-2909.
Usui, Y., et al., Eur J Immunol., 2006. 36(11): p. 3071-3081.
Walsh, R., Virology, 2011.411(1): p. 132-141.
Weiss et al, Protein Sci (2000) 9 (4): 647-54.
Wong et al, Gene, (1988) 68, pp. 193.
Yao, S., et al., Nature Reviews, 2013. 12: p. 130-146.
Yoshinaga,S., K., et al., Int. Immunol., 2000. 12(10): p. 1439-1447.
Shao et al Mol. Immunol., 44(4), 656-665 (2007).
Nuttall et al Eur. J. Biochem., 270(17), 3543-3554 (2003).
Nuttall et al Proteins, 55(1), 187-197 (2004).
Fennell et al J. Mol. Biol., 400(2), 155-170 (2010).
Mischa Roland Muller, et al., "Chapter 9: Generation and Isolation of Target-Specific Single-Domain Antibodies From Shark Immune Repertoires," Methods in Molecular Biology (2012) vol. 907, p. 177-194.
Stewart D. Nuttall, et al., "Isolation and Characterization of an IgNAR Variable Domain Specific for the Human Mitochondrial Translocase Receptor Tom 70," Eur.J.Biochem. (2003) vol. 270, No. 17, p. 3543-3554.
Stewart D. Nuttall, et al., "A naturally occurring NAR variable domain binds the Kgp protease from Porphyromonas gingivalis," FEBS letter. (2002) vol. 516, issues 1-3, pp. 80-86.
Notification of Reasons for Rejection, Japanese Application No. 2016-509455, dated Mar. 6, 2018.

* cited by examiner

| Source | Format | Clone | KD (nM) |
|---|---|---|---|
| Synthetic | Monomeric | 1A7 | 61.7 |
| | | 1A1 | 14.5 |
| | | 1A4 | 102.2 |
| | | 1C4 | 17.9 |
| | | 1G5 | 31.7 |
| | | 1H2 | 29.5 |
| | | 2V | - |
| | Fc | 1A1 | 9 |
| | | 1C4 | 47.6 |
| | | 1C8 | 18 |
| | | 1D12 | 1.8 |
| | | 2D4 | 116 |
| Immunized | | 1 | 3.8 |
| | | 8 | 1.2 |
| | | 2 | 3.1 |
| | | 13 | 11.1 |
| | | 17 | 8.4 |
| | | 11 | 1.7 |
| | | 12 | 4.5 |
| | | 2V | - |

Fig. 6B

|  | IC50 pM | |
| --- | --- | --- |
|  | Donor 450 | Donor 452 |
| hN-1C8-hFC | 11 | 7 |
| hN-1C4-hFC | 77 | 32 |
| hN-1G5-hFC | 52 | 95 |
| hN-1A1-hFC | 14 | 8 |
| hN-2D4-hFC | 8 | 9 |
| hN-1H2-hFC | 42 | 35 |
| hN-1D12-hFC | 140 | 215 |
| mab165 | 57 | 88 |

Fig. 8

Fig. 9A

| | |
|---|---|
| 1A9  | ASVNQTPRTATKETGESLTINCVLDTIN... TSWFRKNPGTTDWERMSIGGRYVESVNKGAKSFSLRIKDLTVADSATYICRA... YGAGTVLTVN |
| 1C8  | ASVNQTPRTATKETGESLTINCVLDT... TSWFRKNPGTTDWERMSIGGRYVESVNKGAKSFSLRIKDLTVADSATYYCKA... DGAGTVLTVN |
| 1D12 | TRVDQTPRTATKETGESLTINCVLDT... TSWFRKNPGTTDWERMSIGGRYVESVNKGAKSFSLRIKDLTVADSATYYCKA... DGAGTVLTVN |
| 2B6  | TRVDQTPRTATKETGESLTINCVLDT... TSWFRKNPGTTDWERMSIGGRYVESVNKGAKSFSLRIKDLTVADSATYICRA... YGAGTVLTVN |
| 2D3  | TRVDQTPRTATKETGESLTINCVLDT... TSWFRKNPGTTDWERMSIGGRYVESVNKGAKSFSLRIKDLTVADSATYYCKA... DGAGTVLTVN |
| 2D4  | TRVDQTPRTATKETGESLTINCVLDT... TSWFRKNPGTTDWERMSIGGRYVESVNKGAKSFSLRIKDLTVADSATYYCKA... DGAGTVLTVN |
| 2E8  | TRVDQTPRTATKETGESLTINCVLDT... TSWFRKNPGTTDWERMSIGGRYVESVNKGAKSFSLRIKDLTVADSATYYCKA... DGAGTVLTVN |
| 1G5  | ASVNQTPRTATKETGESLTINCVLDT... TSWFRKNPGTTDWERMSIGGRYVESVNKGAKSFSLRIKDLTVADSATYICRA... YGAGTVLTVN |
| 1H02 | TRVDQTPRTATKETGESLTINCVLDT... TSWFRKNPGTTDWERMSIGGRYVESVNKGAKSFSLRIKDLTVADSATYYCKA... DGAGTVLTVN |
| 1A1  | TRVDQTPRTATKETGESLTINCVLDT... TSWFRKNPGTTDWERMSIGGRYVESVNKGAKSFSLRIKDLTVADSATYICRA... YGAGTVLTVN |
| 1C04 | ASVNQTPRTATKETGESLTINCVLDT... TSWFRKNPGTTDWERMSIGGRYVESVNKGAKSFSLRIKDLTVADSATYYCKA... DGAGTVLTVN |
| 1A6  | TRVDQTPRTATKETGESLTINCVLDT... TSWFRKNPGTTDWERMSIGGRYVESVNKGAKSFSLRIKDLTVADSATYYCKA... DGAGTVLTVN |
| 1B2  | TRVDQTPRTATKETGESLTINCVVTGA... TWYRKNPGSSNQERISISGRYVESVNKRTMSFSLRIKDLTVADSATYYCKA... DGAGTVLTVN |
| 2C10 | ASVNQTPRTATKETGESLTINCVLDT... TSWFRKNPGTTDWERMSIGGRYVESVNKGAKSFSLRIKDLTVADSATYYCKA... DGAGTVLTVN |

Fig. 9A (continued)

| | |
|---|---|
| 2C7 | TRVDQTPRTATKETGESLIINCVTGAXXXXXSTYWYRKNPGSSNQERISISGRYVESVNKRTMSFSLRIKDLTVADSATYICRAGPPVESGGLDVYGAGTVLIVN |
| 3E8 | TRVDQTPRTATKETGESLIINCVLIDTXXXXXTSWFRKNPGTTDWERMSIGGRYVESVNKGAKSFSLRIKDLTVADSATYICRAXXXXXXXXYGAGTVLIVN |
| 3G11 | TRVDQTPRTATKETGESLIINCVLIDTXXXXXTSWFRKNPGTTDWERMSIGGRYVESVNKGAKSFSLRIKDLTVADSATYICRAXXXXXXXXYGAGTVLIVN |
| 4B5 | TRVDQTPRTATKETGESLIINCVLIDTXXXXXTSWFRKNPGTTDWERMSIGGRYVESVNKGAKSFSLRIKDLTVADSATYICRAXXXXXXXXYGAGTVLIVN |
| 4G1 | TRVDQTPRTATKETGESLIINCVLIDTXXXXXTSWFRKNPGTTDWERMSIGGRYVESVNKGAKSFSLRIKDLTVADSATYICRAXXXXXXXXYGAGTVLIVN |
| 5A12 | ASVNQTPRTATKETGESLIINCVLIDTXXXXXTSWFRKNPGTTDWERMSIGGRYVESVNKGAKSFSLRIKDLTVADSATYYCKAXXXXXXXXYDGAGTVLIVN |
| 5B10 | TRVDQTPRTATKETGESLIINCVLIDTXXXXXTSWFRKNPGTTDWERMSIGGRYVESVNKGAKSFSLRIKDLTVADSATYYCKAXXXXXXXXYDGAGTVLIVN |
| 5B9 | ASVNQTPRTATKETGESLIINCVLIDTXXXXXTSWFRKNPGTTDWERMSIGGRYVESVNKGAKSFSLRIKDLTVADSATYYCKAXXXXXXXXYDGAGTVLIVN |
| 5C1 | TRVDQTPRTATKETGESLIINCVLIDTXXXXXTSWFRKNPGTTDWERMSIGGRYVESVNKGAKSFSLRIKDLTVADSATYYCKAXXXXXXXXYDGAGTVLIVN |
| 5E6 | TRVDQTPRTATKETGESLIINCVLIDTXXXXXTSWFRKNPGTTDWERMSIGGRYVESVNKGAKSFSLRIKDLTVADSATYICRAXXXXXXXXYGAGTVLIVN |
| 5F3 | ASVNQTPRTATKETGESLIINCVLIDTXXXXXTSWFRKNPGTTDWERMSIGGRYVESVNKGAKSFSLRIKDLTVADSATYYCKAXXXXXXXXYDGAGTVLIVN |
| 5F6 | TRVDQTPRTATKETGESLIINCVLIDTXXXXXTSWFRKNPGTTDWERMSIGGRYVESVNKGAKSFSLRIKDLTVADSATYYCKAXXXXXXXXYDGAGTVLIVN |
| 5G1 | TRVDQTPRTATKETGESLIINCVLIDTXXXXXTSWFRKNPGTTDWERMSIGGRYVESVNKGAKSFSLRIKDLTVADSATYYCKAXXXXXXXXYDGAGTVLIVN |

1A9

GCAAGCGTTAATCAGACACCGCGTACCGCAACCAAAGAAACCGGTGAAAGCCTGACCATTAATTGTGTTCTGACCGATACCTGGAAATGGTGGCTGCAGACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCGGTCCGATCTACTTCGAAACTTGGCATGATGTTTATGGTGCAGGCACCGTTCTGACCGTTAAT

1C8

GCAAGCGTTAATCAGACACCGCGTACCGCAACCAAAGAAACCGGTGAAAGCCTGACCATTAATTGTGTTCTGACCGATACCCCGCAGAACTGGCAAGCTACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCAGTTTTCCTGAACCCGTGGGACTGGCCGCATTGGTATGATGGTGCAGGCACCGTTCTGACCGTTAAT

1D12

ACACGTGTTGATCAGACACCGCGTACCGCAACCAAAGAAACCGGTGAAAGCCTGACCATTAATTGTGTTCTGACCGATACCGGGTATGGTTTGGCTGCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCATGGTGGGACGTTCCGCAGCGTTGGGAACCGGTTTCTAACTACTGGTATGATGGTGCAGGCACCGTTCTGACCGTTAAT

2B6

ACACGTGTTGATCAGACACCGCGTACCGCAACCAAAGAAACCGGTGAAAGCCTGACCATTAATTGTGTTCTGACCGATACCTCTCCGACTGGTACTTTCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCCGTACTACCAGTACAACGACTGGCATGATGTTTATGGTGCAGGCACCGTTCTGACCGTTAAT

2D3

ACACGTGTTGATCAGACACCGCGTACCGCAACCAAAGAAACCGGTGAAAGCCTGACCATTAATTGTGTTCTGACCGATACCTGGACTACTTGGGTTGGTACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCACAGACTCCGTGGTGGATGCAGTGGCATCTGTCTATGTGGTATGATGGTGCAGGCACCGTTCTGACCGTTAAC

2D4

ACACGTGTTGATCAGACACCGCGTACCGCAACCAAAGAAACCGGTGAAAGCCTGACCATTAATTGTGTTCTGACCGATACCGATTATGGTTTGTTCTCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCATTCACTTGGCCGTGGGAATGGCCGGACCGTTGGTTCCGTCCGTGGTATGATGGTGCAGGCACCGTTCTGACCGTTAAT

Fig. 9B

2E8
ACACGTGTTGATCAGACACCGCGTACCGCAACCAAAGAAACCGGTGAAAGCCTGACCATTAATTGTGTTCTGACCGATACCAATTATGCTTGGTTCTCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCACTGTACCCGGGTTGGAAATGGCCGTGGCATAACTTCTGGTATGATGGTGCAGGCACCGTTCTGACCGTTAAT

1G5
GCAAGCGTTAATCAGACACCGCGTACCGCAACCAAAGAAACCGGTGAAAGCCTGACCATTAATTGTGTTCTGACCGATACCAGGTATGCTTGGTTCTCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCCAGGTTCTGTTCGCTCAGCAGGCTGTTTGGACTGATGTTTATGGTGCAGGCACCGTTCTGACCGTTAAT

1H02
ACACGTGTTGATCAGACACCGCGTACCGCAACCAAAGAAACCGGTGAAAGCCTGACCATTAATTGTGTTCTGACCGATACCGGTTATGGTTGGTACGCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCATGGAACCCGTGGTTCCAGTGGGAAGAACTGTGGTATGATGGTGCAGGCACCGTTCTGACCGTTAAT

1A1
ACACGTGTTGATCAGACACCGCGTACCGCAACCAAAGAAACCGGTGAAAGCCTGACCATTAATTGTGTTCTGACCGATACCTACACTATCTGGGTTACTACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCCTGTACTACCAGTGGAACCGTCGTTTCGATGTTTATGGTGCAGGCACCGTTCTGACCGTTAAT

1C04
GCAAGCGTTAATCAGACACCGCGTACCGCAACCAAAGAAACCGGTGAAAGCCTGACCATTAATTGTGTTCTGACCGATACCGACGTTTGGTACGACCATACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCACAGGTTCTGTCTATGTGGGGTAAATGGCAGTGGTATGATGGTGCAGGCACCGTTCTGACCGTTAAT

1A6
ACACGTGTTGATCAGACACCGCGTACCGCAACCAAAGAAACCGGTGAAAGCCTGACCATTAATTGTGTTCTGACCGATACCAGTTATGGTTTGTTCGCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCATGGTCTTACCCGCTGGAACTGCCGAACGGTCGTTTCAAACCGTGGTATGATGGTGCAGGCACCGTTCTGACCGTTAAT

1B2
ACACGTGTTGATCAGACACCGCGTACCGCAACCAAAGAAACCGGTGAAAGCCTGACCATTAATTGTGTTGTTACCGGTGCAGATTATGGTTTGTTCGCCACCTATTGGTATCGTAA
AAATCCGGGTAGCAGCAATCAGGAACGTATTAGCATTAGCGGTCGTTATGTTGAAAGCGTGAATAAACGCACCATGAGCTTTAGCCTGCGTATTAAAGATCTGACCGTTGCAGATA
GCGCAACCTATTACTGTAAAGCACATATCCCGTGGACTGAAGCTTACTGGTATGATGGTGCAGGCACCGTTCTGACCGTTAAT

Fig. 9B
(continued)

2C10
GCAAGCGTTAATCAGACACCGCGTACCGCAACCAAAGAAACCGGTGAAAGCCTGACCATTAATTGTGTTCTGACCGATACCGGTTATGGTTTGGCTGCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCATGGGTTAACTTCCCGCAGTACATGTGGAACTCTTGGATCCCGTGGTATGATGGTGCAGGCACCGTTCTGACCGTTAAT

2C7
ACACGTGTTGATCAGACACCGCGTACCGCAACCAAAGAAACCGGTGAAAGCCTGACCATTAATTGTGTTGTTACCGGTGCAAAGTATGGTTGGTACTCCACCTATTGGTATCGTAA
AAATCCGGGTAGCAGCAATCAGGAACGTATTAGCATTAGCGGTCGTTATGTTGAAAGCGTGAATAAACGCACCATGAGCTTTAGCCTGCGTATTAAAGATCTGACCGTTGCAGATA
GCGCAACCTATATCTGTCGTGCCGGTCCGCCGGTTCCGTCTGGTGGTCTGGATGTTTATGGTGCAGGCACCGTTCTGACCGTTAAT

3E8
ACACGTGTTGATCAGACACCGCGTACCGCAACCAAAGAAACCGGTGAAAGCCTGACCATTAATTGTGTTCTGACCGATACCAGTTATGCTTTGTACTCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCTTCAACATCGGTGTTTGGCCGTGGGCTGATGTTTATGGTGCAGGCACCGTTCTGACCGTTAAT

3G11
ACACGTGTTGATCAGACACCGCGTACCGCAACCAAAGAAACCGGTGAAAGCCTGACCATTAATTGTGTTCTGACCGATACCGGTTATGGTTGGTTCTCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCTGGAAACTGGAACCGCATTCTGCTCAGTGGCAGGATGTTTATGGTGCAGGCACCGTTCTGACCGTTAAT

4B5
ACACGTGTTGATCAGACACCGCGTACCGCAACCAAAGAAACCGGTGAAAGCCTGACCATTAATTGTGTTCTGACCGATACCGTTAAAACTCCGTGGGAAACCAGCTGGTTTCGTAA
AAATCCGGGTACAACCGATTGGGAACGTATGAGCATTGGTGGTCGTTATGTTGAAACGTGAATAAAGGTGCCAAAAGCTTTAGCCTGCGCATTAAAGATCTGACCGTTGCAGATA
GCGCAACCTATATCTGTCGTGCCGACAACTTCCCGTGGATGTGGGTTCAGGCTCTGCATGTTTATGGTGCAGGCACCGTTCTGACCGTTAAT

4G1
ACACGTGTTGATCAGACACCGCGTACCGCAACCAAAGAAACCGGTGAAAGCCTGACCATTAATTGTGTTCTGACCGATACCCTGGGTTACTGGTGGCATACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCTCTGGTATCGCTCGTCAGACTCAGAAAGATGTTTATGGTGCAGGCACCGTTCTGACCGTTAAT

5A12
GCAAGCGTTAATCAGACACCGCGTACCGCAACCAAAGAAACCGGTGAAAGCCTGACCATTAATTGTGTTCTGACCGATACCCTGCATTCTTGGTCTACTACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCATTCTACATGTCTACTGGTTCTTTCCCGTACCCGTGGTGGTATGATGGTGCAGGCACCGTTCTGACCGTTAAT

Fig. 9B
(continued)

5B10
ACACGTGTTGATCAGACACCGCGTACCGCAACCAAAGAAACCGGTGAAAGCCTGACCATTAATTGTGTTCTGACCGATACCTGGAAACAGGTTTGGGCTACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCAGAACTGTTCATCTACAACTGGTATGATGGTGCAGGCACCGTTCTGACCGTTAAT

5B9
GCAAGCGTTAATCAGACACCGCGTACCGCAACCAAAGAAACCGGTGAAAGCCTGACCATTAATTGTGTTCTGACCGATACCGAAGTTCATTGGATGTGGACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCAGGTTTCGCTTGGCATTACCCGTGGTGGTATGATGGTGCAGGCACCGTTCTGACCGTTAAT

5C1
ACACGTGTTGATCAGACACCGCGTACCGCAACCAAAGAAACCGGTGAAAGCCTGACCATTAATTGTGTTCTGACCGATACCGGATATGGTTTGGCTTCCACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCACAGCTGAACTGGTGGAACCGTCAGGCTCCGCGTCATTGGTATGATGGTGCAGGCACCGTTCTGACCGTTAAT

5E6
ACACGTGTTGATCAGACACCGCGTACCGCAACCAAAGAAACCGGTGAAAGCCTGACCATTAATTGTGTTCTGACCGATACCCAGGAACAGAACGTTGCTACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATATCTGTCGTGCCCAGATCCTGGCTCCGCCGCCGTACCAGGATGTTTATGGTGCAGGCACCGTTCTGACCGTTAAT

5F3
GCAAGCGTTAATCAGACACCGCGTACCGCAACCAAAGAAACCGGTGAAAGCCTGACCATTAATTGTGTTCTGACCGATACCTACCATTGGTGGATCCAGACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCAGGTCCGGTTTGGTTCCATATGCTGTGGTATGATGGTGCAGGCACCGTTCTGACCGTTAAT

5F6
ACACGTGTTGATCAGACACCGCGTACCGCAACCAAAGAAACCGGTGAAAGCCTGACCATTAATTGTGTTCTGACCGATACCTGGCTGCCGTTCGACACTACCAGCTGGTTTCGTAA
AAATCCGGGTACAACCGATTGGGAACGTATGAGCATTGGTGGTCGTTATGTTGAAAGCGTGAATAAAGGTGCCAAAAGCTTTAGCCTGCGCATTAAAGATCTGACCGTTGCAGATA
GCGCAACCTATTACTGTAAAGCACGTTGGCCGATCCTGCAGCTGTGGCATTGGTATGATGGTGCAGGCACCGTTCTGACCGTTAAT

5G1
ACACGTGTTGATCAGACACCGCGTACCGCAACCAAAGAAACCGGTGAAAGCCTGACCATTAATTGTGTTCTGACC
GATACCCAGCATCTGTGGTTCGTTTACACCAGCTGGTTTCGTAAAAATCCGGGTACAACCGATTGGGAACGTATG
AGCATTGGTGGTCGTTATGTTGAAAGCGTGAATAAAGGTGCCAAAAGCTTTAGCCTGCGCATTAAAGATCTGACC
GTTGCAGATAGCGCAACCTATTACTGTAAAGCATGGTGGAACCCGTACTGGTTCCAGTGGTATGATGGTGCAGGC
ACCGTTCTGACCGTTAAT

Fig. 9B
(continued)

```
Clone 1  ARVDQTPRSVTKETGESLIINCVLRDPSYAIGSTCWYRKKSGSTNEESISKGGRYVETVNSGGKSFSLRINDLTVEDGGTYRCGAIIWRDSGDYGAINGVRDAAGGGTVVTVN
Clone 2  ARVDQTPRSVTKETGESLIINCVLRDAABAITVTCWSRKKSGSTNEESISKGGRYVETVNSGGKSFSLRINDLTVEDGGTYRCGLEAHCDYGSALPVAACGGTAVTVN
Clone 8  ARVDQTPRSVTKETGESLIINCVLRDGASHGSTCWTRKKSGSTNEESISKGGRYVETVNSGGKSFSLRINDLTVEDGGTYRCALGATEDYGCALPVAACGDGTAVTVN
Clone 10 ARVDQTPRSVTKETGESLIINCVLRDGVAIGSTCWYRKKSGSTNEESISKGGRYVETVNSGGKSFSLRINDLTVEDGGTYRCGHEPGYGGRSDFPYSGAIHGVAACGDGTAVTVN
Clone 11 ARVDQTPRSVTKETGESLIINCVLRDANAIGSTCWYRKKSGSTNEESISKGGRYVETVNSGGKSFSLRINDLTVEDGGTYRCGVWRGSPGDYPYSGAIIGVAACGDGTAVTVN
Clone 12 ARVDQTPRSVTKETGESLIINCVLRDASPAIGSTCWYRKKSGSTNEESISKGGRYVETVNSGGKSFSLRINDLTVEDGGTYRCGVWRACGSDFPYSGAIHGVAACGDGTAVTVN
Clone 13 ARVDQTPRSVTKETGESLIINCVLRDAVPAIGSTCWYRKKSGSTNEESISKGGRYVETVNSGGKSFSLRINDLTVEDGGTYRCGVPIGTGIASGDFTHEGSSPPAHCGDGTAVTVN
Clone 17 ARVDQTPRSVTKETGESLIINCVLRDASWAIGSTCWYRKKSGSTNEESISKGGRYVETVNSGGKSFSLRINDLTVEDGGTYRCGHEPGHGGGSSDFPYSGAIHGVAAGGDGTAVTVN
Clone 18 ARVDQTPRSVTKETGESLIINCVLRESSWALGSTCWYRKKSGSTNEESISKGGRYVETVNSGGKSFSLRIDLTVEDGGTYRCGHEPGYGGRSDPPYSGAIHGVAAGGDGTAVTVN
Clone 20 ARVDQTPRSVTKETGESLIINCVLRDAAGELGSTCWYRKKSGSTNEESISKGGRYVETVNSGGKSFSLRINDLTVEDGGTYRCGVEPFGIGKSGGVHHGSRPPAAGGGTVVTVN
```

Fig. 9C

Clone 1

GCTCGAGTGGACCAAACACCGAGATCAGTAACAAAGGAGAGCGGGCGAATCACTGACCATCAACTGTGTCCTACGAGAGATCCGAGCGTATGCATTGGGCAGCACGTGCTGGTATC
GAAAAAAATCGGGCTCAACAAACGAGGAGAGCATATCGAAAAGGTGGACGATATGTTGAAACAGTTAACAGCGGATCAAAGTCCTTTTCTTTGAGAATTAATGATCTAACAGT
TGAAGACGGTGGCACGTATCGTTGCGGTGCCACCCGATACGGTTGCCGATTGCCGATGCTGCTCTTAACGGACATCGGCGATGCTGCATCGCGGAGTGGCACT
GTCGTGACTGTGAAT

Clone 2

GCTCGAGTGGACCAAACACCGAGATCAGTAACAAAGGAGAGCGGGCGAATCACTGACCATCAACTGTGTCCTACGAGATGCGAGCGCGAGCATTGGTACGCACGTGCTGGTCTC
GAAAAAAATCGGGCTCAACAAACGAGGAGAGCATATCGAAAAGGTGGACGATATGTTGAAACAGTAACAGCGGATCAAAGTCCTTTTCTTTGAGAATTAATGATCTAACAGT
TGAAGACGGTGGCACGTATCGTTGCGGTTGGGTGCTTTCTGTGCTAGGCGCATGCGGAGGTGGCACTGCCGTGCCGTGACTGTGAAT

Clone 8

GCTCGAGTGGACCAAACACCGAGATCAGTAACAAAGGAGAGCGGGCGAATCACTGACCATCAACTGTGTCCTACGAGATGCGGGCGCATCATTGGGCAGCACGTGCTGGACT
CGAAAAAATCGGGCTCAACAAACGAGGAGAGCATATCGAAACAGTTGGACGATATGTTGAAACAGTTAACAGCGGATCAAAGTCCTTTTCTTTGAGAATTAATGATCTAACAG
TTGAAGACGGTGGCACGTATCGTTGCGCCCTGGGTGCTCTTGTGACTGTCTTCCCTATGCTGCATCGGGAGATGGCACTGCCGTGACTGTGAAT

Clone 10

GCTCGAGTGGACCAAACACCGAGATCAGTAACAAAGGAGAGCGGGCGAATCACTGACCATCAACTGTGTCCTTGGAGATGGGAGTTATGCATTGGGCAGCACGTGCTGGTATC
GAAAAAAATCGGGCTCAACAAACGAGGAGAGCATATCGAAAAGGTGGACGATATGTTGAAACAGTAACAGCGGATCAAAGTCCTTTTCTTTGAGAATTAATGATCTAACAGT
TGAAGACGGTGGCACGTATCGTTGCGGTCACTTTCCCTGGTGTGGGGGGGGTGAGCTGTGACTTTCCCTACAGCTGTGCTCTTCACGGCTATGCTGCATGCGGAGACGGCACA
GCCGTGACTGTGAAT

Fig. 9D

Clone 11
GCTCGAGTGGACCAAACACCGAGATCAGTAACAAAGGAGACGGGCGAATCACTGACCATCAACTGTGTCCTACGAGATGCGAACTATGGGCAGCACGTGCTGGTATC
GAAAAAATCGGGCTCAACAAACGAGGAGAGCATATCGAAAGGTGGACGATATGTTGAAACAGTCCTTTTCTTTGAGAATTAATGATCTAACAGT
TGAAGACGGGTGGCACGTATCGTTGCGGTGTCTGGCGGGGATCTCCCATGTGACTACCCATACAGCTGTGCTCTTGTAGGCTATGCTGCGGAGATGGCACTGCCGTG
ACTGTGAAT Clone 12
GCTCGAGTGGACCAAACACCGAGATCACTGACGATCAACTGTGTCCTACGAGATGCGAGCTATGCATTGGGCAGCACGTGCTGGTATC
GAAAAAATCGGGCTCAACAAACGAGGAGAGCATATCGAAACGGTGGACGATATGTTGAAACAGTTAACAGCGGATCAAAGTCCTTTTCTTTGAGAATTAATGATCTAACAGT
TGAAGACGGGTGGCACGTATCGTTGCGGTGTCTGGCGGGTGGCGGAAGCTGTGCTCTTGTAGCCTATGCTGCTGCATCGCGGAGATGGCACTGCCGTG
ACTGTGAAT Clone 13
GCTCGAGTGGACCAAACACCGAGATCAGTAACAAAGGAGACGGGCGAATCACTGACCATCAACTGTGTCCTACGAGATGCGATCTATGCATTGGGCAGCACGTGCTGGTATC
GAAAAAATCGGGCTCAACAAACGAGGAGAGCATATCGAAAAGGTGGACGATATGTTGAAACAGTTAACAGCGGATCAAAGTCCTTTTCTCTTGAGAATTAATGATCTAACAGT
TGAAGACGGGTGGCACGTATCGTTGCGGTGTCCCACCCAATTACGGGGATAAAGAGCTGTGACTACATCCATCTGTCTCTTCCTCCCTGCTGCATGCGGAGATGGCACTG
CCGTGACTGTGAAT Clone 17
GCTCGAGTGGACCAAACACCGAGATCAGTAACAAAGGAGACGGGCGAATCACTGACCATCAACTGTGTCCTACGAGATGCGAGCTATGCATTGGGCAGCACGTGCTGGTATC
GAAAAAAATCGGGCTCAACAAACGAGGAGAGCATATCGAAAGGTGGACGATATGTTGAAACAGTTAACAGCGGATCAAAGTCCTTTTCTTTGAGAATTAATGATCTAACAGT
TGAAGACGGGTGGCACGTATCGTTGCGGTCACTTTCCTGGTGTGGGGGGGGAGCTGTGACTTTCCTACAGCTGTCTTTCAGGCTATGCTGCATGCGGAGATGGCACT
GCCGTGACTGTGAAT Fig. 9D (continued)

Clone 18

GCTCGAGTGGACCAAACACCGAGATCAGTAACAAAGGAGACGGGCGAATCACTGACCATCAACTGTGTCCTACGAGAATCGAGCTATGCATTGGGCAGCACGTGCTGGTATC
GAAAAAAATCGGGCTCAACAAACGAGGAGCATATCGAAAGGTGGACGACGATATGTTGAAACAGTTAACAGGGATCAAAGTCCTTTCTTTGAGAATTAGTGATCTAACAGT
TGAAGACGGTGGCACGTATCGTTGCGGTCACTTTCCTGGTGTGGGGGGCCGGAGCTGTGACTTTCCCTACAGTCTGCTCTTCACGGCTATGCTGCATGGGAGATGGCACTG
CCGTGACTGTGAAT

Clone 20

GCTCGAGTGGACCAAACACCGAGATCAGTAACAAAGGAGACGGGCGAATCACTGACCATCAACTGTGTCCTACGAGATGCGAGAGGTGAATTGGGCAGCACGTGCTGGTAT
CGAAAAAATCGGGCTCAACAAACGAGGAGAGCATATCGAAAGGTGGACGATATGTTGAAACAGTTAACAGGCGATCAAAGTCCTTTCTTTGAGAATTAATGATCTAACAG
TTGAAGACGGTGGCACGTATCGTTGCGGTGTCCCACCCCGTTTACGGGGATAAAGAGCTGTGACTACATCCATCTGTCTCTGCATGCGGAGGTGGCACT
GTCGTGACTGTGAAT

Fig. 9D
(continued)

| Source | CDR1 | CDR3 |
|---|---|---|
| 1A9 | WKWWLQ | GPIYFETWHDV |
| 1C8 | PQNWQA | VFLNPWDWPHWY |
| 1D12 | GYGLAA | WWDVPQRWEPVSNYWY |
| 2B6 | SPTGTF | PYYQYNDWHDV |
| 2D3 | WTTWVG | QTPWWMQWHLSMWY |
| 2D4 | DYGLFS | FTWPWEWPDRWFRPWY |
| 2E8 | NYAWFS | LYPGWKWPWHNFWY |
| 1G5 | RYAWFS | QVLFAQQAVWTDV |
| 1H02 | GYGWYA | WNPWFQWEELWY |
| 1A1 | YTIWVT | LYYQWNRRFDV |
| 1C04 | DVWYDH | QVLSMWGKWQWY |
| 1A6 | SYGLFA | WSYPLELPNGRFKPWY |
| 1B2 | DYGLFA | HIPWTEAYWY |

Fig. 10A

| | | |
|---|---|---|
| 2C10 | GYGLAA | WVNFPQYMWNSWIPWY |
| 2C7 | KYGWYS | GPPVPSGGLDV |
| 3E8 | SYALYS | FNIGVWPWADV |
| 3G11 | GYGWFS | WKLEPHSAQWQDV |
| 4B5 | VKTPWE | NFPWMWVQALDV |
| 4G1 | LGYWWH | SGIARQTQKDV |
| 5A12 | LHSWST | FYMSTGSFPYPWW |
| 5B10 | WKQVWA | ELFIYNW |
| 5B9 | EVHWMW | GFAWHYPWW |
| 5C1 | GYGLAS | QLNWWNRQAPRHW |
| 5E6 | QEQNVA | QILAPPPYQDV |
| 5F3 | YHWWIQ | GPVWFHMLW |
| 5F6 | WLPFDT | RWPILQLWHW |
| 5G1 | QHLWFVY | WWNPYWFQW |

Fig. 10A
(continued)

| Source | CDR1 | CDR3 |
|---|---|---|
| Clone 1 | SYALGS | TDTVRIYSCDYLCALNGHRDAA |
| Clone 2 | SAALVR | GAFCDYGCALPYAA |
| Clone 8 | GASLGS | GAFCDYGCALPYAA |
| Clone 10 | SYALGS | FPGVGGRSCDFPYSCALHGYAA |
| Clone 11 | NYALGS | WRGISPCDYPYSCALVGYAA |
| Clone 12 | SYALGS | WRAGGSCDFPYSCALVGYAA |
| Clone 13 | IYALGS | PTQFTGIKSCDYIHLCSSFPAA |
| Clone 17 | SYALGS | FPGVGGGSCDFPYSCALHGYAA |
| Clone 18 | SYALGS | FPGVGGRSCDFPYSCALHGYAA |
| Clone 20 | RGELGS | PTPFTGIKSCDYIHLCSRFPAA |

Fig. 10B

T1: FW1 | CDR1 | FW2 | HV2 | FW3a | HV4 | FW3b | CDR3 | FW4

CDR3 sequences (T1):
- CVFMGIDWRLGQLYWDV
- QALIIVDFQALDV
- VGYDTGFVGRRESDV
- WERLVMPEDDV
- RCFLFQIDDV
- GSKGKGFDV
- TLCASSHMGNVVADV T2: FW1 | CDR1 | FW2 | HV2 | FW3a | HV4 | FW3b | CDR3 | FW4

CDR3 sequences (T2):
- VHLFNPIFHMHDV
- TNPSGHLWFYRRLFYDV
- KWRPPLQEQDV
- ICHQSNVDV

Fig. 10C

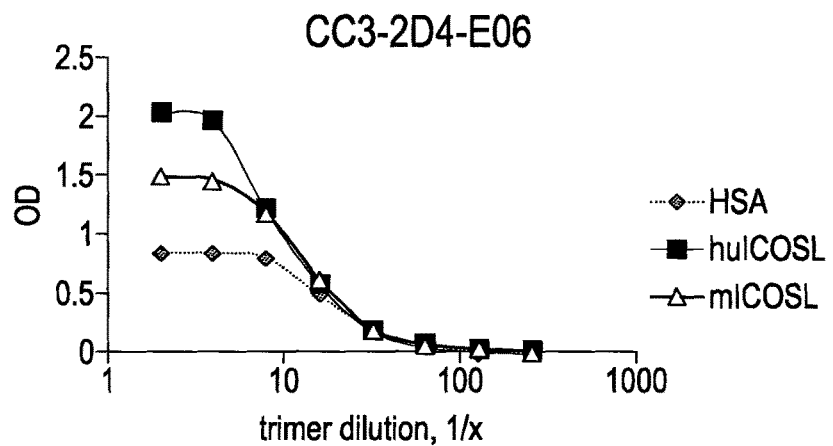

Fig. 11A

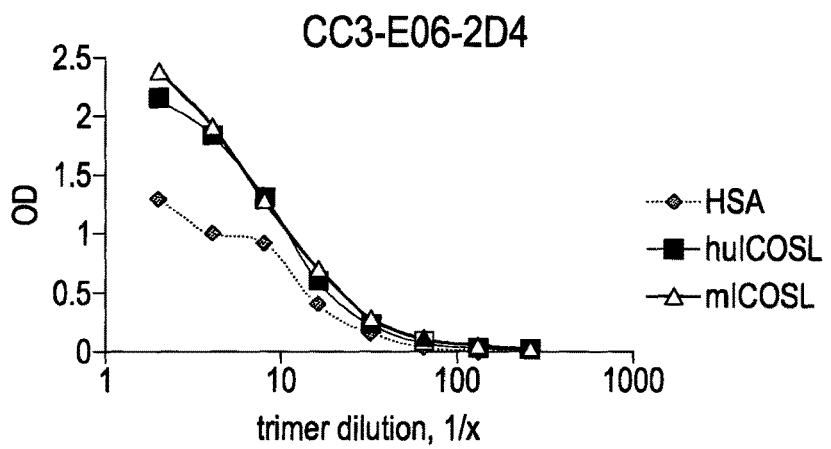

Fig. 11B 1 mrlgspgllf llfsslradt qekevramvg sdvelscacp egsrfdlndv yvywqtsesk
61 tvvtyhipqn sslenvdsry mralmspag mlrgdfslrl fnvtpqdeqk fhclvlsqsl
121 gfqevlsvev tlhvaanfsv pvvsaphsps qdeltftcts ingyprpnvy winktdnsll
181 dqalqndtvf lnmrglydvv svlriartps vnigccienv llqqnltvgs qtgndigerd
241 kitenpvstg eknaatwsil avlcllvvva vaigwvcrdr clqhsyagaw avspeteltg
301 hv

Fig. 12

SEQUENCE LISTING

```
<160> NUMBER OF SEQ ID NOS: 177

<210> SEQ ID NO 1
<211> LENGTH: 27
<212> TYPE: PRT
<213> ORGANISM: Artificial sequence
<220> FEATURE:
<223> OTHER INFORMATION: Synthetic sequence: A in Formula I of PCT/
      EP2014/058276
<220> FEATURE:
<221> NAME/KEY: VARIANT
<222> LOCATION: (24)..(27)
<223> OTHER INFORMATION: In an embodiment, Xaa at location 24 is Leu and
      Xaa Xaa at location 26-27 is Asp Thr
<220> FEATURE:
```

```
<221> NAME/KEY: VARIANT
<222> LOCATION: (24)..(27)
<223> OTHER INFORMATION: In an embodiment, Xaa at location 24 is Val and
      Xaa Xaa at location 26-27 is Gly Ala

<400> SEQUENCE: 1

Thr Arg Val Asp Gln Thr Pro Arg Thr Ala Thr Lys Glu Thr Gly Glu
1               5                   10                  15

Ser Leu Thr Ile Asn Cys Val Xaa Thr Xaa Xaa
            20                  25

<210> SEQ ID NO 2
<211> LENGTH: 52
<212> TYPE: PRT
<213> ORGANISM: Artificial sequence
<220> FEATURE:
<223> OTHER INFORMATION: Synthetic sequence: B in Formula I of PCT/
      EP2014/058276
<220> FEATURE:
<221> NAME/KEY: VARIANT
<222> LOCATION: (49)..(51)
<223> OTHER INFORMATION: In an embodiment, Xaa at location 49 is Tyr and
      Xaa at location 51 is Lys
<220> FEATURE:
<221> NAME/KEY: VARIANT
<222> LOCATION: (49)..(51)
<223> OTHER INFORMATION: In an embodiment, Xaa at location 49 is Ile and
      Xaa at location 51 is Arg

<400> SEQUENCE: 2

Thr Ser Trp Phe Arg Lys Asn Pro Gly Thr Thr Asp Trp Glu Arg Met
1               5                   10                  15

Ser Ile Gly Gly Arg Tyr Val Glu Ser Val Asn Lys Gly Ala Lys Ser
            20                  25                  30

Phe Ser Leu Arg Ile Lys Asp Leu Thr Val Ala Asp Ser Ala Thr Tyr
        35                  40                  45

Xaa Cys Xaa Ala
    50

<210> SEQ ID NO 3
<211> LENGTH: 10
<212> TYPE: PRT
<213> ORGANISM: Artificial sequence
<220> FEATURE:
<223> OTHER INFORMATION: Synthetic sequence: C in Formula I of PCT/
      EP2014/058276

<400> SEQUENCE: 3

Asp Gly Ala Gly Thr Val Leu Thr Val Asn
1               5                   10

<210> SEQ ID NO 4
<211> LENGTH: 27
<212> TYPE: PRT
<213> ORGANISM: Artificial sequence
<220> FEATURE:
<223> OTHER INFORMATION: Synthetic sequence: A in Formula I of PCT/
      EP2014/058276

<400> SEQUENCE: 4

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr
            20                  25

<210> SEQ ID NO 5
```

```
<211> LENGTH: 52
<212> TYPE: PRT
<213> ORGANISM: Artificial sequence
<220> FEATURE:
<223> OTHER INFORMATION: Synthetic sequence: B in Formula I of PCT/
      EP2014/058276
<220> FEATURE:
<221> NAME/KEY: VARIANT
<222> LOCATION: (49)..(51)
<223> OTHER INFORMATION: In an embodiment, Xaa at location 49 is Tyr and
      Xaa at location 51 is Lys
<220> FEATURE:
<221> NAME/KEY: VARIANT
<222> LOCATION: (49)..(51)
<223> OTHER INFORMATION: In an embodiment, Xaa at location 49 is Ile and
      Xaa at location 51 is Arg

<400> SEQUENCE: 5

Thr Tyr Trp Tyr Arg Lys Asn Pro Gly Ser Ser Asn Gln Glu Arg Ile
1               5                   10                  15

Ser Ile Ser Gly Arg Tyr Val Glu Ser Val Asn Lys Arg Thr Met Ser
            20                  25                  30

Phe Ser Leu Arg Ile Lys Asp Leu Thr Val Ala Asp Ser Ala Thr Tyr
        35                  40                  45

Xaa Cys Xaa Ala
    50

<210> SEQ ID NO 6
<211> LENGTH: 10
<212> TYPE: PRT
<213> ORGANISM: Artificial sequence
<220> FEATURE:
<223> OTHER INFORMATION: Synthetic sequence: C in Formula I of PCT/
      EP2014/058276

<400> SEQUENCE: 6

Tyr Gly Ala Gly Thr Val Leu Thr Val Asn
1               5                   10

<210> SEQ ID NO 7
<211> LENGTH: 27
<212> TYPE: PRT
<213> ORGANISM: Artificial sequence
<220> FEATURE:
<223> OTHER INFORMATION: Synthetic sequence: A in Formula I of PCT/
      EP2014/058276
<220> FEATURE:
<221> NAME/KEY: VARIANT
<222> LOCATION: (26)..(27)
<223> OTHER INFORMATION: In an embodiment, Xaa Xaa at location 26-27 is
      Asp Pro
<220> FEATURE:
<221> NAME/KEY: VARIANT
<222> LOCATION: (26)..(27)
<223> OTHER INFORMATION: In an embodiment, Xaa Xaa at location 26-27 is
      Asp Ala
<220> FEATURE:
<221> NAME/KEY: VARIANT
<222> LOCATION: (26)..(27)
<223> OTHER INFORMATION: In an embodiment, Xaa Xaa at location 26-27 is
      Asp Gly
<220> FEATURE:
<221> NAME/KEY: VARIANT
<222> LOCATION: (26)..(27)
<223> OTHER INFORMATION: In an embodiment, Xaa Xaa at location 26-27 is
      Glu Ser

<400> SEQUENCE: 7

Ala Arg Val Asp Gln Thr Pro Arg Ser Val Thr Lys Glu Thr Gly Glu
1               5                   10                  15
```

-continued

```
Ser Leu Thr Ile Asn Cys Val Leu Arg Xaa Xaa
            20                  25

<210> SEQ ID NO 8
<211> LENGTH: 52
<212> TYPE: PRT
<213> ORGANISM: Artificial sequence
<220> FEATURE:
<223> OTHER INFORMATION: Synthetic sequence: B in Formula I of PCT/
      EP2014/058276
<220> FEATURE:
<221> NAME/KEY: VARIANT
<222> LOCATION: (4, 38, 51, 52)
<223> OTHER INFORMATION: In an embodiment, Xaa at location 4 is Tyr, Xaa
      at location 38 is Asn, and Xaa Xaa at location 51-52 is Gly Ala
<220> FEATURE:
<221> NAME/KEY: VARIANT
<222> LOCATION: (4, 38, 51, 52)
<223> OTHER INFORMATION: In an embodiment, Xaa at location 4 is Ser, Xaa
      at location 38 is Asn, and Xaa Xaa at location 51-52 is Gly Leu
<220> FEATURE:
<221> NAME/KEY: VARIANT
<222> LOCATION: (4, 38, 51, 52)
<223> OTHER INFORMATION: In an embodiment, Xaa at location 4 is Thr, Xaa
      at location 38 is Asn, and Xaa Xaa at location 51-52 is Ala Leu
<220> FEATURE:
<221> NAME/KEY: VARIANT
<222> LOCATION: (4, 38, 51, 52)
<223> OTHER INFORMATION: In an embodiment, Xaa at location 4 is Tyr, Xaa
      at location 38 is Asn, and Xaa Xaa at location 51-52 is Gly Val
<220> FEATURE:
<221> NAME/KEY: VARIANT
<222> LOCATION: (4, 38, 51, 52)
<223> OTHER INFORMATION: In an embodiment, Xaa at location 4 is Tyr, Xaa
      at location 38 is Asn, and Xaa Xaa at location 51-52 is Gly His
<220> FEATURE:
<221> NAME/KEY: VARIANT
<222> LOCATION: (4, 38, 51, 52)
<223> OTHER INFORMATION: In an embodiment, Xaa at location 4 is Tyr, Xaa
      at location 38 is Ser, and Xaa Xaa at location 51-52 is Gly His

<400> SEQUENCE: 8

Thr Cys Trp Xaa Arg Lys Lys Ser Gly Ser Thr Asn Glu Glu Ser Ile
1               5                   10                  15

Ser Lys Gly Gly Arg Tyr Val Glu Thr Val Asn Ser Gly Ser Lys Ser
            20                  25                  30

Phe Ser Leu Arg Ile Xaa Asp Leu Thr Val Glu Asp Gly Gly Thr Tyr
        35                  40                  45

Arg Cys Xaa Xaa
    50

<210> SEQ ID NO 9
<211> LENGTH: 10
<212> TYPE: PRT
<213> ORGANISM: Artificial sequence
<220> FEATURE:
<223> OTHER INFORMATION: Synthetic sequence: C in Formula I of PCT/
      EP2014/058276
<220> FEATURE:
<221> NAME/KEY: VARIANT
<222> LOCATION: (3)..(6)
<223> OTHER INFORMATION: In an embodiment, Xaa at location 3 is Gly and
      Xaa at location 6 is Val
<220> FEATURE:
<221> NAME/KEY: VARIANT
<222> LOCATION: (3)..(6)
<223> OTHER INFORMATION: In an embodiment, Xaa at location 3 is Gly and
      Xaa at location 6 is Ala
<220> FEATURE:
<221> NAME/KEY: VARIANT
<222> LOCATION: (3)..(6)
<223> OTHER INFORMATION: In an embodiment, Xaa at location 3 is Asp and
      Xaa at location 6 is Ala
```

<400> SEQUENCE: 9

Cys Gly Xaa Gly Thr Xaa Val Thr Val Asn
1               5                   10

<210> SEQ ID NO 10
<211> LENGTH: 4
<212> TYPE: PRT
<213> ORGANISM: Artificial sequence
<220> FEATURE:
<223> OTHER INFORMATION: Synthetic sequence: Linker

<400> SEQUENCE: 10

Gly Gly Gly Gly
1

<210> SEQ ID NO 11
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 11

Gly Gly Gly Gly Gly
1               5

<210> SEQ ID NO 12
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 12

Gly Gly Gly Gly Ser
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic sequence: Linker

<400> SEQUENCE: 13

Gly Gly Gly Gly Ser Gly Gly Gly Gly
1               5

<210> SEQ ID NO 14
<211> LENGTH: 15
<212> TYPE: PRT
<213> ORGANISM: Artificial sequence
<220> FEATURE:
<223> OTHER INFORMATION: Synthetic sequence: Linker

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 9
<212> TYPE: PRT
<213> ORGANISM: Artificial sequence
<220> FEATURE:
<223> OTHER INFORMATION: Synthetic sequence: Linker

<400> SEQUENCE: 15

Ala Ala Ala His His His His His
1               5

<210> SEQ ID NO 16
<211> LENGTH: 106
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 16

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Trp Lys Trp Trp Leu
            20                  25                  30

Gln Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gly Pro Ile Tyr Phe Glu Thr Trp His Asp Val
                85                  90                  95

Tyr Gly Ala Gly Thr Val Leu Thr Val Asn
            100                 105

<210> SEQ ID NO 17
<211> LENGTH: 107
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 17

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Pro Gln Asn Trp Gln
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Val Phe Leu Asn Pro Trp Asp Trp Pro His Trp
                85                  90                  95

Tyr Asp Gly Ala Gly Thr Val Leu Thr Val Asn
            100                 105

<210> SEQ ID NO 18
<211> LENGTH: 111
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 18

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Gly Leu Ala
                20                  25                  30

Ala Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Trp Trp Asp Val Pro Gln Arg Trp Glu Pro Val
                85                  90                  95

Ser Asn Tyr Trp Tyr Asp Gly Ala Gly Thr Val Leu Thr Val Asn
            100                 105                 110

<210> SEQ ID NO 19
<211> LENGTH: 106
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 19

Thr Arg Val Asp Gln Thr Pro Arg Thr Ala Thr Lys Glu Thr Gly Glu
1               5                   10                  15

Ser Leu Thr Ile Asn Cys Val Leu Thr Asp Ser Pro Thr Gly Thr
                20                  25                  30

Phe Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Ile Cys Arg Ala Pro Tyr Tyr Gln Tyr Asn Asp Trp His Asp Val
                85                  90                  95

Tyr Gly Ala Gly Thr Val Leu Thr Val Asn
            100                 105

<210> SEQ ID NO 20
<211> LENGTH: 109
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 20

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Trp Thr Thr Trp Val
                20                  25                  30

Gly Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
        50                  55                  60

Ser Phe Ser Leu Arg Ile Lys Asp Leu Thr Val Ala Asp Ser Ala Thr
65                  70                  75                  80

Tyr Tyr Cys Lys Ala Gln Thr Pro Trp Trp Met Gln Trp His Leu Ser
                85                  90                  95

Met Trp Tyr Asp Gly Ala Gly Thr Val Leu Thr Val Asn
            100                 105

<210> SEQ ID NO 21
<211> LENGTH: 111
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 21

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asp Tyr Gly Leu Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Phe Thr Trp Pro Trp Glu Trp Pro Asp Arg Trp
                85                  90                  95

Phe Arg Pro Trp Tyr Asp Gly Ala Gly Thr Val Leu Thr Val Asn
            100                 105                 110

<210> SEQ ID NO 22
<211> LENGTH: 109
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 22

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Asn Tyr Ala Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Leu Tyr Pro Gly Trp Lys Trp Pro Trp His Asn
                85                  90                  95

Phe Trp Tyr Asp Gly Ala Gly Thr Val Leu Thr Val Asn
            100                 105

<210> SEQ ID NO 23
<211> LENGTH: 108
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 23

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Arg Tyr Ala Trp Phe
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gln Val Leu Phe Ala Gln Gln Ala Val Trp Thr
                85                  90                  95

Asp Val Tyr Gly Ala Gly Thr Val Leu Thr Val Asn
            100                 105

<210> SEQ ID NO 24
<211> LENGTH: 107
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 24

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Gly Trp Tyr
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Trp Asn Pro Trp Phe Gln Trp Glu Glu Leu Trp
                85                  90                  95

Tyr Asp Gly Ala Gly Thr Val Leu Thr Val Asn
            100                 105

<210> SEQ ID NO 25
<211> LENGTH: 106
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 25

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Tyr Thr Ile Trp Val
            20                  25                  30

Thr Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

```
Ser Phe Ser Leu Arg Ile Lys Asp Leu Thr Val Ala Asp Ser Ala Thr
 65                  70                  75                  80

Tyr Ile Cys Arg Ala Leu Tyr Tyr Gln Trp Asn Arg Arg Phe Asp Val
                 85                  90                  95

Tyr Gly Ala Gly Thr Val Leu Thr Val Asn
            100                 105

<210> SEQ ID NO 26
<211> LENGTH: 107
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 26

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Asp Val Trp Tyr Asp
                 20                  25                  30

His Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Gln Val Leu Ser Met Trp Gly Lys Trp Gln Trp
                 85                  90                  95

Tyr Asp Gly Ala Gly Thr Val Leu Thr Val Asn
            100                 105

<210> SEQ ID NO 27
<211> LENGTH: 111
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 27

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Gly Leu Phe
                 20                  25                  30

Ala Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Trp Ser Tyr Pro Leu Glu Leu Pro Asn Gly Arg
                 85                  90                  95

Phe Lys Pro Trp Tyr Asp Gly Ala Gly Thr Val Leu Thr Val Asn
            100                 105                 110

<210> SEQ ID NO 28
<211> LENGTH: 105
<212> TYPE: PRT
<213> ORGANISM: Artificial sequence
<220> FEATURE:
```

<223> OTHER INFORMATION: Synthetic sequence: Amino acid sequence of
synthetic library derived anti-hICOSL VNAR domains

<400> SEQUENCE: 28

Thr Arg Val Asp Gln Thr Pro Arg Thr Ala Thr Lys Glu Thr Gly Glu
1               5                   10                  15

Ser Leu Thr Ile Asn Cys Val Val Thr Gly Ala Asp Tyr Gly Leu Phe
            20                  25                  30

Ala Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met
    50                  55                  60

Ser Phe Ser Leu Arg Ile Lys Asp Leu Thr Val Ala Asp Ser Ala Thr
65                  70                  75                  80

Tyr Tyr Cys Lys Ala His Ile Pro Trp Thr Glu Ala Tyr Trp Tyr Asp
                85                  90                  95

Gly Ala Gly Thr Val Leu Thr Val Asn
            100                 105

<210> SEQ ID NO 29
<211> LENGTH: 111
<212> TYPE: PRT
<213> ORGANISM: Artificial sequence
<220> FEATURE:
<223> OTHER INFORMATION: Synthetic sequence: Amino acid sequence of
synthetic library derived anti-hICOSL VNAR domains

<400> SEQUENCE: 29

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Gly Tyr Gly Leu Ala
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Trp Val Asn Phe Pro Gln Tyr Met Trp Asn Ser
                85                  90                  95

Trp Ile Pro Trp Tyr Asp Gly Ala Gly Thr Val Leu Thr Val Asn
            100                 105                 110

<210> SEQ ID NO 30
<211> LENGTH: 106
<212> TYPE: PRT
<213> ORGANISM: Artificial sequence
<220> FEATURE:
<223> OTHER INFORMATION: Synthetic sequence: Amino acid sequence of
synthetic library derived anti-hICOSL VNAR domains

<400> SEQUENCE: 30

Thr Arg Val Asp Gln Thr Pro Arg Thr Ala Thr Lys Glu Thr Gly Glu
1               5                   10                  15

Ser Leu Thr Ile Asn Cys Val Val Gly Ala Lys Tyr Gly Trp Tyr
            20                  25                  30

Ser Thr Tyr Trp Tyr Arg Lys Asn Pro Gly Ser Ser Asn Gln Glu Arg
        35                  40                  45

Ile Ser Ile Ser Gly Arg Tyr Val Glu Ser Val Asn Lys Arg Thr Met

```
                 50                  55                  60
Ser Phe Ser Leu Arg Ile Lys Asp Leu Thr Val Ala Asp Ser Ala Thr
 65                  70                  75                  80

Tyr Ile Cys Arg Ala Gly Pro Pro Val Pro Ser Gly Gly Leu Asp Val
                 85                  90                  95

Tyr Gly Ala Gly Thr Val Leu Thr Val Asn
                100                 105
```

<210> SEQ ID NO 31
<211> LENGTH: 106
<212> TYPE: PRT
<213> ORGANISM: Artificial sequence
<220> FEATURE:
<223> OTHER INFORMATION: Synthetic sequence: Amino acid sequence of
     synthetic library derived anti-hICOSL VNAR domains

<400> SEQUENCE: 31

```
Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Ser Tyr Ala Leu Tyr
                20                  25                  30

Ser Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
         50                  55                  60

Ser Phe Ser Leu Arg Ile Lys Asp Leu Thr Val Ala Asp Ser Ala Thr
 65                  70                  75                  80

Tyr Ile Cys Arg Ala Phe Asn Ile Gly Val Trp Pro Trp Ala Asp Val
                 85                  90                  95

Tyr Gly Ala Gly Thr Val Leu Thr Val Asn
                100                 105
```

<210> SEQ ID NO 32
<211> LENGTH: 108
<212> TYPE: PRT
<213> ORGANISM: Artificial sequence
<220> FEATURE:
<223> OTHER INFORMATION: Synthetic sequence: Amino acid sequence of
     synthetic library derived anti-hICOSL VNAR domains

<400> SEQUENCE: 32

```
Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Gly Tyr Gly Trp Phe
                20                  25                  30

Ser Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
         50                  55                  60

Ser Phe Ser Leu Arg Ile Lys Asp Leu Thr Val Ala Asp Ser Ala Thr
 65                  70                  75                  80

Tyr Ile Cys Arg Ala Trp Lys Leu Glu Pro His Ser Ala Gln Trp Gln
                 85                  90                  95

Asp Val Tyr Gly Ala Gly Thr Val Leu Thr Val Asn
                100                 105
```

<210> SEQ ID NO 33
<211> LENGTH: 108
<212> TYPE: PRT

```
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 33

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Val Lys Thr Pro Trp
            20                  25                  30

Glu Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Asp Asn Phe Pro Trp Met Trp Val Gln Ala Leu
                85                  90                  95

Asp Val Tyr Gly Ala Gly Thr Val Leu Thr Val Asn
            100                 105

<210> SEQ ID NO 34
<211> LENGTH: 106
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 34

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Leu Gly Tyr Trp Trp
            20                  25                  30

His Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Ser Gly Ile Ala Arg Gln Thr Gln Lys Asp Val
                85                  90                  95

Tyr Gly Ala Gly Thr Val Leu Thr Val Asn
            100                 105

<210> SEQ ID NO 35
<211> LENGTH: 109
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 35

Ala Ser Val Asn Gln Thr Pro Arg Thr Ala Lys Glu Thr Gly Glu
1               5                   10                  15

Ser Leu Thr Ile Asn Cys Val Leu Thr Asp Thr Leu His Ser Trp Ser
            20                  25                  30

Thr Thr Ser Trp Phe Arg Lys Asn Pro Gly Thr Thr Asp Trp Glu Arg
        35                  40                  45
```

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
 65                  70                  75                  80

Tyr Tyr Cys Lys Ala Phe Tyr Met Ser Thr Gly Ser Phe Pro Tyr Pro
                 85                  90                  95

Trp Trp Tyr Asp Gly Ala Gly Thr Val Leu Thr Val Asn
            100                 105

<210> SEQ ID NO 36
<211> LENGTH: 103
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 36

Thr Arg Val Asp Gln Thr Pro Arg Thr Ala Thr Lys Glu Thr Gly Glu
 1               5                  10                  15

Ser Leu Thr Ile Asn Cys Val Leu Thr Asp Thr Trp Lys Gln Val Trp
                20                  25                  30

Ala Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
 65                  70                  75                  80

Tyr Tyr Cys Lys Ala Glu Leu Phe Ile Tyr Asn Trp Tyr Asp Gly Ala
                 85                  90                  95

Gly Thr Val Leu Thr Val Asn
            100

<210> SEQ ID NO 37
<211> LENGTH: 105
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 37

Ala Ser Val Asn Gln Thr Pro Arg Thr Ala Thr Lys Glu Thr Gly Glu
 1               5                  10                  15

Ser Leu Thr Ile Asn Cys Val Leu Thr Asp Thr Glu Val His Trp Met
                20                  25                  30

Trp Thr Ser Trp Phe Arg Lys Asn Pro Gly Thr Thr Asp Trp Glu Arg
             35                  40                  45

Met Ser Ile Gly Gly Arg Tyr Val Glu Ser Val Asn Lys Gly Ala Lys
            50                  55                  60

Ser Phe Ser Leu Arg Ile Lys Asp Leu Thr Val Ala Asp Ser Ala Thr
 65                  70                  75                  80

Tyr Tyr Cys Lys Ala Gly Phe Ala Trp His Tyr Pro Trp Trp Tyr Asp
                 85                  90                  95

Gly Ala Gly Thr Val Leu Thr Val Asn
            100                 105

<210> SEQ ID NO 38

```
<211> LENGTH: 109
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 38

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gly Tyr Gly Leu Ala
            20                  25                  30

Ser Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Tyr Cys Lys Ala Gln Leu Asn Trp Trp Asn Arg Gln Ala Pro Arg
                85                  90                  95

His Trp Tyr Asp Gly Ala Gly Thr Val Leu Thr Val Asn
            100                 105

<210> SEQ ID NO 39
<211> LENGTH: 106
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 39

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gln Glu Gln Asn Val
            20                  25                  30

Ala Thr Ser Trp Phe Arg Lys Asn Pro Gly Thr Thr Asp Trp Glu Arg
        35                  40                  45

Met Ser Ile Gly Gly Arg Tyr Val Glu Ser Val Asn Lys Gly Ala Lys
    50                  55                  60

Ser Phe Ser Leu Arg Ile Lys Asp Leu Thr Val Ala Asp Ser Ala Thr
65                  70                  75                  80

Tyr Ile Cys Arg Ala Gln Ile Leu Ala Pro Pro Tyr Gln Asp Val
                85                  90                  95

Tyr Gly Ala Gly Thr Val Leu Thr Val Asn
            100                 105

<210> SEQ ID NO 40
<211> LENGTH: 105
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 40

Ala Ser Val Asn Gln Thr Pro Arg Thr Ala Thr Lys Glu Thr Gly Glu
1               5                   10                  15

Ser Leu Thr Ile Asn Cys Val Leu Thr Asp Thr Tyr His Trp Trp Ile
            20                  25                  30
```

```
Gln Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Gly Pro Val Trp Phe His Met Leu Trp Tyr Asp
            85                  90                  95

Gly Ala Gly Thr Val Leu Thr Val Asn
            100                 105

<210> SEQ ID NO 41
<211> LENGTH: 106
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 41

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Trp Leu Pro Phe Asp
            20                  25                  30

Thr Thr Ser Trp Phe Arg Lys Asn Pro Gly Thr Thr Asp Trp Glu Arg
            35                  40                  45

Met Ser Ile Gly Gly Arg Tyr Val Glu Ser Val Asn Lys Gly Ala Lys
 50                  55                  60

Ser Phe Ser Leu Arg Ile Lys Asp Leu Thr Val Ala Asp Ser Ala Thr
 65                  70                  75                  80

Tyr Tyr Cys Lys Ala Arg Trp Pro Ile Leu Gln Leu Trp His Trp Tyr
            85                  90                  95

Asp Gly Ala Gly Thr Val Leu Thr Val Asn
            100                 105

<210> SEQ ID NO 42
<211> LENGTH: 106
<212> TYPE: PRT
<213> ORGANISM: Artificial sequence
<220> FEATURE:
<223> OTHER INFORMATION: Synthetic sequence: Amino acid sequence of
      synthetic library derived anti-hICOSL VNAR domains

<400> SEQUENCE: 42

Thr Arg Val Asp Gln Thr Pro Arg Thr Ala Thr Lys Glu Thr Gly Glu
1               5                   10                  15

Ser Leu Thr Ile Asn Cys Val Leu Thr Asp Thr Gln His Leu Trp Phe
            20                  25                  30

Val Tyr Thr Ser Trp Phe Arg Lys Asn Pro Gly Thr Thr Asp Trp Glu
            35                  40                  45

Arg Met Ser Ile Gly Gly Arg Tyr Val Glu Ser Val Asn Lys Gly Ala
 50                  55                  60

Lys Ser Phe Ser Leu Arg Ile Lys Asp Leu Thr Val Ala Asp Ser Ala
 65                  70                  75                  80

Thr Tyr Tyr Cys Lys Ala Trp Trp Asn Pro Tyr Trp Phe Gln Trp Tyr
            85                  90                  95

Asp Gly Ala Gly Thr Val Leu Thr Val Asn
            100                 105
```

<210> SEQ ID NO 43
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 43

| | | | | | |
|---|---|---|---|---|---|
| gcaagcgtta | atcagacacc | gcgtaccgca | accaaagaaa | ccggtgaaag | cctgaccatt | 60 |
| aattgtgttc | tgaccgatac | ctggaaatgg | tggctgcaga | ccagctggtt | tcgtaaaaat | 120 |
| ccgggtacaa | ccgattggga | acgtatgagc | attggtggtc | gttatgttga | aagcgtgaat | 180 |
| aaaggtgcca | aaagctttag | cctgcgcatt | aaagatctga | ccgttgcaga | tagcgcaacc | 240 |
| tatatctgtc | gtgccggtcc | gatctacttc | gaaacttggc | atgatgttta | tggtgcaggc | 300 |
| accgttctga | ccgttaat | | | | | 318 |

<210> SEQ ID NO 44
<211> LENGTH: 321
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 44

| | | | | | |
|---|---|---|---|---|---|
| gcaagcgtta | atcagacacc | gcgtaccgca | accaaagaaa | ccggtgaaag | cctgaccatt | 60 |
| aattgtgttc | tgaccgatac | cccgcagaac | tggcaagcta | ccagctggtt | tcgtaaaaat | 120 |
| ccgggtacaa | ccgattggga | acgtatgagc | attggtggtc | gttatgttga | aagcgtgaat | 180 |
| aaaggtgcca | aaagctttag | cctgcgcatt | aaagatctga | ccgttgcaga | tagcgcaacc | 240 |
| tattactgta | aagcagttt | cctgaacccg | tgggactggc | cgcattggta | tgatggtgca | 300 |
| ggcaccgttc | tgaccgttaa | t | | | | 321 |

<210> SEQ ID NO 45
<211> LENGTH: 333
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 45

| | | | | | |
|---|---|---|---|---|---|
| acacgtgttg | atcagacacc | gcgtaccgca | accaaagaaa | ccggtgaaag | cctgaccatt | 60 |
| aattgtgttc | tgaccgatac | cgggtatggt | ttggctgcca | ccagctggtt | tcgtaaaaat | 120 |
| ccgggtacaa | ccgattggga | acgtatgagc | attggtggtc | gttatgttga | aagcgtgaat | 180 |
| aaaggtgcca | aaagctttag | cctgcgcatt | aaagatctga | ccgttgcaga | tagcgcaacc | 240 |
| tattactgta | aagcatggtg | ggacgttccg | cagcgttggg | aaccggtttc | taactactgg | 300 |
| tatgatggtg | caggcaccgt | tctgaccgtt | aat | | | 333 |

<210> SEQ ID NO 46
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 46

```
acacgtgttg atcagacacc gcgtaccgca accaaagaaa ccggtgaaag cctgaccatt    60
aattgtgttc tgaccgatac ctctccgact ggtactttca ccagctggtt tcgtaaaaat   120
ccgggtacaa ccgattggga acgtatgagc attggtggtc gttatgttga aagcgtgaat   180
aaaggtgcca aaagctttag cctgcgcatt aaagatctga ccgttgcaga tagcgcaacc   240
tatatctgtc gtgccccgta ctaccagtac aacgactggc atgatgttta tggtgcaggc   300
accgttctga ccgttaat                                                 318

<210> SEQ ID NO 47
<211> LENGTH: 327
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 47
acacgtgttg atcagacacc gcgtaccgca accaaagaaa ccggtgaaag cctgaccatt    60
aattgtgttc tgaccgatac ctggactact tgggttggta ccagctggtt tcgtaaaaat   120
ccgggtacaa ccgattggga acgtatgagc attggtggtc gttatgttga aagcgtgaat   180
aaaggtgcca aaagctttag cctgcgcatt aaagatctga ccgttgcaga tagcgcaacc   240
tattactgta aagcacagac tccgtggtgg atgcagtggc atctgtctat gtggtatgat   300
ggtgcaggca ccgttctgac cgttaac                                       327

<210> SEQ ID NO 48
<211> LENGTH: 333
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 48
acacgtgttg atcagacacc gcgtaccgca accaaagaaa ccggtgaaag cctgaccatt    60
aattgtgttc tgaccgatac cgattatggt ttgttctcca ccagctggtt tcgtaaaaat   120
ccgggtacaa ccgattggga acgtatgagc attggtggtc gttatgttga aagcgtgaat   180
aaaggtgcca aaagctttag cctgcgcatt aaagatctga ccgttgcaga tagcgcaacc   240
tattactgta aagcattcac ttggccgtgg gaatggccgg accgttggtt ccgtccgtgg   300
tatgatggtg caggcaccgt tctgaccgtt aat                                333

<210> SEQ ID NO 49
<211> LENGTH: 327
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 49
acacgtgttg atcagacacc gcgtaccgca accaaagaaa ccggtgaaag cctgaccatt    60
aattgtgttc tgaccgatac caattatgct tggttctcca ccagctggtt tcgtaaaaat   120
ccgggtacaa ccgattggga acgtatgagc attggtggtc gttatgttga aagcgtgaat   180
aaaggtgcca aaagctttag cctgcgcatt aaagatctga ccgttgcaga tagcgcaacc   240
tattactgta aagcactgta cccggggttgg aaatggccgt ggcataactt ctggtatgat   300
```

```
ggtgcaggca ccgttctgac cgttaat                                          327

<210> SEQ ID NO 50
<211> LENGTH: 324
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 50
gcaagcgtta atcagacacc gcgtaccgca accaaagaaa ccggtgaaag cctgaccatt     60
aattgtgttc tgaccgatac caggtatgct tggttctcca ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tatatctgtc gtgcccaggt tctgttcgct cagcaggctg tttggactga tgtttatggt    300
gcaggcaccg ttctgaccgt taat                                           324

<210> SEQ ID NO 51
<211> LENGTH: 321
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 51
acacgtgttg atcagacacc gcgtaccgca accaaagaaa ccggtgaaag cctgaccatt     60
aattgtgttc tgaccgatac cggttatggt tggtacgcca ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tattactgta aagcatggaa cccgtggttc cagtgggaag aactgtggta tgatggtgca    300
ggcaccgttc tgaccgttaa t                                              321

<210> SEQ ID NO 52
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 52
acacgtgttg atcagacacc gcgtaccgca accaaagaaa ccggtgaaag cctgaccatt     60
aattgtgttc tgaccgatac ctacactatc tgggttacta ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tatatctgtc gtgccctgta ctaccagtgg aaccgtcgtt tcgatgttta tggtgcaggc    300
accgttctga ccgttaat                                                  318

<210> SEQ ID NO 53
<211> LENGTH: 321
<212> TYPE: DNA
<213> ORGANISM: Artificial sequence
<220> FEATURE:
<223> OTHER INFORMATION: Synthetic sequence: Nucleic acid sequence of
``` synthetic library derived anti-hICOSL VNAR domains

<400> SEQUENCE: 53

| | | |
|---|---|---|
| gcaagcgtta atcagacacc gcgtaccgca accaaagaaa ccggtgaaag cctgaccatt | 60 |
| aattgtgttc tgaccgatac cgacgtttgg tacgaccata ccagctggtt tcgtaaaaat | 120 |
| ccgggtacaa ccgattggga acgtatgagc attggtggtc gttatgttga aagcgtgaat | 180 |
| aaaggtgcca aaagctttag cctgcgcatt aaagatctga ccgttgcaga tagcgcaacc | 240 |
| tattactgta aagcacaggt tctgtctatg tggggtaaat ggcagtggta tgatggtgca | 300 |
| ggcaccgttc tgaccgttaa t | 321 |

<210> SEQ ID NO 54
<211> LENGTH: 333
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 54

| | | |
|---|---|---|
| acacgtgttg atcagacacc gcgtaccgca accaaagaaa ccggtgaaag cctgaccatt | 60 |
| aattgtgttc tgaccgatac cagttatggt ttgttcgcca ccagctggtt tcgtaaaaat | 120 |
| ccgggtacaa ccgattggga acgtatgagc attggtggtc gttatgttga aagcgtgaat | 180 |
| aaaggtgcca aaagctttag cctgcgcatt aaagatctga ccgttgcaga tagcgcaacc | 240 |
| tattactgta aagcatggtc ttacccgctg gaactgccga acggtcgttt caaaccgtgg | 300 |
| tatgatggtg caggcaccgt tctgaccgtt aat | 333 |

<210> SEQ ID NO 55
<211> LENGTH: 315
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 55

| | | |
|---|---|---|
| acacgtgttg atcagacacc gcgtaccgca accaaagaaa ccggtgaaag cctgaccatt | 60 |
| aattgtgttt taccggtgc agattatggt ttgttcgcca cctattggta tcgtaaaaat | 120 |
| ccgggtagca gcaatcagga acgtattagc attagcggtc gttatgttga aagcgtgaat | 180 |
| aaacgcacca tgagctttag cctgcgtatt aaagatctga ccgttgcaga tagcgcaacc | 240 |
| tattactgta aagcacatat cccgtggact gaagcttact ggtatgatgg tgcaggcacc | 300 |
| gttctgaccg ttaat | 315 |

<210> SEQ ID NO 56
<211> LENGTH: 333
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 56

| | | |
|---|---|---|
| gcaagcgtta atcagacacc gcgtaccgca accaaagaaa ccggtgaaag cctgaccatt | 60 |
| aattgtgttc tgaccgatac cggttatggt ttggctgcca ccagctggtt tcgtaaaaat | 120 |
| ccgggtacaa ccgattggga acgtatgagc attggtggtc gttatgttga aagcgtgaat | 180 |

```
aaaggtgcca aaagctttag cctgcgcatt aaagatctga ccgttgcaga tagcgcaacc    240
tattactgta aagcatgggt taacttcccg cagtacatgt ggaactcttg gatcccgtgg    300
tatgatggtg caggcaccgt tctgaccgtt aat                                 333
```

```
<210> SEQ ID NO 57
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 57
acacgtgttg atcagacacc gcgtaccgca accaaagaaa ccggtgaaag cctgaccatt    60
aattgtgttt taccggtgc aaagtatggt tggtactcca cctattggta tcgtaaaaat    120
ccgggtagca gcaatcagga acgtattagc attagcggtc gttatgttga aagcgtgaat    180
aaacgcacca tgagctttag cctgcgtatt aaagatctga ccgttgcaga tagcgcaacc    240
tatatctgtc gtgccggtcc gccggttccg tctggtggtc tggatgttta tggtgcaggc    300
accgttctga ccgttaat                                                  318
```

```
<210> SEQ ID NO 58
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 58
acacgtgttg atcagacacc gcgtaccgca accaaagaaa ccggtgaaag cctgaccatt    60
aattgtgttc tgaccgatac cagttatgct ttgtactcca ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tatatctgtc gtgccttcaa catcggtgtt tggccgtggg ctgatgttta tggtgcaggc    300
accgttctga ccgttaat                                                  318
```

```
<210> SEQ ID NO 59
<211> LENGTH: 324
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 59
acacgtgttg atcagacacc gcgtaccgca accaaagaaa ccggtgaaag cctgaccatt    60
aattgtgttc tgaccgatac cggttatggt tggttctcca ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tatatctgtc gtgcctggaa actggaaccg cattctgctc agtggcagga tgtttatggt    300
gcaggcaccg ttctgaccgt taat                                           324
```

```
<210> SEQ ID NO 60
<211> LENGTH: 324
<212> TYPE: DNA
```

<213> ORGANISM: Artificial sequence
<220> FEATURE:
<223> OTHER INFORMATION: Synthetic sequence: Nucleic acid sequence of synthetic library derived anti-hICOSL VNAR domains

<400> SEQUENCE: 60

```
acacgtgttg atcagacacc gcgtaccgca accaaagaaa ccggtgaaag cctgaccatt      60
aattgtgttc tgaccgatac cgttaaaact ccgtgggaaa ccagctggtt tcgtaaaaat     120
ccgggtacaa ccgattggga acgtatgagc attggtggtc gttatgttga aagcgtgaat     180
aaaggtgcca aaagctttag cctgcgcatt aaagatctga ccgttgcaga tagcgcaacc     240
tatatctgtc gtgccgacaa cttcccgtgg atgtgggttc aggctctgga tgtttatggt     300
gcaggcaccg ttctgaccgt taat                                            324
```

<210> SEQ ID NO 61
<211> LENGTH: 318
<212> TYPE: DNA
<213> ORGANISM: Artificial sequence
<220> FEATURE:
<223> OTHER INFORMATION: Synthetic sequence: Nucleic acid sequence of synthetic library derived anti-hICOSL VNAR domains

<400> SEQUENCE: 61

```
acacgtgttg atcagacacc gcgtaccgca accaaagaaa ccggtgaaag cctgaccatt      60
aattgtgttc tgaccgatac cctgggttac tggtggcata ccagctggtt tcgtaaaaat     120
ccgggtacaa ccgattggga acgtatgagc attggtggtc gttatgttga aagcgtgaat     180
aaaggtgcca aaagctttag cctgcgcatt aaagatctga ccgttgcaga tagcgcaacc     240
tatatctgtc gtgcctctgg tatcgctcgt cagactcaga agatgtttta tggtgcaggc     300
accgttctga ccgttaat                                                   318
```

<210> SEQ ID NO 62
<211> LENGTH: 327
<212> TYPE: DNA
<213> ORGANISM: Artificial sequence
<220> FEATURE:
<223> OTHER INFORMATION: Synthetic sequence: Nucleic acid sequence of synthetic library derived anti-hICOSL VNAR domains

<400> SEQUENCE: 62

```
gcaagcgtta atcagacacc gcgtaccgca accaaagaaa ccggtgaaag cctgaccatt      60
aattgtgttc tgaccgatac cctgcattct tggtctacta ccagctggtt tcgtaaaaat     120
ccgggtacaa ccgattggga acgtatgagc attggtggtc gttatgttga aagcgtgaat     180
aaaggtgcca aaagctttag cctgcgcatt aaagatctga ccgttgcaga tagcgcaacc     240
tattactgta aagcattcta catgtctact ggttcttttcc cgtacccgtg gtggtatgat    300
ggtgcaggca ccgttctgac cgttaat                                         327
```

<210> SEQ ID NO 63
<211> LENGTH: 309
<212> TYPE: DNA
<213> ORGANISM: Artificial sequence
<220> FEATURE:
<223> OTHER INFORMATION: Synthetic sequence: Nucleic acid sequence of synthetic library derived anti-hICOSL VNAR domains

<400> SEQUENCE: 63

```
acacgtgttg atcagacacc gcgtaccgca accaaagaaa ccggtgaaag cctgaccatt      60
aattgtgttc tgaccgatac ctggaaacag gtttgggcta ccagctggtt tcgtaaaaat     120
```

```
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tattactgta aagcagaact gttcatctac aactggtatg atggtgcagg caccgttctg    300
accgttaat                                                            309
```

<210> SEQ ID NO 64
<211> LENGTH: 315
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 64

```
gcaagcgtta atcagacacc gcgtaccgca accaaagaaa ccggtgaaag cctgaccatt     60
aattgtgttc tgaccgatac cgaagttcat tggatgtgga ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tattactgta aagcaggttt cgcttggcat tacccgtggt ggtatgatgg tgcaggcacc    300
gttctgaccg ttaat                                                     315
```

<210> SEQ ID NO 65
<211> LENGTH: 327
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 65

```
acacgtgttg atcagacacc gcgtaccgca accaaagaaa ccggtgaaag cctgaccatt     60
aattgtgttc tgaccgatac cggatatggt ttggcttcca ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tattactgta aagcacagct gaactggtgg aaccgtcagg ctccgcgtca ttggtatgat    300
ggtgcaggca ccgttctgac cgttaat                                        327
```

<210> SEQ ID NO 66
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 66

```
acacgtgttg atcagacacc gcgtaccgca accaaagaaa ccggtgaaag cctgaccatt     60
aattgtgttc tgaccgatac ccaggaacag aacgttgcta ccagctggtt tcgtaaaaat    120
ccgggtacaa ccgattggga acgtatgagc attggtggtc gttatgttga aagcgtgaat    180
aaaggtgcca aaagctttag cctgcgcatt aaagatctga ccgttgcaga tagcgcaacc    240
tatatctgtc gtgcccagat cctggctccg ccgccgtacc aggatgttta tggtgcaggc    300
accgttctga ccgttaat                                                  318
```

```
<210> SEQ ID NO 67
<211> LENGTH: 315
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 67
gcaagcgtta atcagacacc gcgtaccgca accaaagaaa ccggtgaaag cctgaccatt      60
aattgtgttc tgaccgatac ctaccattgg tggatccaga ccagctggtt tcgtaaaaat     120
ccgggtacaa ccgattggga acgtatgagc attggtggtc gttatgttga aagcgtgaat     180
aaaggtgcca aaagctttag cctgcgcatt aaagatctga ccgttgcaga tagcgcaacc     240
tattactgta aagcaggtcc ggtttggttc catatgctgt ggtatgatgg tgcaggcacc     300
gttctgaccg ttaat                                                      315

<210> SEQ ID NO 68
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 68
acacgtgttg atcagacacc gcgtaccgca accaaagaaa ccggtgaaag cctgaccatt      60
aattgtgttc tgaccgatac ctggctgccg ttcgacacta ccagctggtt tcgtaaaaat     120
ccgggtacaa ccgattggga acgtatgagc attggtggtc gttatgttga aagcgtgaat     180
aaaggtgcca aaagctttag cctgcgcatt aaagatctga ccgttgcaga tagcgcaacc     240
tattactgta aagcacgttg gccgatcctg cagctgtggc attggtatga tggtgcaggc     300
accgttctga ccgttaat                                                   318

<210> SEQ ID NO 69
<211> LENGTH: 318
<212> TYPE: DNA
<213> ORGANISM: Artificial sequence
<220> FEATURE:
<223> OTHER INFORMATION: Synthetic sequence: Nucleic acid sequence of
      synthetic library derived anti-hICOSL VNAR domains

<400> SEQUENCE: 69
acacgtgttg atcagacacc gcgtaccgca accaaagaaa ccggtgaaag cctgaccatt      60
aattgtgttc tgaccgatac ccagcatctg tggttcgttt acaccagctg gtttcgtaaa     120
aatccgggta caaccgattg gaacgtatg agcattggtg gtcgttatgt tgaaagcgtg     180
aataaaggtg ccaaaagctt tagcctgcgc attaaagatc tgaccgttgc agatagcgca     240
acctattact gtaaagcatg gtggaacccg tactggttcc agtggtatga tggtgcaggc     300
accgttctga ccgttaat                                                   318

<210> SEQ ID NO 70
<211> LENGTH: 117
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 70
```

Ala Arg Val Asp Gln Thr Pro Arg Ser Val Thr Lys Glu Thr Gly Glu
1               5                   10                  15

Ser Leu Thr Ile Asn Cys Val Leu Arg Asp Pro Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

Tyr Arg Cys Gly Ala Thr Asp Thr Val Arg Ile Tyr Ser Cys Asp Tyr
                85                  90                  95

Leu Cys Ala Leu Asn Gly His Arg Asp Ala Ala Cys Gly Gly Gly Thr
                100                 105                 110

Val Val Thr Val Asn
            115

<210> SEQ ID NO 71
<211> LENGTH: 109
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 71

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Ala Ala Leu Val
                20                  25                  30

Arg Thr Cys Trp Ser Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

Tyr Arg Cys Gly Leu Gly Ala Phe Cys Asp Tyr Gly Cys Ala Leu Pro
                85                  90                  95

Tyr Ala Ala Cys Gly Gly Gly Thr Ala Val Thr Val Asn
                100                 105

<210> SEQ ID NO 72
<211> LENGTH: 109
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 72

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Gly Ala Ser Leu Gly
                20                  25                  30

Ser Thr Cys Trp Thr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

```
Ser Phe Ser Leu Arg Ile Asn Asp Leu Thr Val Glu Asp Gly Gly Thr
 65                  70                  75                  80

Tyr Arg Cys Ala Leu Gly Ala Phe Cys Asp Tyr Gly Cys Ala Leu Pro
                 85                  90                  95

Tyr Ala Ala Cys Gly Asp Gly Thr Ala Val Thr Val Asn
            100                 105

<210> SEQ ID NO 73
<211> LENGTH: 117
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 73

Ala Arg Val Asp Gln Thr Pro Arg Ser Val Thr Lys Glu Thr Gly Glu
 1               5                  10                  15

Ser Leu Thr Ile Asn Cys Val Leu Arg Asp Gly Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly His Phe Pro Gly Val Gly Gly Arg Ser Cys Asp Phe
                 85                  90                  95

Pro Tyr Ser Cys Ala Leu His Gly Tyr Ala Ala Cys Gly Asp Gly Thr
            100                 105                 110

Ala Val Thr Val Asn
            115

<210> SEQ ID NO 74
<211> LENGTH: 115
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 74

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Asn Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly Val Trp Arg Gly Ile Ser Pro Cys Asp Tyr Pro Tyr
                 85                  90                  95

Ser Cys Ala Leu Val Gly Tyr Ala Ala Cys Gly Asp Gly Thr Ala Val
            100                 105                 110

Thr Val Asn
            115
```

```
<210> SEQ ID NO 75
<211> LENGTH: 115
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 75

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Trp Arg Ala Gly Gly Ser Cys Asp Phe Pro Tyr
                85                  90                  95

Ser Cys Ala Leu Val Gly Tyr Ala Ala Cys Gly Asp Gly Thr Ala Val
            100                 105                 110

Thr Val Asn
        115

<210> SEQ ID NO 76
<211> LENGTH: 117
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 76

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ile Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Pro Thr Gln Phe Thr Gly Ile Lys Ser Cys Asp
                85                  90                  95

Tyr Ile His Leu Cys Ser Ser Phe Pro Ala Ala Cys Gly Asp Gly Thr
            100                 105                 110

Ala Val Thr Val Asn
        115

<210> SEQ ID NO 77
<211> LENGTH: 117
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains
```

```
<400> SEQUENCE: 77

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly His Phe Pro Gly Val Gly Gly Ser Cys Asp Phe
                85                  90                  95

Pro Tyr Ser Cys Ala Leu His Gly Tyr Ala Ala Cys Gly Asp Gly Thr
            100                 105                 110

Ala Val Thr Val Asn
        115

<210> SEQ ID NO 78
<211> LENGTH: 117
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 78

Ala Arg Val Asp Gln Thr Pro Arg Ser Val Thr Lys Glu Thr Gly Glu
1               5                   10                  15

Ser Leu Thr Ile Asn Cys Val Leu Arg Glu Ser Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Ser Asp Leu Thr Val Glu Asp Gly Gly Thr
65                  70                  75                  80

Tyr Arg Cys Gly His Phe Pro Gly Val Gly Gly Arg Ser Cys Asp Phe
                85                  90                  95

Pro Tyr Ser Cys Ala Leu His Gly Tyr Ala Ala Cys Gly Asp Gly Thr
            100                 105                 110

Ala Val Thr Val Asn
        115

<210> SEQ ID NO 79
<211> LENGTH: 117
<212> TYPE: PRT
<213> ORGANISM: Artificial sequence
<220> FEATURE:
<223> OTHER INFORMATION: Synthetic sequence: Amino acid sequence of the
      immunized-library derived anti-hICOSL VNAR domains

<400> SEQUENCE: 79

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Arg Gly Glu Leu Gly
            20                  25                  30

Ser Thr Cys Trp Tyr Arg Lys Lys Ser Gly Ser Thr Asn Glu Glu Ser
```

```
                35                  40                  45
Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Glu Asp Gly Gly Thr
65                  70                  75                  80

Tyr Arg Cys Gly Val Pro Thr Pro Phe Thr Gly Ile Lys Ser Cys Asp
                85                  90                  95

Tyr Ile His Leu Cys Ser Arg Phe Pro Ala Ala Cys Gly Gly Gly Thr
                100                 105                 110

Val Val Thr Val Asn
        115

<210> SEQ ID NO 80
<211> LENGTH: 351
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 80
gctcgagtgg accaaacacc gagatcagta acaaaggaga cgggcgaatc actgaccatc      60
aactgtgtcc tacgagatcc gagctatgca ttgggcagca cgtgctggta tcgaaaaaaa     120
tcgggctcaa caaacgagga gagcatatcg aaaggtggac gatatgttga acagttaac     180 agcggatcaa agtccttttc tttgagaatt aatgatctaa cagttgaaga cggtggcacg     240
tatcgttgcg gtgccaccga tacggtgaga atatatagct gtgactatct ctgtgctctt     300
aacggacatc gcgatgctgc atgcggaggt ggcactgtcg tgactgtgaa t              351

<210> SEQ ID NO 81
<211> LENGTH: 327
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 81
gctcgagtgg accaaacacc gagatcagta acaaaggaga cgggcgaatc actgaccatc      60
aactgtgtcc tacgagatgc gagcgcagca ttggtacgca cgtgctggtc tcgaaaaaaa     120
tcgggctcaa caaacgagga gagcatatcg aaaggtggac gatatgttga acagttaac     180 agcggatcaa agtccttttc tttgagaatt aatgatctaa cagttgaaga cggtggcacg     240
tatcgttgcg gtttgggtgc tttctgtgac tacggctgtg ctcttcccta tgctgcatgc     300
ggaggtggca ctgccgtgac tgtgaat                                         327

<210> SEQ ID NO 82
<211> LENGTH: 327
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 82
gctcgagtgg accaaacacc gagatcagta acaaaggaga cgggcgaatc actgaccatc      60
aactgtgtcc tacgagatgc gggcgcatca ttgggcagca cgtgctggac tcgaaaaaaa     120
tcgggctcaa caaacgagga gagcatatcg aaaggtggac gatatgttga acagttaac     180
```
agcggatcaa agtccttttc tttgagaatt aatgatctaa cagttgaaga cggtggcacg    240
tatcgttgcg ccctgggtgc tttctgtgac tacggctgtg ctcttcccta tgctgcatgc    300
ggagatggca ctgccgtgac tgtgaat                                         327

<210> SEQ ID NO 83
<211> LENGTH: 351
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 83
gctcgagtgg accaaacacc gagatcagta acaaaggaga cgggcgaatc actgaccatc    60
aactgtgtcc ttcgagatgg gagttatgca ttgggcagca cgtgctggta tcgaaaaaaa    120
tcgggctcaa caaacgagga gagcatatcg aaaggtggac gatatgttga aacagttaac    180
agcggatcaa agtccttttc tttgagaatt aatgatctaa cagttgaaga cggtggcacg    240
tatcgttgcg gtcactttcc tggtgtgggg gggcggagct gtgactttcc ctacagctgt    300
gctcttcacg gctatgctgc atgcggagac ggcacagccg tgactgtgaa t              351

<210> SEQ ID NO 84
<211> LENGTH: 345
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 84
gctcgagtgg accaaacacc gagatcagta acaaaggaga cgggcgaatc actgaccatc    60
aactgtgtcc tacgagatgc gaactatgca ttgggcagca cgtgctggta tcgaaaaaaa    120
tcgggctcaa caaacgagga gagcatatcg aaaggtggac gatatgttga aacagttaac    180
agcggatcaa agtccttttc tttgagaatt aatgatctaa cagttgaaga cggtggcacg    240
tatcgttgcg gtgtctggcg ggggatctcc ccatgtgact acccatacag ctgtgctctt    300
gtaggctatg ctgcatgcgg agatggcact gccgtgactg tgaat                     345

<210> SEQ ID NO 85
<211> LENGTH: 345
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 85
gctcgagtgg accaaacacc gagatcagta acaaaggaga cgggcgaatc actgaccatc    60
aactgtgtcc tacgagatgc gagctatgca ttgggcagca cgtgctggta tcgaaaaaaa    120
tcgggctcaa caaacgagga gagcatatcg aaaggtggac gatatgttga aacagttaac    180
agcggatcaa agtccttttc tttgagaatt aatgatctaa cagttgaaga cggtggcacg    240
tatcgttgcg gtgtctggcg ggctggcgga agctgtgact ttccatatag ctgtgctctt    300
gtaggctatg ctgcatgcgg agatggcact gccgtgactg tgaat                     345

<210> SEQ ID NO 86
<211> LENGTH: 351

<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 86
gctcgagtgg accaaacacc gagatcagta acaaaggaga cgggcgaatc actgaccatc       60
aactgtgtcc tacgagatgc gatctatgca ttgggcagca cgtgctggta tcgaaaaaaa      120
tcgggctcaa caaacgagga gagcatatcg aaaggtggac gatatgttga aacagttaac      180
agcggatcaa agtcctttc tttgagaatt aatgatctaa cagttgaaga cggtggcacg       240
tatcgttgcg gtgtccccac ccaatttacg gggataaaga gctgtgacta catccatctg      300
tgctcttcct tccctgctgc atgcggagat ggcactgccg tgactgtgaa t               351

<210> SEQ ID NO 87
<211> LENGTH: 351
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 87
gctcgagtgg accaaacacc gagatcagta acaaaggaga cgggcgaatc actgaccatc       60
aactgtgtcc tacgagatgc gagctatgca ttgggcagca cgtgctggta tcgaaaaaaa      120
tcgggctcaa caaacgagga gagcatatcg aaaggtggac gatatgttga aacagttaac      180
agcggatcaa agtcctttc tttgagaatt aatgatctaa cagttgaaga cggtggcacg       240
tatcgttgcg gtcactttcc tggtgtgggg gggggagct gtgactttcc ctacagctgt       300
gctcttcacg gctatgctgc atgcggagat ggcactgccg tgactgtgaa t               351

<210> SEQ ID NO 88
<211> LENGTH: 351
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 88
gctcgagtgg accaaacacc gagatcagta acaaaggaga cgggcgaatc actgaccatc       60
aactgtgtcc tacgagaatc gagctatgca ttgggcagca cgtgctggta tcgaaaaaaa      120
tcgggctcaa caaacgagga gagcatatcg aaaggtggac gatatgttga aacagttaac      180
agcggatcaa agtcctttc tttgagaatt agtgatctaa cagttgaaga cggtggcacg       240
tatcgttgcg gtcactttcc tggtgtgggg ggccggagct gtgactttcc ctacagctgt      300
gctcttcacg gctatgctgc atgcggagat ggcactgccg tgactgtgaa t               351

<210> SEQ ID NO 89
<211> LENGTH: 351
<212> TYPE: DNA
<213> ORGANISM: Artificial sequence
<220> FEATURE:
<223> OTHER INFORMATION: Synthetic sequence: Nucleic acid sequence of
      the immunized-library derived anti-hICOSL VNAR domains

<400> SEQUENCE: 89
gctcgagtgg accaaacacc gagatcagta acaaaggaga cgggcgaatc actgaccatc       60

```
aactgtgtcc tacgagatgc gagaggtgaa ttgggcagca cgtgctggta tcgaaaaaaa    120
tcgggctcaa caaacgagga gagcatatcg aaaggtggac gatatgttga aacagttaac    180
agcggatcaa agtcctttc tttgagaatt aatgatctaa cagttgaaga cggtggcacg    240
tatcgttgcg gtgtccccac cccgtttacg gggataaaga gctgtgacta catccatctg    300
tgctctcgat tccctgctgc atgcggaggt ggcactgtcg tgactgtgaa t             351
```

```
<210> SEQ ID NO 90
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 90

Trp Lys Trp Trp Leu Gln
1               5

<210> SEQ ID NO 91
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 91

Pro Gln Asn Trp Gln Ala
1               5

<210> SEQ ID NO 92
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 92

Gly Tyr Gly Leu Ala Ala
1               5

<210> SEQ ID NO 93
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 93

Ser Pro Thr Gly Thr Phe
1               5

<210> SEQ ID NO 94
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 94

Trp Thr Thr Trp Val Gly
1               5

<210> SEQ ID NO 95
<211> LENGTH: 6
<212> TYPE: PRT
```

<213> ORGANISM: Artificial sequence
<220> FEATURE:
<223> OTHER INFORMATION: Synthetic sequence: CDR1 domain

<400> SEQUENCE: 95

Asp Tyr Gly Leu Phe Ser
1               5

<210> SEQ ID NO 96
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 96

Asn Tyr Ala Trp Phe Ser
1               5

<210> SEQ ID NO 97
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 97

Arg Tyr Ala Trp Phe Ser
1               5

<210> SEQ ID NO 98
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 98

Gly Tyr Gly Trp Tyr Ala
1               5

<210> SEQ ID NO 99
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 99

Tyr Thr Ile Trp Val Thr
1               5

<210> SEQ ID NO 100
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 100

Asp Val Trp Tyr Asp His
1               5

<210> SEQ ID NO 101
<211> LENGTH: 6
<212> TYPE: PRT
<213> ORGANISM: Artificial sequence

```
<220> FEATURE:
<223> OTHER INFORMATION: Synthetic sequence: CDR1 domain

<400> SEQUENCE: 101

Ser Tyr Gly Leu Phe Ala
1               5

<210> SEQ ID NO 102
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 102

Asp Tyr Gly Leu Phe Ala
1               5

<210> SEQ ID NO 103
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 103

Gly Tyr Gly Leu Ala Ala
1               5

<210> SEQ ID NO 104
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 104

Lys Tyr Gly Trp Tyr Ser
1               5

<210> SEQ ID NO 105
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 105

Ser Tyr Ala Leu Tyr Ser
1               5

<210> SEQ ID NO 106
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 106

Gly Tyr Gly Trp Phe Ser
1               5

<210> SEQ ID NO 107
<211> LENGTH: 6
<212> TYPE: PRT
<213> ORGANISM: Artificial sequence
<220> FEATURE:
```

```
<223> OTHER INFORMATION: Synthetic sequence: CDR1 domain

<400> SEQUENCE: 107

Val Lys Thr Pro Trp Glu
1               5

<210> SEQ ID NO 108
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 108

Leu Gly Tyr Trp Trp His
1               5

<210> SEQ ID NO 109
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 109

Leu His Ser Trp Ser Thr
1               5

<210> SEQ ID NO 110
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 110

Trp Lys Gln Val Trp Ala
1               5

<210> SEQ ID NO 111
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 111

Glu Val His Trp Met Trp
1               5

<210> SEQ ID NO 112
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 112

Gly Tyr Gly Leu Ala Ser
1               5

<210> SEQ ID NO 113
<211> LENGTH: 6
<212> TYPE: PRT
<213> ORGANISM: Artificial sequence
<220> FEATURE:
<223> OTHER INFORMATION: Synthetic sequence: CDR1 domain
```

<210> SEQ ID NO 114
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 114

Tyr His Trp Trp Ile Gln
1               5

<210> SEQ ID NO 115
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 115

Trp Leu Pro Phe Asp Thr
1               5

<210> SEQ ID NO 116
<211> LENGTH: 7
<212> TYPE: PRT
<213> ORGANISM: Artificial sequence
<220> FEATURE:
<223> OTHER INFORMATION: Synthetic sequence: CDR1 domain

<400> SEQUENCE: 116

Gln His Leu Trp Phe Val Tyr
1               5

<210> SEQ ID NO 117
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 117

Gly Pro Ile Tyr Phe Glu Thr Trp His Asp Val
1               5                   10

<210> SEQ ID NO 118
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 118

Val Phe Leu Asn Pro Trp Asp Trp Pro His Trp Tyr
1               5                   10

<210> SEQ ID NO 119
<211> LENGTH: 16
<212> TYPE: PRT
<213> ORGANISM: Artificial sequence
<220> FEATURE:
<223> OTHER INFORMATION: Synthetic sequence: CDR3 domain

<400> SEQUENCE: 113

Gln Glu Gln Asn Val Ala
1               5

```
<400> SEQUENCE: 119

Trp Trp Asp Val Pro Gln Arg Trp Glu Pro Val Ser Asn Tyr Trp Tyr
1               5                   10                  15

<210> SEQ ID NO 120
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 120

Pro Tyr Tyr Gln Tyr Asn Asp Trp His Asp Val
1               5                   10

<210> SEQ ID NO 121
<211> LENGTH: 14
<212> TYPE: PRT
<213> ORGANISM: Artificial sequence
<220> FEATURE:
<223> OTHER INFORMATION: Synthetic sequence: CDR3 domain

<400> SEQUENCE: 121

Gln Thr Pro Trp Trp Met Gln Trp His Leu Ser Met Trp Tyr
1               5                   10

<210> SEQ ID NO 122
<211> LENGTH: 16
<212> TYPE: PRT
<213> ORGANISM: Artificial sequence
<220> FEATURE:
<223> OTHER INFORMATION: Synthetic sequence: CDR3 domain

<400> SEQUENCE: 122

Phe Thr Trp Pro Trp Glu Trp Pro Asp Arg Trp Phe Arg Pro Trp Tyr
1               5                   10                  15

<210> SEQ ID NO 123
<211> LENGTH: 14
<212> TYPE: PRT
<213> ORGANISM: Artificial sequence
<220> FEATURE:
<223> OTHER INFORMATION: Synthetic sequence: CDR3 domain

<400> SEQUENCE: 123

Leu Tyr Pro Gly Trp Lys Trp Pro Trp His Asn Phe Trp Tyr
1               5                   10

<210> SEQ ID NO 124
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 124

Gln Val Leu Phe Ala Gln Gln Ala Val Trp Thr Asp Val
1               5                   10

<210> SEQ ID NO 125
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 125
```

Trp Asn Pro Trp Phe Gln Trp Glu Glu Leu Trp Tyr
1               5                   10

<210> SEQ ID NO 126
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 126

Leu Tyr Tyr Gln Trp Asn Arg Arg Phe Asp Val
1               5                   10

<210> SEQ ID NO 127
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 127

Gln Val Leu Ser Met Trp Gly Lys Trp Gln Trp Tyr
1               5                   10

<210> SEQ ID NO 128
<211> LENGTH: 16
<212> TYPE: PRT
<213> ORGANISM: Artificial sequence
<220> FEATURE:
<223> OTHER INFORMATION: Synthetic sequence: CDR3 domain

<400> SEQUENCE: 128

Trp Ser Tyr Pro Leu Glu Leu Pro Asn Gly Arg Phe Lys Pro Trp Tyr
1               5                   10                  15

<210> SEQ ID NO 129
<211> LENGTH: 10
<212> TYPE: PRT
<213> ORGANISM: Artificial sequence
<220> FEATURE:
<223> OTHER INFORMATION: Synthetic sequence: CDR3 domain

<400> SEQUENCE: 129

His Ile Pro Trp Thr Glu Ala Tyr Trp Tyr
1               5                   10

<210> SEQ ID NO 130
<211> LENGTH: 16
<212> TYPE: PRT
<213> ORGANISM: Artificial sequence
<220> FEATURE:
<223> OTHER INFORMATION: Synthetic sequence: CDR3 domain

<400> SEQUENCE: 130

Trp Val Asn Phe Pro Gln Tyr Met Trp Asn Ser Trp Ile Pro Trp Tyr
1               5                   10                  15

<210> SEQ ID NO 131
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 131

```
Gly Pro Pro Val Pro Ser Gly Gly Leu Asp Val
1               5                   10
```

<210> SEQ ID NO 132
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 132

```
Phe Asn Ile Gly Val Trp Pro Trp Ala Asp Val
1               5                   10
```

<210> SEQ ID NO 133
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 133

```
Trp Lys Leu Glu Pro His Ser Ala Gln Trp Gln Asp Val
1               5                   10
```

<210> SEQ ID NO 134
<211> LENGTH: 12
<212> TYPE: PRT
<213> ORGANISM: Artificial sequence
<220> FEATURE:
<223> OTHER INFORMATION: Synthetic sequence: CDR3 domain

<400> SEQUENCE: 134

```
Asn Phe Pro Trp Met Trp Val Gln Ala Leu Asp Val
1               5                   10
```

<210> SEQ ID NO 135
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 135

```
Ser Gly Ile Ala Arg Gln Thr Gln Lys Asp Val
1               5                   10
```

<210> SEQ ID NO 136
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 136

```
Phe Tyr Met Ser Thr Gly Ser Phe Pro Tyr Pro Trp Trp
1               5                   10
```

<210> SEQ ID NO 137
<211> LENGTH: 7
<212> TYPE: PRT
<213> ORGANISM: Artificial sequence
<220> FEATURE:
<223> OTHER INFORMATION: Synthetic sequence: CDR3 domain

<400> SEQUENCE: 137

```
Glu Leu Phe Ile Tyr Asn Trp
```

```
1               5
```

<210> SEQ ID NO 138
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 138

```
Gly Phe Ala Trp His Tyr Pro Trp Trp
1               5
```

<210> SEQ ID NO 139
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 139

```
Gln Leu Asn Trp Trp Asn Arg Gln Ala Pro Arg His Trp
1               5                   10
```

<210> SEQ ID NO 140
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 140

```
Gln Ile Leu Ala Pro Pro Tyr Gln Asp Val
1               5                   10
```

<210> SEQ ID NO 141
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 141

```
Gly Pro Val Trp Phe His Met Leu Trp
1               5
```

<210> SEQ ID NO 142
<211> LENGTH: 10
<212> TYPE: PRT
<213> ORGANISM: Artificial sequence
<220> FEATURE:
<223> OTHER INFORMATION: Synthetic sequence: CDR3 domain

<400> SEQUENCE: 142

```
Arg Trp Pro Ile Leu Gln Leu Trp His Trp
1               5                   10
```

<210> SEQ ID NO 143
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 143

```
Trp Trp Asn Pro Tyr Trp Phe Gln Trp
1               5
```

<210> SEQ ID NO 144
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 144

Ser Tyr Ala Leu Gly Ser
1               5

<210> SEQ ID NO 145
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 145

Ser Ala Ala Leu Val Arg
1               5

<210> SEQ ID NO 146
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 146

Gly Ala Ser Leu Gly Ser
1               5

<210> SEQ ID NO 147
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 147

Asn Tyr Ala Leu Gly Ser
1               5

<210> SEQ ID NO 148
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 148

Ile Tyr Ala Leu Gly Ser
1               5

<210> SEQ ID NO 149
<211> LENGTH: 6
<212> TYPE: PRT
<213> ORGANISM: Artificial sequence
<220> FEATURE:
<223> OTHER INFORMATION: Synthetic sequence: CDR1 domain

<400> SEQUENCE: 149

Arg Gly Glu Leu Gly Ser
1               5

<210> SEQ ID NO 150
<211> LENGTH: 22
<212> TYPE: PRT
<213> ORGANISM: Artificial sequence
<220> FEATURE:
<223> OTHER INFORMATION: Synthetic sequence: CDR3 domain

<400> SEQUENCE: 150

Thr Asp Thr Val Arg Ile Tyr Ser Cys Asp Tyr Leu Cys Ala Leu Asn
1               5                   10                  15

Gly His Arg Asp Ala Ala
            20

<210> SEQ ID NO 151
<211> LENGTH: 14
<212> TYPE: PRT
<213> ORGANISM: Artificial sequence
<220> FEATURE:
<223> OTHER INFORMATION: Synthetic sequence: CDR3 domain

<400> SEQUENCE: 151

Gly Ala Phe Cys Asp Tyr Gly Cys Ala Leu Pro Tyr Ala Ala
1               5                   10

<210> SEQ ID NO 152
<211> LENGTH: 22
<212> TYPE: PRT
<213> ORGANISM: Artificial sequence
<220> FEATURE:
<223> OTHER INFORMATION: Synthetic sequence: CDR3 domain

<400> SEQUENCE: 152

Phe Pro Gly Val Gly Gly Arg Ser Cys Asp Phe Pro Tyr Ser Cys Ala
1               5                   10                  15

Leu His Gly Tyr Ala Ala
            20

<210> SEQ ID NO 153
<211> LENGTH: 20
<212> TYPE: PRT
<213> ORGANISM: Artificial sequence
<220> FEATURE:
<223> OTHER INFORMATION: Synthetic sequence: CDR3 domain

<400> SEQUENCE: 153

Trp Arg Gly Ile Ser Pro Cys Asp Tyr Pro Tyr Ser Cys Ala Leu Val
1               5                   10                  15

Gly Tyr Ala Ala
            20

<210> SEQ ID NO 154
<211> LENGTH: 20
<212> TYPE: PRT
<213> ORGANISM: Artificial sequence
<220> FEATURE:
<223> OTHER INFORMATION: Synthetic sequence: CDR3 domain

<400> SEQUENCE: 154

Trp Arg Ala Gly Gly Ser Cys Asp Phe Pro Tyr Ser Cys Ala Leu Val
1               5                   10                  15

Gly Tyr Ala Ala
            20

<210> SEQ ID NO 155

```
<211> LENGTH: 22
<212> TYPE: PRT
<213> ORGANISM: Artificial sequence
<220> FEATURE:
<223> OTHER INFORMATION: Synthetic sequence: CDR3 domain

<400> SEQUENCE: 155

Pro Thr Gln Phe Thr Gly Ile Lys Ser Cys Asp Tyr Ile His Leu Cys
1               5                   10                  15

Ser Ser Phe Pro Ala Ala
            20

<210> SEQ ID NO 156
<211> LENGTH: 22
<212> TYPE: PRT
<213> ORGANISM: Artificial sequence
<220> FEATURE:
<223> OTHER INFORMATION: Synthetic sequence: CDR3 domain

<400> SEQUENCE: 156

Phe Pro Gly Val Gly Gly Gly Ser Cys Asp Phe Pro Tyr Ser Cys Ala
1               5                   10                  15

Leu His Gly Tyr Ala Ala
            20

<210> SEQ ID NO 157
<211> LENGTH: 22
<212> TYPE: PRT
<213> ORGANISM: Artificial sequence
<220> FEATURE:
<223> OTHER INFORMATION: Synthetic sequence: CDR3 domain

<400> SEQUENCE: 157

Phe Pro Gly Val Gly Gly Arg Ser Cys Asp Phe Pro Tyr Ser Cys Ala
1               5                   10                  15

Leu His Gly Tyr Ala Ala
            20

<210> SEQ ID NO 158
<211> LENGTH: 22
<212> TYPE: PRT
<213> ORGANISM: Artificial sequence
<220> FEATURE:
<223> OTHER INFORMATION: Synthetic sequence: CDR3 domain

<400> SEQUENCE: 158

Pro Thr Pro Phe Thr Gly Ile Lys Ser Cys Asp Tyr Ile His Leu Cys
1               5                   10                  15

Ser Arg Phe Pro Ala Ala
            20

<210> SEQ ID NO 159
<211> LENGTH: 17
<212> TYPE: PRT
<213> ORGANISM: Artificial sequence
<220> FEATURE:
<223> OTHER INFORMATION: Synthetic sequence: CDR3 domain

<400> SEQUENCE: 159

Cys Val Phe Met Gly Ile Asp Trp Arg Leu Gly Gln Leu Tyr Trp Asp
1               5                   10                  15

Val

<210> SEQ ID NO 160
```

```
<211> LENGTH: 13
<212> TYPE: PRT
<213> ORGANISM: Artificial sequence
<220> FEATURE:
<223> OTHER INFORMATION: Synthetic sequence: CDR3 domain

<400> SEQUENCE: 160

Gln Ala Leu Ile Ile Val Asp Phe Gln Ala Leu Asp Val
1               5                   10

<210> SEQ ID NO 161
<211> LENGTH: 15
<212> TYPE: PRT
<213> ORGANISM: Artificial sequence
<220> FEATURE:
<223> OTHER INFORMATION: Synthetic sequence: CDR3 domain

<400> SEQUENCE: 161

Val Gly Tyr Asp Thr Gly Phe Val Gly Arg Arg Glu Ser Asp Val
1               5                   10                  15

<210> SEQ ID NO 162
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 162

Trp Glu Arg Leu Val Met Pro Glu Asp Asp Val
1               5                   10

<210> SEQ ID NO 163
<211> LENGTH: 10
<212> TYPE: PRT
<213> ORGANISM: Artificial sequence
<220> FEATURE:
<223> OTHER INFORMATION: Synthetic sequence: CDR3 domain

<400> SEQUENCE: 163

Arg Cys Phe Leu Phe Gln Ile Asp Asp Val
1               5                   10

<210> SEQ ID NO 164
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 164

Gly Ser Lys Gly Lys Gly Phe Asp Val
1               5

<210> SEQ ID NO 165
<211> LENGTH: 15
<212> TYPE: PRT
<213> ORGANISM: Artificial sequence
<220> FEATURE:
<223> OTHER INFORMATION: Synthetic sequence: CDR3 domain

<400> SEQUENCE: 165

Thr Leu Cys Ala Ser Ser His Met Gly Asn Val Val Ala Asp Val
1               5                   10                  15

<210> SEQ ID NO 166
<211> LENGTH: 13
```

<212> TYPE: PRT
<213> ORGANISM: Artificial sequence
<220> FEATURE:
<223> OTHER INFORMATION: Synthetic sequence: CDR3 domain

<400> SEQUENCE: 166

Val His Leu Phe Asn Pro Ile Phe His Met His Asp Val
1               5                   10

<210> SEQ ID NO 167
<211> LENGTH: 17
<212> TYPE: PRT
<213> ORGANISM: Artificial sequence
<220> FEATURE:
<223> OTHER INFORMATION: Synthetic sequence: CDR3 domain

<400> SEQUENCE: 167

Thr Asn Pro Ser Gly His Leu Trp Phe Tyr Arg Arg Leu Phe Tyr Asp
1               5                   10                  15
Val

<210> SEQ ID NO 168
<211> LENGTH: 11
<212> TYPE: PRT
<213> ORGANISM: Artificial sequence
<220> FEATURE:
<223> OTHER INFORMATION: Synthetic sequence: CDR3 domain

<400> SEQUENCE: 168

Lys Trp Arg Pro Pro Leu Gln Glu Gln Asp Val
1               5                   10

<210> SEQ ID NO 169
<211> LENGTH: 9
<212> TYPE: PRT
<213> ORGANISM: Artificial sequence
<220> FEATURE:
<223> OTHER INFORMATION: Synthetic sequence: CDR3 domain

<400> SEQUENCE: 169

Ile Cys His Gln Ser Asn Val Asp Val
1               5

<210> SEQ ID NO 170
<211> LENGTH: 16
<212> TYPE: PRT
<213> ORGANISM: Artificial sequence
<220> FEATURE:
<223> OTHER INFORMATION: Synthetic linker

<400> SEQUENCE: 170

Gly Gly Gly Ser Gly Gly Gly Ser Gly Gly Gly Ser Gly Gly Gly Ser
1               5                   10                  15

<210> SEQ ID NO 171
<211> LENGTH: 302
<212> TYPE: PRT
<213> ORGANISM: Homo sapiens

<400> SEQUENCE: 171

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
                20                  25                  30

Val Glu Leu Ser Cys Ala Cys Pro Glu Gly Ser Arg Phe Asp Leu Asn

```
            35                  40                  45
Asp Val Tyr Val Tyr Trp Gln Thr Ser Glu Ser Lys Thr Val Val Thr
 50                  55                  60

Tyr His Ile Pro Gln Asn Ser Ser Leu Glu Asn Val Asp Ser Arg Tyr
 65                  70                  75                  80

Arg Asn Arg Ala Leu Met Ser Pro Ala Gly Met Leu Arg Gly Asp Phe
                 85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300

<210> SEQ ID NO 172
<211> LENGTH: 322
<212> TYPE: PRT
<213> ORGANISM: Mus musculus

<400> SEQUENCE: 172

Met Gln Leu Lys Cys Pro Cys Phe Val Ser Leu Gly Thr Arg Gln Pro
 1               5                  10                  15

Val Trp Lys Lys Leu His Val Ser Ser Gly Phe Phe Ser Gly Leu Gly
                20                  25                  30

Leu Phe Leu Leu Leu Leu Ser Ser Leu Cys Ala Ala Ser Ala Glu Thr
            35                  40                  45

Glu Val Gly Ala Met Val Gly Ser Asn Val Val Leu Ser Cys Ile Asp
 50                  55                  60

Pro His Arg Arg His Phe Asn Leu Ser Gly Leu Tyr Val Tyr Trp Gln
 65                  70                  75                  80

Ile Glu Asn Pro Glu Val Ser Val Thr Tyr Tyr Leu Pro Tyr Lys Ser
                 85                  90                  95

Pro Gly Ile Asn Val Asp Ser Ser Tyr Lys Asn Arg Gly His Leu Ser
            100                 105                 110
```

Leu Asp Ser Met Lys Gln Gly Asn Phe Ser Leu Tyr Leu Lys Asn Val
            115                 120                 125

Thr Pro Gln Asp Thr Gln Glu Phe Thr Cys Arg Val Phe Met Asn Thr
        130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
290                 295                 300

His Arg Ser Tyr Thr Gly Pro Lys Thr Val Gln Leu Glu Leu Thr Asp
305                 310                 315                 320

His Ala

<210> SEQ ID NO 173
<211> LENGTH: 47
<212> TYPE: DNA
<213> ORGANISM: Artificial sequence
<220> FEATURE:
<223> OTHER INFORMATION: Synthetic primer

<400> SEQUENCE: 173
gaggaggagg agaggcccag gcggccgctc gagtggacca aacaccg        47

<210> SEQ ID NO 174
<211> LENGTH: 55
<212> TYPE: DNA
<213> ORGANISM: Artificial sequence
<220> FEATURE:
<223> OTHER INFORMATION: Synthetic primer

<400> SEQUENCE: 174
gaggaggagg aggaggcccc tgaggccgca ttcacagtca cgacagtgcc acctc        55

<210> SEQ ID NO 175
<211> LENGTH: 55
<212> TYPE: DNA
<213> ORGANISM: Artificial sequence
<220> FEATURE:
<223> OTHER INFORMATION: Synthetic primer

<400> SEQUENCE: 175
gaggaggagg aggaggcccc tgaggccgca ttcacagtca cggcagtgcc atctc        55

<210> SEQ ID NO 176

```
<211> LENGTH: 18
<212> TYPE: DNA
<213> ORGANISM: Artificial sequence
<220> FEATURE:
<223> OTHER INFORMATION: Synthetic primer

<400> SEQUENCE: 176
tgtgtggaat tgtgagcg                                                 18

<210> SEQ ID NO 177
<211> LENGTH: 21
<212> TYPE: DNA
<213> ORGANISM: Artificial sequence
<220> FEATURE:
<223> OTHER INFORMATION: Synthetic primer

<400> SEQUENCE: 177
ggcgacattc aaccgattga g                                             21
```

ISOLATION OF THERAPEUTIC TARGET SPECIFIC VNAR DOMAINS TO ICOSL

The present invention relates to the isolation and characterisation of high affinity, antigen specific natural and non-natural binding molecules isolated from immunized and synthetic Elasmobranchii derived libraries. In particular, the present invention relates to shark Variable New Antigen Receptor (VNAR) domains that specifically bind and neutralize the activity of Induced Co-Stimulatory Ligand (ICOSL) a molecule that is an important regulator of immune function. The neutralizing VNAR domains are isolated from two independent sources; an immunized nurse shark library and a synthetic spiny dogfish framework fusion library.

Monoclonal antibody (mAb) based biologics hold many benefits over small molecules as exemplified by their continued clinical success and subsequent economic value to biotechnology and biopharmaceutical drug companies. The inherent ability to specifically bind target and intervene in disease-related biological processes, whilst reducing off-site toxicity, makes them an effective potent and now proven class of therapeutics. There are however limitations to their therapeutic efficacy. Their size and complexity can restrict their utility in certain diseases types and disease locations within the human body. In contrast, a number of so-called alternative scaffolds, derived from both immunoglobulin and non-immunoglobulin based sources have been developed with the aim of tackling some of the well-recognised limitations of larger protein therapeutics.

Shark Immunoglobulin Novel or New Antigen Receptors (IgNAR) are naturally occurring single chain binding domains known to play a role in the adaptive immune system in cartilaginous fish (Greenberg A. S., et al., Nature, 1995. 374(6518): p. 168-173; Dooley, H., et al, Mol. Immunol, 2003. 40(1): p. 25-33; Müller, M. R., et al., mAbs, 2012. 4(6): p. 673-685). An important aspect of this function is the ability to specifically bind with high affinity to target which is achieved through four regions of diversity within the variable domain (VNAR); CDR1, HV2, HV4 and CDR3 (Stanfield, R. L., et al Science, 2004. 305(5691): p. 1770-1773). Additional non-canonical cysteine residues create a repertoire of VNAR isotypes that translate into structurally distinct families with unusual paratope topologies capable of binding more cryptic or hidden epitopes (Stanfield, R. L., et al Science, 2004. 305(5691): p. 1770-1773; Streltsov, V. A., et al, Protein Sci., 2005. 14(11): p. 2901-2909; Stanfield, R. L., et al., J Mol. Biol., 2007. 367(2): p. 358-372). The combination of a lack of light chain partner and CDR2 make VNARs the smallest naturally occurring binding domains in the vertebrate kingdom. This, in addition to their exquisite selectivity for target, inherent solubility and stability make them attractive candidates for therapeutic drug and diagnostic development (Barelle, C. J., et al., Adv. Ex. Med. Biol., 2009. 655: p. 49-62; Griffiths, K., et al., Antibodies, 2012. 2: p. 66-81). The nomenclature in the literature refers to IgNARs as immunoglobulin isotope novel antigen receptors or immunoglobulin isotope new antigen receptors and the terms are synonymous.

The ability to raise a target specific IgNAR response in cartilaginous fish was first demonstrated in nurse sharks (WO 03/014161). Using hen egg lysozyme (HEL) as a model immunogen, antigen specific titres were achieved over time by immunizing target initially with adjuvant followed by iterative boosts in buffer. Prior to this study, it had been generally recognized that the secondary immune response was limited to the evolutionary more advanced vertebrate animals (such as birds and mammals). Thus, it would not have been expected to see such a response in an evolutionary primitive species such as the Elasmobranchii. The responses of sharks to immunogen also differ greatly from that seen in mammals as the IgNAR response has incredibly low antigen-specific serum titres (approximately two orders of magnitude less) than those exhibited by rodents and other mammals. Unlike the lineage of the camelidae single domain antibodies known as nanobodies, the binding domain of IgNAR does not appear to have evolved from a classical immunoglobulin antibody ancestor.

This is evident from the difference in primary sequences which is approximately 80-85% across the framework regions similar to human IgG heavy chains for the nanobody and only 25-30% similarity between IgNAR and human light chain sequences (Dooley, H. and Flajnik, M. F., Eur. J. Immunol., 2005. 35(3): p. 936-945). Studies in juvenile nurse sharks have shown that the isotype repertoire and therefore diversity of IgNAR domains raise against any external challenge is limited to a D-region fused isotype known as Type III. The theory is that this may be a limited response to a common pathogen that young pups may be exposed to whilst still in utero. After approximately six months of development, young adult sharks exhibit a full repertoire and IgNAR response to challenge including multiple different IgNAR isotypes; Type I (only found to date in nurse sharks), Type II, Type IIb, Type III and Type IIIb. The isotype differ in the content and position of non-canonical cysteine restudies which translates into different structural features across the paratope of the binding domains.

Two platforms are available for the isolation of VNARs. The first is based on the role of IgNAR as part of the adaptive immune system of sharks (WO 03/014161). It has been shown now in at least three different species of shark that an IgNAR response can be elicited in response to antigen challenge (Dooley, H., et al, Mol. Immunol, 2003. 40(1): p. 25-33; Müller, M. R., et al., mAbs, 2012. 4(6): p. 673-685; Camacho-Villegas, T., mAbs., 2013. 5(1): p. 80-85 WO2011/056056). As VNAR domains are amenable to phage display, a simple blood sample can be taken from these animals after an iterative process of immunization followed by boosts, RNA extracted and the VNAR repertoire amplified from cDNA generated from this total message (Müller, M. R., et al., Methods Mol. Biol. 2012. 907: p. 177-194, Flajnik, M. F., and Dooley, H., Methods Mol. Biol. 2009. 562: p. 71-82). Cloning into a standard phagemid vector and selecting against target can be used to look for positive hits. A second and complimentary other means of isolating VNAR domains is the construction of a naïve or semi-synthetic phage display library based on a single naturally VNAR framework that often include significant additional diversity through the engineering of the CDR regions (Nuttall, S. D., et al., Mol. Biol. 2001: 38: p. 313-326; Nuttall, S. D., et al., FEBS Letters, 2002. 516: p. 80-86; Liu, J. L., et al., Mol Immunol., 2007. 44: p. 1175-1783; Liu, J. L., et al., BMC Biotech., 2007. 7: p. 78-88). Significant improvements over a single framework library can be achieved through blending or fusing different frameworks from different VNAR isotypes within or across different species. A novel method of generating VNARs from a synthetic library is described in the co-pending international patent application no. PCT/EP2014/058251 filed 23 Apr. 2014 claiming priority from U.S. 61/815,043 filed 23 Apr. 2013 (incorporated by reference).

Both immunized and synthetic library approaches have benefits and challenges. The evolutionarily distant position of the shark immune system encourages a good response to many mammalian proteins. Therefore, immunization typically provides high affinity domains directed against antigen target through following an in vivo maturation processes. This process is a little slower than the related process seen in mammals as it takes place within the animal but approximately 4-8 months to achieve the maturing of the IgNAR repertoire. Selection from a synthetic library shortens this time frame, however the level of success (specificity and affinity) is dependent on the quality and size of the library being screened and generally will deliver domains of lower affinity that may require further refinement through in vitro maturation. A novel method of generating VNARs from a synthetic library is described in the co-pending international patent application no. PCT/EP2014/058251 filed 23 Apr. 2014 claiming priority from U.S. 61/815,043 filed 23 Apr. 2013 (incorporated by reference).

Both methods however have been used successfully to isolate a number of VNAR domains against multiple target classes (Nuttall, S. D. et al., Mol. Biol. 2001: 38: p. 313-326; Dooley, H., et al, Mol. Immunol, 2003. 40(1): p. 25-33; Nuttall, S., D., Protein, 2004. 55: p. 187-197; Liu, J. L., et al., Mol Immunol., 2007. 44: p. 1175-1783; Liu, J. L., et al., BMC Biotech., 2007. 7: p. 78-88; Walsh, R., Virology, 2011. 411(1): p. 132-141; Müller, M. R., et al., mAbs, 2012. 4(6): p. 673-685; Bojalil, R., BMC Immunol., 2013: 14(7): p. 14-17).

Immunomodulatory biologics are powerful tools that can be used to treat immune-related diseases in a number of different therapeutic areas. They can be designed to dampen down hyper-immune responses and therefore have utility in organ transplantation as well as chronic auto-immune and inflammatory conditions such as Rheumatoid Arthritis (RA), Systemic lupus erythematosus (SLE) and psoriasis. Conversely they can act to enhance immune responses in cancer or chronic bacterial or viral infections (Yao, S., et al., Nature Reviews, 2013. 12: p. 130-146). Induced Co-stimulator Ligand (ICOSL) also known as B7 related protein (B7RP-1), CD275 and B7 homologue (B7h) is a cell surface antigen expressed constitutively on antigen presenting cells (APCs) such as B cells, activated monocytes and dendritic cells and is the ligand for the B7 family member, ICOS (CD278) (Yoshinaga, S., K., et al., Int. Immunol., 2000. 12(10): p. 1439-1447). Initially, it was believed that its action was restricted to activation of T cells but more recently the central role of ICOSL in immune modulation has been expanded to both in T cell stimulatory and inhibitory pathways through its interaction with CD28 and CTLA4 respectively. The generation of transgenic mice with lineage-restricted ICOSL expression has demonstrated the role of ICOSL-ICOS interaction in stimulating T-cell responses, T-cell tolerance and T-cell dependent B cell responses and its importance in antibody-mediated disease has been verified in pre-clinical models of human disease including RA, SLE and uveitis (Yoshinaga, S., K., et al., Nature, 1999. 402 (827): p. 827-832; Aicher, A., et al., J. Immunol., 2000. 164(9): p. 4689-4696; Larimore, K., et al., BMC Immunol., 2012. 13(29); p. 1-17; Iwai, H., et al., J. Immunol, 2002. 169(8): p. 4332-4339; Frey, O., et al., Ann. Rheum. Dis., 2010. 69(8): p. 1495-1501; Usui, Y., et al., Eur J Immunol., 2006. 36(11): p. 3071-3081; Hu, Y., L., et al., J. Immunol., 2009. 182(3): p. 1421-1428). The targeted T cell population has been shown to be follicular helper T cells ($T_{FH}$) which interact with germinal centre B cells (Hu, Y., L., et al., J. Immunol., 2009. 182(3): p. 1421-1428).

More recently, the ICOSL-ICOS interaction has been implicated in tumour development through the regulation of immunosuppressive tumor-associated T-regulatory cells (Treg)(Strauss L., et al., J Immunol., 2008. 180: p. 2967-2980; Gobert M, et al., Cancer Res., 2009. 69: p. 2000-2009; Faget, J., et al., Cancer Research, 2012. 72(23): p. 6130-6141). Increased numbers and prevalence of Tregs have been identified in patients with cancer and have been isolated from different tumours and tumour stroma including pancreatic and breast cancer colorectal cancer, gastric and esophageal cancer, leukemia and lymphoma, melanoma, non-small cell lung cancer, ovarian cancer, and hepatocellular carcinoma (Ménétrier-Caux, C. et al., Targ. Oncol., 2012. 7: p. 15-28).

ICOSL is a B7-related transmembrane glycoprotein with two extracellular immunoglobulin-like domains: IgC and IgV. Mutational analysis has shown that the IgV domain forms the interface between receptor and ligand and exhibits low species homology between human and rodent (approximately 44% between human and mouse). Although required for overall integrity of the protein complex, the IgC domain does not form any contact interface with ICOS and is membrane proximal relative to the IgV domain (Chattopadhyay, K., J. Immunol., 2006. 177(6): p. 3920-3929). The organization of the active protein is believed to predominantly be a non-covalent heterodimer and there is evidence to suggest that clustering or oligomerization of these occurs on the cell surface (Chattopadhyay, K., J. Immunol., 2006. 177(6): p. 3920-3929). When the sequence homology between rodent and human target domain is low, the isolation and development of a murine or rat surrogate molecule for pre-clinical development can be useful. The isolation and characterization of such surrogate antibodies against ICOSL has been previously demonstrated (Iwai, H., et al., J. Immunol, 2002. 169(8): p. 4332-4339; Hu, Y., L., et al., J. Immunol., 2009. 182(3): p. 1421-1428).

VNARs isolated from the synthetic library ELSS1 against murine ICOSL bound to the IgV region and exhibited affinities ranging from 40-400 nM are described in co-pending international patent application no. PCT/EP2014/058251 filed 23 Apr. 2014 claiming priority from U.S. 61/815,043 filed 23 Apr. 2013 (incorporated by reference). VNAR domains isolated against human ICOSL (also recognising the IgV domains) have at least one order of magnitude greater affinity for target compared to the anti-murine VNAR domains isolated. For therapeutic benefit, it is critical that the domains isolated against ICOSL, antagonize thereby preventing the interaction with ICOS and subsequent downstream signaling to induce immune responses. T-cell proliferation assays are a robust means of measuring this inhibition of interaction between ICOS-ICOSL and have been conducted previously to exemplify efficacy of lead molecules in vitro. The anti-human ICOSL domains isolated during this study demonstrated a greater than 100 fold increase in potency in T-cell assays compared with their anti-mouse counterparts. It is highly likely that this is due to the increased affinity of the anti-human domains to target compared to that of the anti-mouse. It is therefore predictable that these domains will exhibit a greater efficacy in vivo.

The present invention relates to the unexpected potency in neutralization assays, high affinity and selectivity to target and diversity of VNAR domains isolated against human ICOSL from natural and non-natural sources.

According to the first aspect of this invention, there is provided an ICOSL specific antigen binding molecule comprising an amino acid sequence represented by the formula (I)

A-X-B-Y-C (I)

wherein
A—is SEQ ID NO: 1, SEQ ID NO: 4 or SEQ ID NO: 7
X is a CDR1 region of 6 or 7 amino acid residues
B—is SEQ ID NO: 2, SEQ ID NO: 5 or SEQ ID NO: 8

Y is a CDR3 region of 7, 8, 9, 10, 11, 12, 13, 14, 15, 16, 17, 18, 19, 20, 21 or 22 amino acid residues C—is SEQ ID NO: 3, SEQ ID NO: 6, or SEQ ID NO: 9 or a sequence at least 50% homologous thereto, in which

```
SEQ ID NO: 1 is
TRVDQTPRTATKETGESLTINCVLTDT,
TRVDQTPRTATKETGESLTINCWTGA

SEQ ID NO: 2 is
TSWFRKNPGTTDWERMSIGGRYVESVNKGAKSFSLRIKDLTVADSATY
YCKA
or

TSWFRKNPGTTDWERMSIGGRYVESVNKGAKSFSLRIKDLTVADSATY
ICRA

SEQ ID NO: 3 is
DGAGTVLTVN

SEQ ID NO: 4 is
ASVNQTPRTATKETGESLTINCVLTDT

SEQ ID NO: 5 is
TYWYRKNPGSSNQERISISGRYVESVNKRTMSFSLRIKDLTVADSATYY
CKA
or

TYWYRKNPGSSNQERISISGRYVESVNKRTMSFSLRIKDLTVADSATYI
CRA

SEQ ID NO: 6 is
YGAGTVLTVN

SEQ ID NO: 7 is
ARVDQTPRSVTKETGESLTINCVLRDP
or

ARVDQTPRSVTKETGESLTINCVLRDA
or

ARVDQTPRSVTKETGESLTINCVLRDG
or

ARVDQTPRSVTKETGESLTINCVLRES

SEQ ID NO: 8 is
TCWYRKKSGSTNEESISKGGRYVETVNSGSKSFSLRINDLTVEDGGTYR
CGA
or

TCWSRKKSGSTNEESISKGGRYVETVNSGSKSFSLRINDLTVEDGGTYR
CGL,

TCWTRKKSGSTNEESISKGGRYVETVNSGSKSFSLRINDLTVEDGGTYR
CAL,

TCWYRKKSGSTNEESISKGGRYVETVNSGSKSFSLRINDLTVEDGGTYR
CGV,

TCWYRKKSGSTNEESISKGGRYVETVNSGSKSFSLRINDLTVEDGGTYR
CGH,

TCWYRKKSGSTNEESISKGGRYVETVNSGSKSFSLRISDLTVEDGGTYR
CGH
```

-continued
```
SEQ ID NO: 9 is
CGGGTVVTVN, CGGGTAVTVN, CGDGTAVTVN,
or

CGDGTAVTVN.
```

The amino acid sequences represented by A, X, B, Y and/or C may be derived from the same or different member of the Elasmobranchii subclass. The amino acid sequences represented by A, X, B, Y and/or C may also be derived from the same or different isotypes of VNAR sequences, e.g. type I, type II and/or type III (including type Ib, type IIb and type IIIb). Any generally suitable combination of source material is therefore possible.

In some embodiments of the invention, formula (II) A-X-B-Y-C may be composed of sequences in which elements A, B, and C are represented by (i) SEQ ID NO.s 1, 2, and 3; (ii) SEQ ID NO.s 1, 2, and 6; (iii) SEQ ID NO.s 1, 5, and 3; (iv) SEQ ID NO:s 1, 5 and 6; (v) SEQ ID NO.s 4, 5, and 6; (vi) SEQ ID NO:s 4, 5 and 3; (vii) SEQ ID NO:s 4, 2, and 6; (viii) SEQ ID NO.s 4, 2, and 3; (ix) SEQ ID NOs 7, 8 and 9.

The CDR1 region may be any CDR1 region as shown in FIG. 10A or 10B, or a sequence at least 50% homologous thereto. The CDR3 region may be any CDR3 region as shown in FIG. 10A, 10B or 10C, or a sequence at least 50% homologous thereto.

ICOSL is a B7-related transmembrane glycoprotein with two extracellular immunoglobulin-like domains: IgC and IgV. The human and murine sequences of ICOSL in GenBank are as follows:

Human: Accession: 075144.2; GI: 19855066 (302 aa) (SEQ ID NO: 171)

Mouse: Accession: Q9JHJ8.1; GI: 15214053 (322 aa) (SEQ ID NO: 172)

When the amino acid sequences are aligned, the overall score is 43.38 and the % identity is 47.80. The ICOSL specific antigen binding molecules of the invention may be raised against any ICOSL sequence as an antigen. Suitably, the ICOSL sequence may be a human ICOSL (hICOSL) sequence, or a sequence homologous thereto, or an ICOSL sequence from another animal species which may be presented as an antigen after humanization using standard molecular biology techniques described herein. An example of a human sequence of ICOSL is shown in FIG. 12.

In one embodiment of the invention, the ICOSL specific antigen binding molecule may be a sequence as shown in FIG. 9A or FIG. 9C, or a sequence at least 50% homologous thereto.

Where the CDR3 region is present in an ICOSL specific antigen binding molecule derived from a synthetic library the region may comprise of from 7 to 21 amino acid residues, suitably 7, 9, 10, 11, 12, 13, 14, 16, or 21 amino acid residues.

Where the CDR3 region is present in an ICOSL specific antigen binding molecule derived by an immunization procedure the region may comprise of from 13 to 21 amino acid residues, suitably 13, 19, 20, or 21 amino acid residues.

The ICOSL specific antigen binding molecules can therefore be also described as isolated VNAR domains.

The sequences of VNAR domains of the invention which are isolated from non-natural and natural sources bind specifically to human ICOSL, with high affinity and neutralize the interaction between ICOSL and ICOS.

In one embodiment of the invention, the anti-hICOSL VNAR domains can be isolated from a synthetic library prepared as described co-pending international patent application no. PCT/EP2014/058251 filed 23 Apr. 2014 claiming priority from U.S. 61/815,043 filed 23 Apr. 2013 (incorporated by reference). One example of such a library is the synthetic library ELSS1 which is a framework fusion synthetic library consisting of two contiguous peptide domains fused in multiple combinations. This synthetic library design has proven to be a powerful platform from which to isolate VNARs against multiple target classes due in part to the unique method of fusing different frameworks across isotypes and shark species to significantly increase the library's binding molecule diversity. The anti-human ICOSL domains further exemplify this as they are composed of different isotype framework residues in addition to unique CDR3 and CDR1 sequences. In this embodiment, the VNAR domains may be isolated by screening the library with biotinylated monomeric human ICOSL which was immobilized on streptavidin beads. In an alternative embodiment, VNAR domains may be isolated by screening the library with human ICOSL directly immobilized on solid surfaces such as immunotubes.

In another embodiment of the invention, the anti-human VNAR domains can be isolated from an immunized shark. A nurse shark can be immunized with monomeric human ICOSL in Freunds Complete Adjuvant followed by iterative monthly boosts in PBS. Serum titres of IgNAR against target can be monitored and to determine whether a response to human ICOSL can be seen with between one and three boosts of soluble antigen. The titre from bleed four may be deemed the maximal response achievable from a typical subject animal in such circumstances and RNA can be extracted from the peripheral blood lymphocytes (pbls). From such a sample, cDNA can be generated and the VNAR repertoire amplified using framework 1 and framework 4 specific primers.

The amplicons can be cloned into a phagemid vector transformed into E. coli host cells to create a display library of approximately $1 \times 10^8$ clones. In this embodiment, the VNAR domains may be isolated by screening the library with biotinylated monomeric human ICOSL which can be immobilized on streptavidin beads. In an alternative embodiment, VNAR domains may be isolated by screening the library with human ICOSL directly immobilized on solid surfaces such as immunotubes.

An important advantage of the present invention is the demonstration of potent neutralisation of the ICOS-ICOSL interaction exhibited by the isolated VNAR domains. The efficacy of antagonizing the interaction between ICOS and ICOSL can be demonstrated in cell based in vitro assays or alternative means such as ELISA based antigen assays. The efficacy of neutralization can be demonstrated in multiple protein formats including but not limited to monomeric peri-plasmic expressed protein, VNAR domain-Fc fusions as purified proteins and as mammalian cell supernatants and molecular fusion proteins such as anti-hICOSL VNAR N-terminally and/or C-terminally connected through a peptide linker to a partner protein or proteins.

In one embodiment of the invention soluble peri-plasmic expressed monomeric anti-human ICOSL VNAR domains block the interaction between cell surface expressed ICOS and ICOSL-Fc fusion protein in a multi-well plate ELISA format.

In a further embodiment of the invention, mammalian expressed purified anti-human ICOSL VNAR-Fc domains can block the interaction between cell surface expressed ICOS and ICOSL-Fc fusion protein in a concentration dependent manner.

An additional embodiment is the flexibility to re-format monomeric anti-human ICOSL VNAR domains into N-terminal or C-terminal or both, dimer or trimer or more multiple fusions through a molecular peptide linker. Anti-human ICOSL VNAR domains fused in a trimer format to an anti-human serum albumin VNAR domain and an anti-mouse ICOSL VNAR domain retain the ability to bind to hICOSL and block the interaction between ICOS and ICOSL. In this tri-functional format, all three VNAR domains retain binding to their specific targets.

In a further embodiment of the invention purified anti-human monomeric ICOSL VNAR domains can block the proliferation of primary human T-cells. In an alternative embodiment of the invention, the anti-human ICOSL VNAR domains can be converted into an Fc protein fusion construct which can be expressed in mammalian host cells and purified. This purified material can be titrated in primary human T-cells assays and exhibit concentration dependent inhibition of T-cell proliferation.

Another advantage of the present invention is the high affinity and selectivity demonstrated by anti-human ICOSL domains.

In one embodiment of the invention anti-human ICOSL VNAR domains can be expressed as soluble monomeric proteins domains and passed over immobilized hICOSL in a BIAcore chamber to measure the association and dissociation kinetics of the binding interaction.

In another embodiment of the invention the anti-human ICOSL VNAR domains can be converted into an Fc protein fusion construct which can be expressed in mammalian host cells and purified. This material can then be flowed over immobilized hICOSL in a BIAcore chamber to measure the association and dissociation kinetics of the binding interaction.

In one embodiment of the invention the selectivity of the anti-human ICOSL VNAR domains can be demonstrated by binding to ICOS and ICOSL expressing CHO cell lines, detection using secondary flurochrome tagged antibodies and binding measured using FACS analysis. A further embodiment is the demonstration of the selectivity by ELISA against multiple classes of different proteins.

According to a second aspect of the invention, there is provided a pharmaceutical composition of an ICOSL specific antigen binding molecule of the first aspect of the invention.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg or up to 4 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

The present invention also provides a kit comprising a pharmaceutical composition as defined herein with instructions for use.

According to a third aspect of the invention, there is provided a pharmaceutical composition of the second aspect for use in medicine. Such uses include methods for the treatment of a disease associated with the interaction between ICOSL and its receptor partners including but not limited to ICOS, CD28 and CTLA4, and/or diseases related to T-cell regulation and/or antibody mediated diseases through administration of a therapeutically effective dose of a pharmaceutical composition of the invention as defined above. The composition may comprise at least one ICOSL specific antigen binding molecule (VNAR domain) of the invention, or a combination of such molecules and/or a humanized variant thereof.

As used herein, the term "treatment" includes any regime that can benefit a human. The treatment may be a therapeutic treatment in respect of any existing condition or disorder, or may be prophylactic (preventive treatment).

Diseases which can be treated with the compositions of the present invention include autoimmune and inflammatory diseases that are mediated by T-cell activation specifically involving the subset, $T_{FH}$ cells. Examples of such diseases include but are not limited to, Systemic lupus erythematosus (SLE), Rheumatoid Arthritis (RA), Psoriasis Grave's disease, Myasthenia Gravis, Bullous Pemphigoid, Antiphospholipid syndrome, Uveitis, Devic's disease, Lambert-Eaton Myasthenic Syndrome, Guillain Barre/Miiler Fisher, Stiff man syndrome, Autoimmune Encephalitis, Pemphigus Vulgaris. Other diseases which can be treated with the compositions of the present invention include cancers which are mediated through the activation of T-regulatory (Treg) cells, which include but are not limited to pancreatic and breast cancer colorectal cancer, gastric and esophageal cancer, leukemia and lymphoma, melanoma, non-small cell lung cancer, ovarian cancer, and hepatocellular carcinoma.

In accordance with this aspect of the invention, there is provided a composition of the first aspect for use in the manufacture of a medicament for the treatment of a disease associated with the interaction between ICOSL and its receptor partners including but not limited to ICOS, CD28 and CTLA4, and/or diseases related to T-cell regulation and/or antibody mediated diseases.

The ICOSL specific antigen binding molecules of the present invention may also be used to investigate the nature of a disease condition in a patient. The ICOSL specific antigen binding molecules may be used to prepare images of sites of disease in the body of a subject using imaging techniques such as X-ray, gamma-ray, or PET scanning, or similar. The invention may therefore extend to a method of imaging a site of disease in a subject, comprising administration of a suitably detectably labeled ICOSL specific antigen binding molecule to a subject and scanning the subject's body subsequently. Alternatively, administration of said molecules to a subject may provide for a test result by analysing a sample from the subject following administration of the molecule. Such embodiments may include a method of diagnosis of a disease or medical condition in a subject comprising administration of an ICOSL specific antigen binding molecule of the invention.

In one embodiment of the invention, there is provided an antigen specific antigen binding molecule comprising an amino acid sequence represented by the formula (I)

A-X-B-Y-C (I)

wherein
   A—is SEQ ID NO: 1 or SEQ ID NO: 4
   X is a CDR1 region of 5, 6 or 7 amino acid residues
   B—is SEQ ID NO: 2 or SEQ ID NO: 5
   Y is a CDR3 region of 8, 9, 10, 11, 12, 13, 14, 15, 16, or 17 amino acid residues
   C—is SEQ ID NO: 3 or SEQ ID NO: 6
or a sequence at least 50% homologous thereto,
in which

```
SEQ ID NO: 1 is
TRVDQTPRTATKETGESLTINCVLTDT,
TRVDQTPRTATKETGESLTINCWTGA

SEQ ID NO: 2 is
TSWFRKNPGTTDWERMSIGGRYVESVNKGAKSFSLRIKDLTVADSATYY
CKA
or

TSWFRKNPGTTDWERMSIGGRYVESVNKGAKSFSLRIKDLTVADSATYI
CRA

SEQ ID NO: 3 is
DGAGTVLTVN

SEQ ID NO: 4 is
ASVNQTPRTATKETGESLTINCVLTDT

SEQ ID NO: 5 is
TYWYRKNPGSSNQERISISGRYVESVNKRTMSFSLRIKDLTVADSATYY
CKA
or

TYWYRKNPGSSNQERISISGRYVESVNKRTMSFSLRIKDLTVADSATYI
CRA

SEQ ID NO: 6 is
YGAGTVLTVN.
```

The CDR1 region may be any CDR1 region as shown in FIG. 10A or 10B. The CDR3 region may be any CDR3 region as shown in FIG. 10A, 10B or 10C.

The sequences of this embodiment of the invention may be as shown in FIG. 9A.

In another embodiment of the invention, there is provided an antigen specific antigen binding molecule comprising an amino acid sequence represented by the formula (I)

A-X-B-Y-C (I)

wherein
   A—is SEQ ID NO: 7
   X is a CDR1 region of 6 amino acid residues
   B—is SEQ ID NO: 8
   Y is a CDR3 region of 14, 20, or 22 amino acid residues
   C—is SEQ ID NO: 9
or a sequence at least 50% homologous thereto,
in which

```
SEQ ID NO: 7 is
ARVDQTPRSVTKETGESLTINCVLRDP
or

ARVDQTPRSVTKETGESLTINCVLRDA
```

-continued or

ARVDQTPRSVTKETGESLTINCVLRDG or

ARVDQTPRSVTKETGESLTINCVLRES

SEQ ID NO: 8 is
TCWYRKKSGSTNEESISKGGRYVETVNSGSKSFSLRINDLTVEDGGTYRCGA or

TCWSRKKSGSTNEESISKGGRYVETVNSGSKSFSLRINDLTVEDGGTYRCGL,

TCWTRKKSGSTNEESISKGGRYVETVNSGSKSFSLRINDLTVEDGGTYRCAL,

TCWYRKKSGSTNEESISKGGRYVETVNSGSKSFSLRINDLTVEDGGTYRCGV,

TCWYRKKSGSTNEESISKGGRYVETVNSGSKSFSLRINDLTVEDGGTYRCGH,

TCWYRKKSGSTNEESISKGGRYVETVNSGSKSFSLRISDLTVEDGGTYRCGH,

SEQ ID NO: 9 is
CGGGTVVTVN, CGGGTAVTVN, CGDGTAVTVN, or

CGDGTAVTVN.

The CDR1 region may be any CDR1 region as shown in FIG. 10B. The CDR3 region may be any CDR3 region as shown in FIG. 10B.

The sequences of this embodiment of the invention may be as shown in FIG. 9C.

Definitions

An antigen specific antigen binding molecule of the invention comprises amino acid sequence derived from a synthetic library of Variable New Antigen Receptor (VNAR) molecules or derived from an immunized library of VNAR molecules. The terms VNAR, Immunoglobulin New Antigen Receptor (IgNAR) and New Antigen Receptor (NAR) may be used interchangeably also.

Amino acids are represented herein as either a single letter code or as the three letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "Complementarity Determining Regions" or CDRs (i.e., CDR1 and CDR3) refers to the amino acid residues of a VNAR domain the presence of which are necessary for antigen binding. Each VNAR typically has three CDR regions identified as CDR1 and CDR3. Each complementarity determining region may comprise amino acid residues from a "complementarity determining region" and/or those residues from a "hypervariable loop" (HV). In some instances, a complementarity determining region can include amino acids from both a CDR region and a hypervariable loop. According to the generally accepted nomenclature for VNAR molecules, a CDR2 region is not present.

"Framework regions" (FVV) are those VNAR residues other than the CDR residues. Each VNAR typically has five framework regions identified as FW1, FW2, FW3a, FW3b and FW4.

"Cell", "cell line", and "cell culture" are used interchangeably (unless the context indicates otherwise) and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, etc. Eukaryotic cells use control sequences such as promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

The term "fusion protein" in this text means, in general terms, one or more proteins joined together by chemical means, including hydrogen bonds or salt bridges, or by peptide bonds through protein synthesis or both.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from an allogenic or xenogenic source. The DNA may, optionally, include marker or selection genes, for example, antibiotic resistance genes, temperature resistance genes, etc.

A "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions.

"Identity" describes the relationship between two or more polypeptide sequences or two or more polynucleotide sequences, as determined by comparing the sequences. Identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. (1990) 215, 403).

Preferably, the amino acid sequence of the protein has at least 50% identity, using the default parameters of the BLAST computer program (Atschul et al., J. Mol. Biol. (1990) 215, 403-410) provided by HGMP (Human Genome Mapping Project), at the amino acid level, to the amino acid sequences disclosed herein.

More preferably, the protein sequence may have at least 55%, 60%, 65%, 66%, 67%, 68%, 69%, 70%, 75%, 80%, 85%, 90% and still more preferably 95% (still more preferably at least 96%, 97%, 98% or 99%) identity, at the nucleic acid or amino acid level, to the amino acid sequences as shown herein.

The protein may also comprise a sequence which has at least 50%, 55%, 60%, 65%, 66%, 67%, 68%, 69%, 70%, 75%, 80%, 85%, 90%, 95%, 96%, 97%, 98%, or 99% identity with a sequence disclosed herein, using the default parameters of the BLAST computer program provided by HGMP, thereto A "library" refers to a plurality of VNARs or VNAR fragment sequences or the nucleic acids that encode these sequences. The origin of the library can be from non-natural sources or synthetic in nature where diversity has been engineered into a natural or combination of natural frameworks or can be from a natural source as exemplified from VNAR domains isolated from RNA extracted from an immunized animal.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

"Natural" or "naturally occurring" VNARs, refers to VNARs identified from a non-synthetic source, for example, from a tissue source obtained ex vivo, or from the serum of an animal of the Elasmobranchii subclass. These VNARs can include VNARs generated in any type of immune response, either natural or otherwise induced. Natural VNARs include the amino acid sequences, and the nucleotide sequences that constitute or encode these antibodies. As used herein, natural VNARs are different than "synthetic VNARs", synthetic VNARs referring to VNAR sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promotor or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. Phage display technology allows for the preparation of large libraries of randomized protein variants which can be rapidly and efficiently sorted for those sequences that bind to a target antigen with high affinity. The display of peptide and protein libraries on phage can be used for screening millions of polypeptides for ones with specific binding properties. Polyvalent phage display methods have been used for displaying small random peptides and small proteins through fusions to the genes encoding coat proteins pIII, pVIII, pVI, pVII or pIX of filamentous phage.

A "phagemid" is a plasmid vector having a bacterial origin of replication, e.g., ColEI, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. An example of a phagemid display vector is pWRIL-1.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, or a derivative thereof.

The term "protein" means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues, variants and derivatives of a protein wherein the fragment, analogue, variant or derivative retains essentially the same biological activity or function as a reference protein. Examples of protein analogues and derivatives include peptide nucleic acids, and DARPins (Designed Ankyrin Repeat Proteins). A "polypeptide of the invention" is an ICOSL specific antigen binding molecule as defined herein.

A fragment, analogue, variant or derivative of the protein may be at least 25 preferably 30 or 40, or up to 50 or 100, or 60 to 120 amino acids long, depending on the length of the original protein sequence from which it is derived. A length of 90 to 120, 100 to 110 amino acids may be convenient in some instances.

The fragment, derivative, variant or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the additional amino acids are fused to the mature polypeptide, such as a leader or auxiliary sequence which is employed for purification of the polypeptide. Such fragments, derivatives, variants and analogues are deemed to be within the scope of those skilled in the art from the teachings herein.

"Oligonucleotides" are short-length, single- or double-stranded polydeoxynucleotides that are chemically synthesized by known methods (such as phosphotriester, phosphite, or phosphoramidite chemistry, using solid-phase techniques). Further methods include the polymerase chain reaction (PCR) used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation. DNA is "purified" when the DNA is separated from non-nucleic acid impurities (which may be polar, non-polar, ionic, etc.).

A "source" or "template" VNAR", as used herein, refers to a VNAR or VNAR antigen binding fragment whose antigen binding sequence serves as the template sequence upon which diversification according to the criteria described herein is performed. An antigen binding sequence generally includes within a VNAR preferably at least one CDR, preferably including framework regions.

A "transcription regulatory element" will contain one or more of the following components: an enhancer element, a promoter, an operator sequence, a repressor gene, and a transcription termination sequence.

"Transformation" means a process whereby a cell takes up DNA and becomes a "transformant". The DNA uptake may be permanent or transient. A "transformant" is a cell which has taken up and maintained DNA as evidenced by the expression of a phenotype associated with the DNA (e.g., antibiotic resistance conferred by a protein encoded by the DNA).

A "variant" or "mutant" of a starting or reference polypeptide (for example, a source VNAR or a CDR thereof), such as a fusion protein (polypeptide) or a heterologous polypeptide (heterologous to a phage), is a polypeptide that (1) has an amino acid sequence different from that of the starting or reference polypeptide and (2) was derived from the starting or reference polypeptide through either natural or artificial mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a non-random codon set that encodes a sequence with a variant amino acid (with respect to the amino acid found at the corresponding position in a source VNAR or antigen binding fragment) would be a variant polypeptide with respect to a source VNAR or antigen binding fragment. Thus, a variant CDR refers to a CDR comprising a variant sequence with respect to a starting or reference polypeptide sequence (such as that of a source VNAR or antigen binding fragment). A variant amino acid, in this context, refers to an amino acid different from the amino acid at the corresponding position in a starting or reference polypeptide sequence (such as that of a source VNAR or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type" or "reference" sequence or the sequence of a "wild-type" or "reference" protein/polypeptide, such as a coat protein, or a CDR of a source VNAR, may be the reference sequence from which variant polypeptides are derived through the introduction of mutations. In general, the "wild-type" sequence for a given protein is the sequence that is most common in nature.

Similarly, a "wild-type" gene sequence is the sequence for that gene which is most commonly found in nature. Mutations may be introduced into a "wild-type" gene (and thus the protein it encodes) either through natural processes or through man induced means. The products of such processes are "variant" or "mutant" forms of the original "wild-type" protein or gene.

Library Construction

Synthetic libraries may be constructed according to any suitable technique as described above. One method of generating VNARs from a synthetic library is described in co-pending international patent application no. PCT/EP2014/058251 filed 23 Apr. 2014 claiming priority from U.S. 61/815,043 filed 23 Apr. 2013 (incorporated by reference).

Methods of substituting an amino acid of choice into a template nucleic acid are well established in the art. For example, libraries can be created by targeting amino acid positions in at least one CDR region for amino acid substitution with variant amino acids using the Kunkel method (Kunkel et al., Methods Enzymol. (1987), 154, 367-382). Specific codon sets can therefore be constructed as desired.

A codon set is a set of different nucleotide triplet sequences used to encode desired variant amino acids. Codon sets can be represented using symbols to designate particular nucleotides or equimolar mixtures of nucleotides as shown in below according to the IUB code. Typically, a codon set is represented by three capital letters e.g. RRK, GST, TKG, TWC, KCC, KCT, and TRM.

IUB CODES
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T) H
N (A or C or G or T)

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids.

Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Gene Link Inc, Hawthorn N.Y., or Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

Nucleic acids encoding other source or template molecules are known or can be readily determined. Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, (1987) 75: 5765).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., Methods Enzymol., (1987) 153, 3). Thus, the DNA that is to be mutated can be inserted into one of these vectors in order to generate single-stranded template.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of coding sequence 1, and the other strand (the original template) encodes the native, unaltered sequence of coding sequence 1. This heteroduplex molecule is then transformed into a suitable host cell, usually a prokaryote such as E. coli JM101. After growing the cells, they are plated onto agarose plates and screened using the oligonucleotide primer radio-labelled with a $^{32}$-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site (s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. (Meth. Enzymol. (1987), 153, 3). Thus, the DNA that is to be mutated must be inserted into one of these vectors in order to generate a single-stranded template.

Oligonucleotide sets can be used in a polymerase chain reaction using a nucleic acid template sequence as the template to create nucleic acid cassettes. The nucleic acid template sequence can be any portion of a VNAR molecule (i.e., nucleic acid sequences encoding amino acids targeted for substitution). The nucleic acid template sequence is a portion of a double stranded DNA molecule having a first nucleic acid strand and complementary second nucleic acid strand. The nucleic acid template sequence contains at least a portion of a VNAR domain and has at least one CDR. In some cases, the nucleic acid template sequence contains more than one CDR. An upstream portion and a downstream portion of the nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the nucleic acid template sequence. Use of these oligonucleotides can introduce two or more codon sets into the PCR product (i.e., the nucleic acid cassette) following PCR. The oligonucleotide primer that hybridizes to regions of the nucleic acid sequence encoding the VNAR domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes (i.e., PCR reaction products) into an expression vector having additional VNAR sequences.

Protein Expression

Nucleic acid sequences encoding antigen specific antigen binding molecules of the invention may be present in a nucleic acid construct. Such nucleic acid constructs may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

The nucleic acid construct may suitably include a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence.

Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidine kinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA element, optionally without enhancer element) for example, the minimum sequence of the CMV promoter. Preferably, the promoter is contiguous to the nucleic acid sequence.

As stated herein, the nucleic acid construct may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

The vector may be any suitable expression vector, such as pET. The vector may include such additional control sequences as desired, for example selectable markers (e.g. antibiotic resistance, fluorescence, etc.), transcriptional control sequences and promoters, including initiation and termination sequences.

The promoter may be any suitable promoter for causing expression of the protein encoded by a nucleic acid sequence of the invention, e.g. a CMV promoter, human phosphoglycerate kinase (hPGK) promoter.

Such vectors may be present in a host cell. Representative examples of appropriate host cells for expression of the nucleic acid construct of the invention include virus packaging cells which allow encapsulation of the nucleic acid into a viral vector; bacterial cells, such as Streptococci, Staphylococci, *E. coli*, *Streptomyces* and *Bacillus subtilis*; single cells, such as yeast cells, for example, *Saccharomyces cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*. Suitably, the host cell is a eukaryotic cell, such as a CHO cell or a HEK293 cell.

Introduction of an expression vector into the host cell can be achieved by calcium phosphate transfection, DEAE-dextran mediated transfection, microinjection, cationic-lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Cold Spring Harbor Laboratory Press, Cold Spring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryotic and eukaryotic hosts are described by Sambrook et al, Molecular Cloning, a Laboratory Manual, Second Edition, Cold Spring Harbor Laboratory Press, Cold Spring Harbor, N.Y. (1989).

The invention also provides a host cell comprising any of the polynucleotides and/or vectors of the invention described herein. According to the invention, there is provided a process for the production of an antigen specific antigen binding molecule of the invention, comprising the step of expressing a nucleic acid sequence encoding said molecule in a suitable host cell as defined herein.

Proteins can be recovered and purified from recombinant cell cultures by standard methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin and/or heparin chromatography. For therapy, the nucleic acid construct, e.g. in the form of a recombinant vector, may be purified by techniques known in the art, such as by means of column chromatography as described in Sambrook et al, Molecular Cloning, a Laboratory Manual, Second Edition, Cold Spring Harbor Laboratory Press, Cold Spring Harbor, N.Y. (1989).

This aspect of the invention therefore extends to processes for preparing a fusion protein of the invention comprising production of the fusion protein recombinantly by expression in a host cell, purification of the expressed fusion protein by means of peptide bond linkage, hydrogen or salt bond or chemical cross linking. In some embodiments of this aspect of the invention, the fusion protein could be prepared using hydrogen or salt bonds where the peptide is capable or multimerisation, for example dimerisation or trimerisation.

Protein Expression as a Library

Protein expression in the form of a library of protein may be achieved by any suitable technique. One method of expressing a library of proteins is described in co-pending international patent application no. PCT/EP2014/058251 filed 23 Apr. 2014 claiming priority from U.S. 61/815,043 filed 23 Apr. 2013 (incorporated by reference).

By way of example, nucleic acid cassettes can be cloned into any suitable vector for expression of a portion or the entire VNAR containing the targeted amino acid substitutions generated. The nucleic acid cassette can be cloned into a vector allowing production of a portion or the entire VNAR chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components.

In another embodiment, wherein a particular variant amino acid combination is to be expressed, the nucleic acid cassette contains a sequence that is able to encode all or a portion of the VNAR sequence, and is able to encode the variant amino acid combinations. For production of antigen specific antigen binding molecules containing these variant amino acids or combinations of variant amino acids, the nucleic acid cassettes can be inserted into an expression vector containing additional VNAR sequence, for example all or portions of the various CDR, Framework and/or Hypervariable regions. These additional sequences can also be fused to other nucleic acids sequences, such as sequences which encode viral coat protein components and therefore allow production of a fusion protein.

One aspect of the invention includes a replicable expression vector comprising a nucleic acid sequence encoding a gene fusion, wherein the gene fusion encodes a fusion protein comprising a VNAR sequence and a second VNAR sequence, fused to all or a portion of a viral coat protein. The vectors can include a variety of components and are preferably constructed to allow for movement of VNAR sequences between different vectors and/or to provide for display of the fusion proteins in different formats.

Examples of vectors include phage vectors. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII, major coat protein PVIII, p3, Soc (T4), Hoc (T4), gpD (of bacteriophage lambda), minor bacteriophage coat protein 6 (pVI) (filamentous phage; Hufton et al, J Immunol Methods. (1999), 231, (1-2): 39-51), variants of the M13 bacteriophage major coat protein (P8) (Weiss et al, Protein Sci (2000) 9 (4): 647-54). The fusion protein can be displayed on the surface of a phage and suitable phage systems include M13K07 helper phage, M13R408, M13-VCS, and Phi X 174, pJuFo phage system (Pereboev et al J Virol. (2001); 75(15): 7107-13), and hyperphage (Rondot et al Nat Biotechnol. (2001); 19(1): 75-8). The preferred helper phage is M13K07, and the preferred coat protein is the M13 Phage gene III coat protein. The preferred host is $E.\ coli$, and protease deficient strains of $E.\ coli$. Vectors, such as the fthI vector (Enshell-Seijffers et al., Nucleic Acids Res. (2001); 29(10): E50-0) can be useful for the expression of the fusion protein.

The expression vector also can have a secretory signal sequence fused to the DNA encoding each VNAR or fragment thereof. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al, Gene, (1983) 68, 1931), MalE, PhoA and other genes.

A preferred prokaryotic signal sequence for practicing this invention is the $E.\ coli$ heat-stable enterotoxin II (STII) signal sequence as described by Chang et al (Gene 55. 189 (1987)), and malE.

The vector also typically includes a promoter to drive expression of the fusion protein. Promoters most commonly used in prokaryotic vectors include the lac Z promoter system, the alkaline phosphatase pho A promoter (Ap), the bacteriophage XPL promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (e.g., GFP), or beta-galactosidase protein which can be useful for detection or purification of the fusion protein expressed on the surface of the phage or cell.

Nucleic acid sequences encoding, for example, a gD tag, also provide for positive or negative selection of cells or virus expressing the fusion protein. In some embodiments, the gD tag is preferably fused to a VNAR sequence which is not fused to the viral coat protein component. Nucleic acid sequences encoding, for example, a polyhistidine tag, are useful for identifying fusion proteins including VNAR sequences that bind to a specific antigen using immunohistochemistry. Tags useful for detection of antigen binding can be fused to either a VNAR sequence not fused to a viral coat protein component or a VNAR sequence fused to a viral coat protein component.

Another useful component of the vectors used to practice this invention is phenotypic selection genes. Typical phenotypic selection genes are those encoding proteins that confer antibiotic resistance upon the host cell. By way of illustration, the ampicillin resistance gene (Amp), and the tetracycline resistance gene ($Tet^r$) are readily employed for this purpose.

The vector can also include nucleic acid sequences containing unique restriction sites and suppressible stop codons. The unique restriction sites are useful for moving VNAR sequences between different vectors and expression systems. The suppressible stop codons are useful to control the level of expression of the fusion protein and to facilitate purification of soluble VNAR fragments. For example, an amber stop codon can be read as Gln in a supE host to enable phage display, while in a non-supE host it is read as a stop codon to produce soluble VNAR fragments without fusion to phage coat proteins. These synthetic sequences can be fused to one or more VNAR sequences in the vector.

It may be convenient to use vector systems that allow the nucleic acid encoding a sequence of interest, for example a CDR having variant amino acids, to be easily removed from the vector system and placed into another vector system. For example, appropriate restriction sites can be engineered in a vector system to facilitate the removal of the nucleic acid sequence encoding a VNAR. The restriction sequences are usually chosen to be unique in the vectors to facilitate efficient excision and ligation into new vectors. VNAR sequences can then be expressed from vectors without extraneous fusion sequences, such as viral coat proteins or other sequence tags.

Between nucleic acid encoding VNAR sequences (gene 1) and the viral coat protein component (gene 2), DNA encoding a termination or stop codon may be inserted, such termination codons including UAG (amber), UAA (ocher) and UGA (opel) (Microbiology, Davis et al., Harper & Row, New York, 1980, pp. 237, 245-47 and 374). The termination or stop codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as E. coli suppressor strain (Bullock et al., BioTechniques 5: 376-379 (1987)). Any acceptable method may be used to place such a termination codon into the mRNA encoding the fusion polypeptide.

The suppressible codon may be inserted between the first gene encoding a VNAR sequence, and a second gene encoding at least a portion of a phage coat protein. Alternatively, the suppressible termination codon may be inserted adjacent to the fusion site by replacing the last amino acid triplet in the VNAR sequence or the first amino acid in the phage coat protein. The suppressible termination codon may be located at or after the C-terminal end of a dimerization domain. When the plasmid containing the suppressible codon is grown in a suppressor host cell, it results in the detectable production of a fusion polypeptide containing the polypeptide and the coat protein. When the plasmid is grown in a non-suppressor host cell, the VNAR sequence is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

Antigen Specific Antigen Binding Molecules of the Invention

In certain embodiments of the invention, the antigen specific antigen binding molecule has an amino acid sequence selected from the group as shown in FIG. 9.

In one embodiment of the invention, the antigen specific antigen binding molecule is an amino acid sequence as shown in FIG. 9, or any variant, analogue, derivative or fragment thereof, including a sequence having 50% identity thereto, or at least 60%, 70%, 80%, 90%, 95% or 99% identity, using the default parameters of the BLAST computer program provided by HGMP, thereto. In one embodiment of the invention, the antigen specific antigen binding molecule is humanized. It may be convenient to provide for a humanized binding molecule of the invention with from about 20% to about 85% humanization, for example from about 25% to about 60% humanization. Humanization of VNAR domains has been conducted previously (WO 2013/167883; Kovalenka, O. V., et al., J. Biol. Chem., 2012. 288(24): p. 17408-17419) exemplifying the ability to increase the percentage identity of amino acid residues to that of a human antibody framework with minimal loss of functionality. The anti-human albumin binding VNAR E06, which originated from a spiny dogfish, has been humanized ((E06 patent reference; Kovalenka, O. V., et al., J. Biol. Chem., 2012. 288(24): p. 17408-17419) and retains the ability to bind target. The fused isotype frameworks from the ELSS1 library (known as 2V and 5V) also originated from spiny dogfish and as such there is a 92% identity across the framework residues of an example anti-human ICOSL from FIG. 9A (1D12) to the framework of E06. It would be predicted that the synthetic anti-human ICOSL domains could be humanized using the same methodology. The same is true of the immunized anti-human ICOSL domains which are nurse shark type I domains, similar to the anti-HEL domains, 5A7, which has also been humanized ((WO 2013/167883; Kovalenka, O. V., et al., J. Biol. Chem., 2012. 288(24): p. 17408-17419).

The antigen specific antigen binding molecule may comprise additional N-terminal or C-terminal sequences which are cleaved off prior to use which may assist in purification and/or isolation during processes for the production of the molecule as described herein. For example, $(Ala)_3(His)_6$ at the C-terminal end of the molecule.

Also included within the invention are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions where the properties of a protein of the present invention are preserved in the variant form compared to the original form. Variants also include fusion proteins comprising an antigen specific antigen binding molecule according to the invention.

As discussed above, an example of a variant of the present invention includes a protein in which there is a substitution of one or more amino acids with one or more other amino acids. The skilled person is aware that various amino acids have similar properties. One or more such amino acids of a substance can often be substituted by one or more other such amino acids without interfering with or eliminating a desired activity of that substance. Such substitutions may be referred to as "non-conservative" amino acid substitutions.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

A fusion protein may comprise an antigen specific antigen binding molecule of the present invention fused to a heterologous peptide or protein sequence providing a structural element to the fusion protein. In other embodiments, the fusion protein may comprise an antigen specific antigen binding molecule of the present invention fused with a molecule having biological activity, i.e. a therapeutic protein having a pharmacologically useful activity. The molecule may be a peptide or protein sequence, or another biologically active molecule.

For example, the antigen specific antigen binding molecule may be fused to a heterologous peptide sequence which may be a poly-amino acid sequence, for example a plurality of histidine residues or a plurality of lysine residues (suitably 2, 3, 4, 5, or 6 residues), or an immunoglobulin domain (for example an Fc domain).

References to heterologous peptides sequences include sequences from other mammalian species, such as murine and human and any heterologous peptides sequences originated from other VNAR domains.

Where the fusion protein comprises an antigen specific antigen binding molecule of the present invention fused with a molecule having biological activity, a biologically active moiety may be a peptide or protein having biological activity such as an enzyme, immunoglobulin, cytokine or a fragment thereof. Alternatively, the biologically active molecule may be an antibiotic, an anti-cancer drug, an NSAID, a steroid, an analgesic, a toxin or other pharmaceutically active agent. Anti-cancer drugs may include cytotoxic or cytostatic drugs.

In some embodiments, the fusion protein may comprise an antigen specific antigen binding molecule of the invention fused to another immunoglobulin variable or constant region, or another antigen specific antigen binding molecule of the invention. In other words, fusions of antigen specific antigen binding molecules of the invention may be of variable length, e.g. dimers, trimers, tetramers, or higher order multimer (i.e. pentamers, hexamers, heptamers octamers, nonamers, or decamers, or greater). In specific embodiments this can be represented as a multimer of monomer VNAR subunits.

For example, where the VNAR CDRs are fused to an additional peptide sequence, the additional peptide sequence can provide for the interaction of one or more fusion polypeptides on the surface of the viral particle or cell. These peptide sequences can therefore be referred to as "dimerization domains". Dimerization domains may comprise at least one or more of a dimerization sequence, or at least one sequence comprising a cysteine residue or both. Suitable dimerization sequences include those of proteins having amphipathic alpha helices in which hydrophobic residues are regularly spaced and allow the formation of a dimer by interaction of the hydrophobic residues of each protein; such proteins and portions of proteins include, for example, leucine zipper regions.

Dimerization domains can also comprise one or more cysteine residues (e.g. as provided by inclusion of an antibody hinge sequence within the dimerization domain). The cysteine residues can provide for dimerization by formation of one or more disulfide bonds. In one embodiment, wherein a stop codon is present after the dimerization domain, the dimerization domain comprises at least one cysteine residue. The dimerization domains are preferably located between the antibody variable or constant domain and the viral coat protein component.

In fusion proteins of the present invention, the antigen specific antigen binding molecule may be directly fused or linked via a linker moiety to the other elements of the fusion protein. The linker may be a peptide, peptide nucleic acid, or polyamide linkage. Suitable peptide linkers may include a plurality of amino acid residues, for example, 4, 5, 6, 7, 8, 9, 10, 15, 20 or 25 amino acids, such as $(Gly)_4$ (SEQ ID NO: 10), $(Gly)_5$ (SEQ ID NO: 11), $(Gly)_4Ser$ (SEQ ID NO: 12), $(Gly)_4(Ser)(Gly)_4$ (SEQ ID NO: 13), or combinations thereof or a multimer thereof (for example a dimer, a trimer, or a tetramer, or greater). For example, a suitable linker may be $(GGGGS)_3$ (SEQ ID NO: 14). Alternative linkers include $(Ala)_3(His)_6$ (SEQ ID NO: 15) or multimers thereof. Also included is a sequence which has at least 50%, 60%, 70%, 80%, 90%, 95% or 99% identity, using the default parameters of the BLAST computer program provided by HGMP, thereto.

In some cases the vector encodes a single VNAR-phage polypeptide fused to a coat protein. In these cases the vector is considered to be "monocistronic", expressing one transcript under the control of a certain promoter.

Illustrative examples of such vectors utilize the alkaline phosphatase (AP) or Tac promoter to drive expression of a monocistronic sequence encoding VNAR regions, with a linker peptide between the domains. The cistronic sequence can be connected at the 5'-end to an *E. coli* maIE or heat-stable enterotoxin II (STII) signal sequence and at its 3'end to all or a portion of a viral coat protein (for example, the pIII protein). The vector may further comprise a sequence encoding a dimerization domain (such as a leucine zipper) at its 3'-end, between the second variable domain sequence and the viral coat protein sequence. Fusion polypeptides comprising the dimerization domain are capable of dimerizing to form a complex of two polypeptides.

In other cases, the VNAR sequences (multiple VNAR sequences or fragments) can be expressed as separate polypeptides, the vector thus being "bicistronic", allowing the expression of separate transcripts. In these vectors, a suitable promoter, such as the Ptac or PhoA promoter, can be used to drive expression of a bicistronic message. A first cistron, encoding, for example, a first VNAR sequence, can be connected at the 5'-end to a E. coli maIE or heat-stable enterotoxin II (STII) signal sequence and at the 3'-end to a nucleic acid sequence encoding a gD tag. A second cistron, encoding, for example, a second VNAR sequence, can be connected at its 5'-end to a E. coli maIE or heat-stable enterotoxin II (STII) signal sequence and at the 3'-end to all or a portion of a viral coat protein.

An example vector can comprise, a suitable promoter, such as Ptac or PhoA (AP) promoter which drives expression of first cistron encoding a VNAR sequence operably linked at 5'-end to an E. coli maIE or heat stable enterotoxin II (STII) signal sequence and at the 3'-end to a nucleic acid sequence encoding a gD tag. The second cistron encodes, for example, another VNAR sequence operatively linked at 5'-end to a E. coli maIE or heat stable enterotoxin II (STII) signal sequence and at 3'-end has a dimerization domain comprising IgG hinge sequence and a leucine zipper sequence followed by at least a portion of viral coat protein.

Fusion polypeptides of a VNAR sequence can be displayed on the surface of a cell, virus, or phagemid particle in a variety of formats. These formats include single chain fragment and multivalent forms of these fragments. The multivalent forms may be a dimer, or a higher multimer. The multivalent forms of display may be convenient because they have more than one antigen binding site which generally results in the identification of lower affinity clones and also allows for more efficient sorting of rare clones during the selection process.

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell.

Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using. Cells are grown in culture in standard culture broth, optionally for about 6-48 hours (or to OD600=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

Use of phage display for identifying target antigen binders, with its various permutations and variations in methodology, are well established in the art. One approach involves constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, followed by a process that entails selection or sorting by contacting the recombinant phage particles with a target antigen so that at least a portion of the population of particles bind to the target with the objective to increase and enrich the subsets of the particles which bind from particles relative to particles that do not bind in the process of selection. The selected pool can be amplified by infecting host cells for another round of sorting on the same target with different or same stringency. The resulting pool of variants is then screened against the target antigens to identify novel high affinity binding proteins.

These novel high affinity binding proteins can be useful as therapeutic agents as antagonists or agonists, and/or as diagnostic and research reagents.

Fusion polypeptides such as antibody variable domains comprising the variant amino acids can be expressed on the surface of a phage, phagemid particle or a cell and then selected and/or screened for the ability of members of the group of fusion polypeptides to bind a target antigen which is typically an antigen of interest.

Such fusion proteins may be prepared by any suitable route, including by recombinant techniques by expression in host cell or cell-free systems, as well as by chemical synthetic routes.

Selection of Library Members Specific for ICOSL

The processes of selection for binders to target can also be include sorting on a generic protein having affinity for antibody variable domains such as protein L or a tag specific antibody which binds to antibody or antibody fragments displayed on phage, which can be used to enrich for library members that display correctly folded antibody fragments (fusion polypeptides).

Target ICOSL proteins may be isolated from natural sources or prepared by recombinant methods by procedures known in the art. Two main strategies of selection (sorting) for affinity which can be are (i) the solid-support method or plate sorting or immobilized target sorting; and (ii) the solution-binding method.

For the solid support method, the target protein may be attached to a suitable solid or semi-solid matrix which are known in the art such as agarose beads, acrylamide beads, glass beads, cellulose, various acrylic copolymers, hydroxyalkyl methacrylate gels, polyacrylic and polymethacrylic copolymers, nylon, neutral and ionic carriers, etc.

After attachment of the target antigen to the matrix, the immobilized target is contacted with the library expressing the fusion polypeptides under conditions suitable for binding of at least a subset of the phage particle population with the immobilized target antigen. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the high affinity binders. Binders may be dissociated from the immobilized target by a variety of methods. These methods include competitive dissociation using the wild-type ligand (e.g. excess target antigen), altering pH and/or ionic strength, and methods known in the art. Selection of binders typically involves elution from an affinity matrix with a suitable elution material such as acid like 0.1 M HCl or ligand. Elution with increasing concentrations of ligand could elute displayed binding molecules of increasing affinity.

The binders can be isolated and then re-amplified in suitable host cells by infecting the cells with the viral particles that are binders (and helper phage if necessary, e.g. when viral particle is a phagemid particle) and the host cells are cultured under conditions suitable for amplification of the particles that display the desired fusion polypeptide. The phage particles are then collected and the selection process is repeated one or more times until binders of the target antigen are enriched in a way. Any number of rounds of selection or sorting can be utilized. One of the selection or sorting procedures can involve isolating binders that bind to a generic affinity protein such as protein L or an antibody to a polypeptide tag present in a displayed polypeptide such as antibody to the gD protein or polyhistidine tag.

Another selection method is the "solution-binding method" which allows solution phase sorting with an improved efficiency over the conventional solution sorting method. The solution binding method has been used for finding original binders from a random library or finding improved binders from a library that was designated to improve affinity of a particular binding clone or group of clones. The method comprises contacting a plurality of polypeptides, such as those displayed on phage or phagemid particles (library), with a target antigen labeled or fused with a tag molecule. The tag could be biotin or other moieties for which specific binders are available. The stringency of the solution phase can be varied by using decreasing concentrations of labeled target antigen in the first solution binding phase.

To further increase the stringency, the first solution binding phase can be followed by a second solution phase having high concentration of unlabeled target antigen after the initial binding with the labeled target in the first solution phase. Usually, 100 to 1000 fold of unlabeled target over labeled target is used in the second phase (if included). The length of time of incubation of the first solution phase can vary from a few minutes to one to two hours or longer to reach equilibrium. Using a shorter time for binding in this first phase may bias or select for binders that have fast on-rate. The length of time and temperature of incubation in second phase can be varied to increase the stringency. This provides for a selection bias for binders that have slow rate of coming off the target (off-rate).

After contacting the plurality of polypeptides (displayed on the phage/phagemid particles) with a target antigen, the phage or phagemid particles that are bound to labeled targets are separated from phage that do not bind. The particle-target mixture from solution phase of binding is isolated by contacting it with the labeled target moiety and allowing for its binding to, a molecule that binds the labeled target moiety for a short period of time (e.g. 2-5 minutes). The initial concentration of the labeled target antigen can range from about 0.1 nM to about 1000 nM. The bound particles are eluted and can be propagated for next round of sorting. Multiple rounds of sorting are preferred using a lower concentration of labeled target antigen with each round of sorting.

For example, an initial sort or selection using about 100 to 250 nM labeled target antigen should be sufficient to capture a wide range of affinities, although this factor can be determined empirically and/or to suit the desire of the practitioner. In the second round of selection, about 25 to 100 nM of labeled target antigen may be used. In the third round of selection, about 0.1 to 25 nM of labeled target antigen may be used. For example, to improve the affinity of a 100 nM binder, it may be desirable to start with 20 nM and then progress to 5 and 1 nM labeled target, then, followed by even lower concentrations such as about 0.1 nM labeled target antigen.

As described herein, combinations of solid support and solution sorting methods can be advantageously used to isolate binders having desired characteristics. After selection/sorting on target antigen for a few rounds, screening of individual clones from the selected pool generally is performed to identify specific binders with the desired properties/characteristics. Preferably, the process of screening is carried out by automated systems to allow for high-throughput screening of library candidates.

Two major screening methods are described below. However, other methods may also be used. The first screening method comprises a phage ELISA assay with immobilized target antigen, which provides for identification of a specific binding clone from a non-binding clone. Specificity can be determined by simultaneous assay of the clone on target coated well and BSA or other non-target protein coated wells. This assay is automatable for high throughput screening.

One example comprises a method of selecting for an antibody variable domain that binds to a specific target antigen from a library of antibody variable domain by generating a library of replicable expression vectors comprising a plurality of polypeptides; contacting the library with a target antigen and at least one nontarget antigen under conditions suitable for binding; separating the polypeptide binders in the library from the nonbinders; identifying the binders that bind to the target antigen and do not bind to the nontarget antigen; eluting the binders from the target antigen; and amplifying the replicable expression vectors comprising the polypeptide binder that bind to a specific antigen.

Another example comprises an affinity screening assay that provides for screening for clones that have high affinity from clones that have low affinity in a high throughput manner. In the assay, each clone is assayed with and without first incubating with target antigen of certain concentration for a period of time (for e.g. 30-60 minutes) before application to target coated wells briefly (e.g. 5-15 minutes). Then bound phage is measured by usual phage ELISA method, e.g. using anti-M13 HRP conjugates. The ratio of binding signal of the two wells, one well having been pre-incubated with target and the other well not preincubated with target antigen is an indication of affinity. The selection of the concentration of target for first incubation depends on the affinity range of interest. For example, if binders with affinity higher than 10 nM are desired, 1000 nM of target in the first incubation is often used. Once binders are found from a particular round of sorting (selection), these clones can be screened with affinity screening assay to identify binders with higher affinity.

Combinations of any of the sorting/selection methods described above may be adopted as convenient. For example, in one embodiment, polypeptide binders are first selected for binding to immobilized target antigen. Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labeled target antigen to form a complex, wherein the concentration ranges of labeled target antigen from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labeled target antigen is used. The high affinity polypeptide binders isolated using this selection method can then be screened for high affinity using for example, a solution phase ELISA assay or a spot competition ELISA assay.

After binders are identified by binding to the target antigen, the nucleic acid can be extracted. Extracted DNA can then be used directly to transform E. coli host cells or alternatively, the encoding sequences can be amplified, for example using PCR with suitable primers, and sequenced by typical sequencing method. Variable domain DNA of the binders can be restriction enzyme digested and then inserted into a vector for protein expression.

Other suitable methods of selection may comprise generating a plurality of polypeptides with one or more diversified CDR regions, sorting the plurality of polypeptides for binders to a target antigen by contacting the plurality of polypeptides with a target antigen under conditions suitable for binding; separating the binders to the target antigen from those that do not bind; isolating the binders; and identifying the high affinity binders. The affinity of the binders that bind to the target antigen can be determined using competition ELISA such as described herein. Optionally, the polypeptides can be fused to a polypeptide tag such as gD, poly-his or FLAG which can be used to sort binders in combination with sorting for the target antigen.

Another example comprises selecting for an antigen specific antigen binding molecule that binds to a target antigen from a library of VNARs comprising: a) generating a library of replicable expression vectors comprising a plurality of polypeptides of the invention; b) isolating polypeptide binders to a target antigen from the library by contacting the library with an immobilized target antigen under conditions suitable for binding; c) separating the polypeptide binders in the library from the nonbinders and eluting the binders from the target antigen; d) amplifying the replicable expression vectors having the polypeptide binders; and e) optionally, repeating steps a-d at least twice.

The method may further comprise: f) incubating the amplified replicable expression vectors comprising polypeptide binders with a concentration of labeled target antigen in the range of 0.1 nM to 1000 nM under conditions suitable for binding to form a mixture; g) contacting the mixture with an immobilized agent that binds to the label on the target antigen; h) separating the polypeptide binders bound to labeled target antigen and eluting the polypeptide binders from the labeled target antigen; i) amplifying replicable expression vectors comprising the polypeptide binders; and j) optionally, repeating steps f) to i) at least twice, using a lower concentration of labeled target antigen each time. Optionally, the method may comprise adding an excess of unlabeled target antigen to the mixture and incubating for a period of time sufficient to elute low affinity binders from the labeled target antigen.

Another example comprises a method of isolating or selecting for high affinity binders to a target antigen from a library of replicable expression vectors comprising: a) generating a library of replicable expression vectors comprising a plurality of polypeptides of the invention; b) contacting the library with a target antigen in a concentration of at least about 0.1 nM to 1000 nM to isolate polypeptide binders to the target antigen; c) separating the polypeptide binders from the target antigen and amplifying the replicable expression vector comprising the polypeptide binders; d) optionally, repeating steps a-c at least twice, each time with a lower concentration of target antigen to isolate polypeptide binders that bind to lowest concentration of target antigen; e) selecting the polypeptide binder that binds to the lowest concentration of the target antigen for high affinity by incubating the polypeptide binders with several different dilutions of the target antigen and determining the IC50 of the polypeptide binder; and f) identifying a polypeptide binder that has an affinity for the target antigen of about 0.1 nM to 200 nM.

Another example comprises an assay for selecting polypeptide binders from a library of replicable expression vectors comprising a plurality of polypeptides of the invention comprising: a) contacting the library with a concentration of labeled target antigen in a concentration range of 0.1 nM to 1000 nM, under conditions suitable for binding to form a complex of a polypeptide binders and the labeled target antigen; b) isolating the complexes and separating the polypeptide binders from the labeled target antigen; c) amplifying the replicable expression vector comprising the polypeptide binders; d) optionally, repeating steps a-c at least twice, each time using a lower concentration of target antigen.

Optionally, the method may further comprise adding an excess of unlabeled target antigen to the complex of the polypeptide binder and target antigen. In a preferred embodiment, the steps of the method are repeated twice and the concentrations of target in the first round of selection is about 100 nM to 250 nM, and in the second round of selection is about 25 nM to 100 nM, and in the third round of selection is about 0.1 nM to 25 nM.

Other potential routes of identifying binding proteins of interest include a method of screening a library of replicable expression vectors comprising a plurality of polypeptides of the invention comprising: a) incubating first a sample of the library with a concentration of a target antigen under conditions suitable for binding of the polypeptides to the target antigen; b) incubating a second sample of the library without a target antigen; c) contacting each of the first and second sample with immobilized target antigen under conditions suitable for binding of the polypeptide to the immobilized target antigen; d) detecting the amount of the bound polypeptides to immobilized target antigen for each sample; e) determining the affinity of the polypeptide for the target antigen by calculating the ratio of the amounts of bound polypeptide from the first sample over the amount of bound polypeptide from the second sample.

The libraries may also be screened for binding to a specific target and for lack of binding to nontarget antigens. In one aspect, another embodiment provides a method of screening for an antibody variable domain that binds to a specific target antigen from a library of VNARs comprising: a) generating a library of replicable expression vectors comprising a plurality of polypeptides of the invention; b) contacting the library with a target antigen and at least one nontarget antigen under conditions suitable for binding; c) separating the polypeptide binders in the library from the nonbinders; d) identifying the binders that bind to the target antigen and do not bind to the nontarget antigen; e) eluting the binders from the target antigen; and f) amplifying the replicable expression vectors comprising the polypeptide binder that bind to a specific antigen.

Combinations of any of the sorting/selection methods described above may be combined with the screening methods. For example, in one embodiment, polypeptide binders are first selected for binding to immobilized target antigen.

Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labeled target antigen to form a complex, wherein the concentration range of labeled target antigen is from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labeled target antigen is used. The high affinity polypeptide binders isolated using this selection method can then be screened for high affinity using for example, a solution phase ELISA assay or a spot competition ELISA assay.

Pharmaceutical Compositions and Uses

According to the invention, there is provided a pharmaceutical composition of antigen specific antigen binding molecule of the invention. Such compositions include fusion proteins comprising said antigen specific antigen binding molecules.

The pharmaceutical composition may also comprise an antigen specific antigen binding molecule of the present invention fused to a therapeutic protein, or a fragment thereof. The therapeutic protein may be a hormone, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a blood clotting factor (for example, Factor Vila, Factor VIII, Factor IX, VonWillebrand Factor or Protein C) or another protein from the blood coagulation cascade (for example, antithrombin); a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-4, BMP-5, BMP-6, BMP-7, BMP-8, BMP-9, BMP10, BMP-11, BMP-12, BMP-13); an interleukin receptor antagonist (e.g. IL-1ra, IL-1RII); a chemokine (e.g. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; an enzyme, for example a free-radical scavenging enzyme e.g. superoxide dismutase or catalase or a pro-drug converting enzyme (e.g. angiotensin converting enzyme, deaminases, dehydrogenases, reductases, kinases and phosphatases); a peptide mimetic; a protease inhibitor; a tissue inhibitor of metalloproteinases (TIMPs e.g. TIMP1, TIMP2, TIMP3 or TIMP4) or a serpin (inhibitors of serine proteases).

In other embodiments of the invention, the therapeutic protein in the fusion protein may be an antibody, or a engineered fragment thereof, including Fab, Fc, F(ab')₂ (including chemically linked F(ab')₂ chains), Fab', scFv (including multimer forms thereof, i.e. di-scFv, or tri-scFv), sdAb, or BITE (bi-specific T-cell engager). Antibody fragments also include variable domains and fragments thereof, as well as other VNAR type fragments (IgNAR molecules). The antigen specific binding molecules of the invention can be monomeric or dimeric or trimeric or multimeric and can be homologous or heterologous capable of binding the same or different targets and/or the same or different epitopes on the same target. In other words, the antigen specific binding molecules may be monospecific, bispecific, trispecific or multispecific. Reference to heterologous antigen specific binding molecules of the invention refers to binding to different epitopes on the same target. Engineered fragments also include Fc-fusions of an antigen specific binding molecule of the invention and an Fc fragment of an antibody.

The pharmaceutical composition may be composed of a number of antigen specific antigen binding molecules of the invention, for example dimers, trimers, or higher order multimers, i.e. 2, 3, 4, 5, 6, 7, or 8-mers, fused to the therapeutic protein.

The fusion of the antigen specific antigen binding molecules of the invention to the therapeutic protein may at any convenient site on the protein and may be N-, C- and/or N-/C-terminal fusion(s). In one embodiment of the invention, the fusion of the antigen specific antigen binding molecules of the invention is to both the N- and C-terminals of a therapeutic protein.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg or up to 4 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

According to the invention, there is provided an antigen specific antigen binding molecule of the invention for use in medicine. This aspect of the invention therefore extends to the use of such of an antigen specific antigen binding molecule of the invention in the manufacture of a medicament for the treatment of a disease in a patient in need thereof. An antigen specific antigen binding molecule of the invention can also be used to prepare a fusion protein comprising such a specific binding molecule as defined above in relation to pharmaceutical compositions of the invention.

Such uses also embrace methods of treatment of diseases in patients in need of treatment comprising administration to the patient of a therapeutically effective dosage of a pharmaceutical composition as defined herein comprising an antigen specific antigen binding molecule of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The antigen specific antigen binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

The antigen specific antigen binding molecules of the present invention may also be used to investigate the nature of a disease condition in a patient. The antigen specific antigen binding molecules may be used to prepare images of sites of disease in the body of a subject using imaging techniques such as X-ray, gamma-ray, or PET scanning, or similar. The invention may therefore extend to a method of imaging a site of disease in a subject, comprising administration of a suitably detectably labeled antigen specific antigen binding molecule to a subject and scanning the subject's body subsequently. Alternatively, administration of said molecules to a subject may provide for a test result by analysing a sample from the subject following administration of the molecule.

Alternatively, the antigen specific antigen binding molecules may be used to assay for the presence of target analytes in an in vitro sample or in a patient's body. The sample may any biological sample material from the body such as cells, tissue, blood, plasma, saliva, tears, semen, cerebrospinal fluid (CSF) and/or milk. Such methods may comprise the addition of a suitably labelled antigen specific antigen binding molecule to a sample of interest. The binding of the labelled antigen specific antigen binding molecule to the target analyte can then be detected by any suitable means such as fluorescence, radioactivity etc. according standard enzyme-linked immunosorbent assay (ELISA) and/or radioimmuno assay (RIA) techniques.

Such embodiments may include a method of diagnosis of a disease or medical condition in a subject comprising administration to the subject of an antigen specific antigen binding molecule of the invention, or the addition of said antigen specific antigen binding molecule to a sample.

The antigen specific antigen binding molecule may find further use in the immunoaffinity purification of a molecule of interest. Suitably the antigen specific antigen binding molecule of the invention may be bound to a substrate over which a sample containing the molecule of interest is passed or introduced such that the molecule of interest binds in a releasable manner to the antigen specific antigen binding molecule. Such methods of immunoaffinity purification can find use in bioprocessing of substances from biological sources or chemical reactions which may be otherwise difficult to prepare in a sufficiently pure form, such as for example therapeutic substances.

The substrate to which the antigen specific antigen binding molecule can be bound may be a column comprising a polymer in the form of beads or powder, a plate (e.g. a multi-well plate), microfluidic system. Such substrates may be composed of any suitable inert material such as silicon, glass or a plastics material, optionally in the form of a chip. In some arrangements, it may be convenient to site multiple antigen specific antigen binding molecules of the same or different antigen specific on such substrates. After binding of the substance to the antigen specific antigen binding molecule, the substrate can be washed to remove unbound material and then the purified substance can be eluted by suitable means.

In the present application reference is made to a number of drawings in which:

FIG. 1 shows human ICOSL specific titres from the serum of an immunized shark illustrating the ability to raise an immune response in nurse sharks to this protein immunogen. The negative control was milk.

Figure 2:
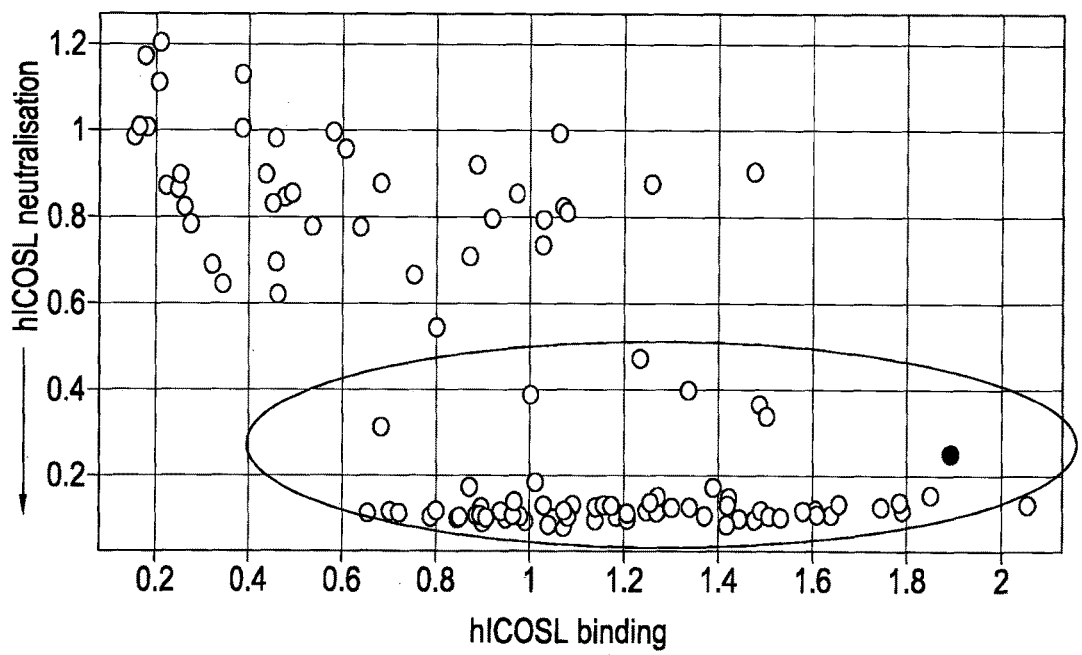
Figure 6A:
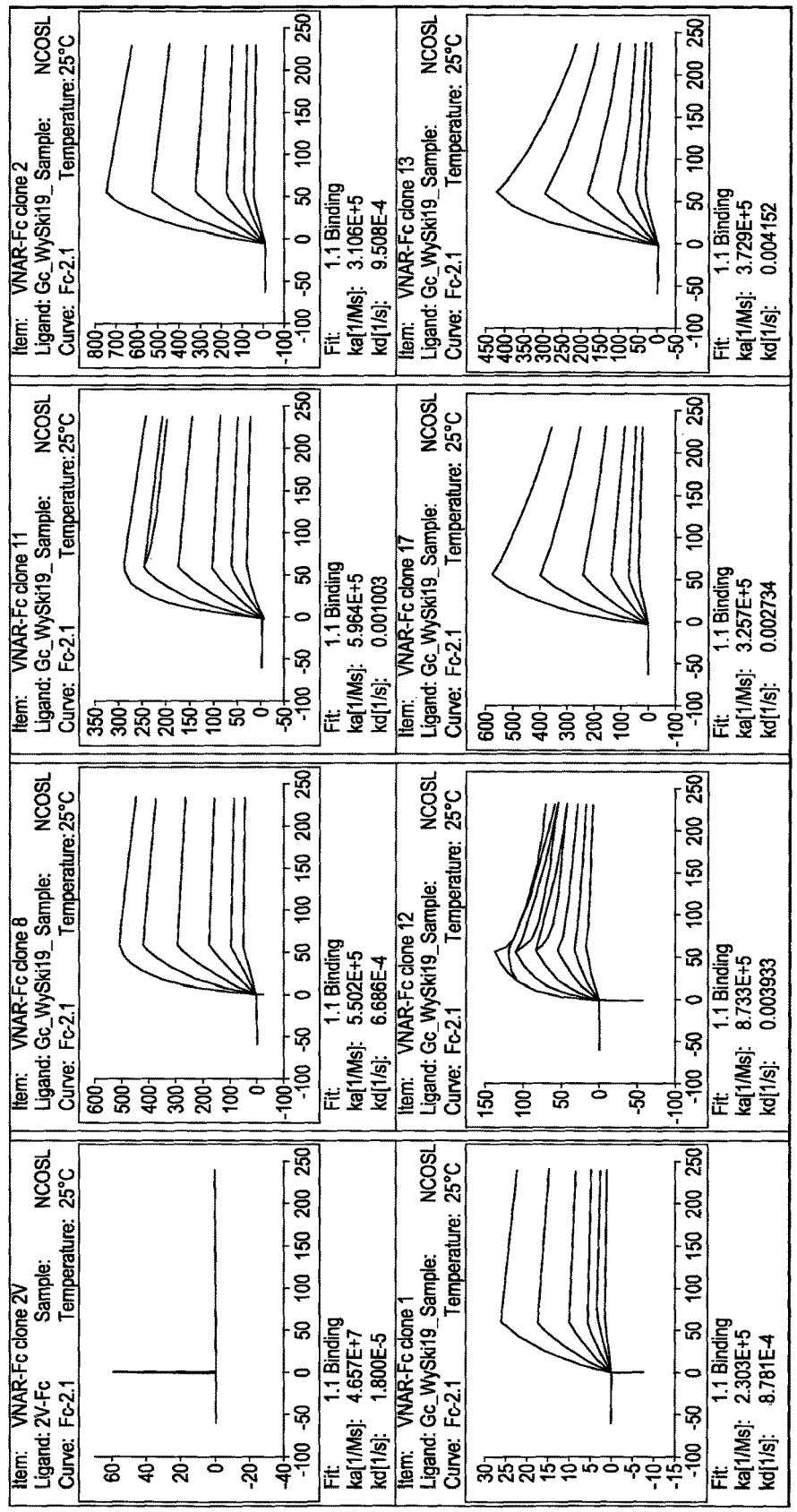

FIG. 2 shows cell based neutralization assays conducted on monoclonal soluble peri-plasmic expressed protein from the positive selection hits. Low signals are indicative of positive binding to hICOSL and resultant inhibition of the receptor ligand interaction. Positive neutralizing clones are highlighted in the grey oval. After only one round of selection against target, enrichment for hICOSL specific positive hits was evident of which, approximately 60% demonstrated the ability to block binding of ligand (ICOSL) to receptor (ICOS) and were taken forward for further analysis. A known neutralizing 150 kDa mAb clone is shown in black and is used here as a positive control for the assay.

FIG. 3 demonstrates the binding of anti-hICOSL VNAR domains isolated from the synthetic library ELSS1. VNAR domains were assessed for binding as purified Fc fusions to hICOSL expressing CHO cells. The negative (non-binding) VNAR-Fc known as 2V was also included.

FIG. 4 demonstrates the selectivity of hits isolated from both the synthetic and immunized libraries against CHO cells expressing either hICOSL or mICOSL or parental CHO cells. Positive clones were expressed as soluble protein and tested for binding to cell surface expressed target compared to parental cells using a FACS based assay. Positive anti-hICOSL and anti-mICOSL mAbs were included as positive controls to show the expected shift when positive cell binding was detected. The wild-type control is the VNAR 2V which is a naïve non-binding control domain. FIG. 4A shows domains 1-16 which are positive hits isolated from a hICOSL immunized library described in Example 1. FIG. 4B shows the selectivity of synthetic-library derived hits isolated from ELSS1 against hICOSL.

FIG. 5 shows data which exemplifies the selectivity of the anti-hICOSL VNAR hits against multiple different antigens (hICOSL, HSA, TNF-α, KLH, MPBS, TG, HEL and BSA) by soluble protein binding ELISA. Dark regions indicate high levels of binding; background binding is shown in grey. Positive control anti-HSA and anti-hICOSL binding clones were incorporated into the ELISAs as indicated on the figure.

FIG. 6 shows the affinity, analysed on a T-100 BIAcore, of lead clones isolated. FIG. 6A shows the sensograms from each of seven lead immunized anti-hICOSL VNAR clones as expressed and purified Fc constructs and the kinetics of binding. 2V-Fc was used as the negative VNAR control.

FIG. 6B lists the calculated KD values for the lead synthetic-library and immunized-library derived clones.

Figure 7A:
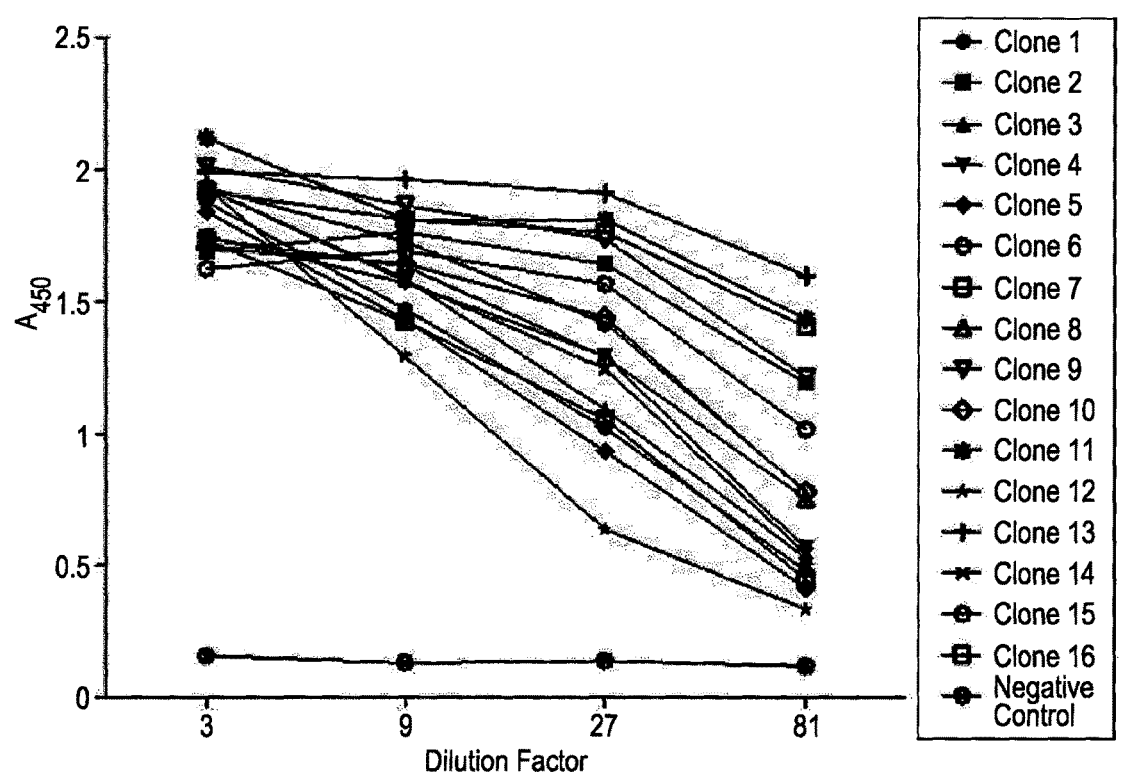
Figure 7B:
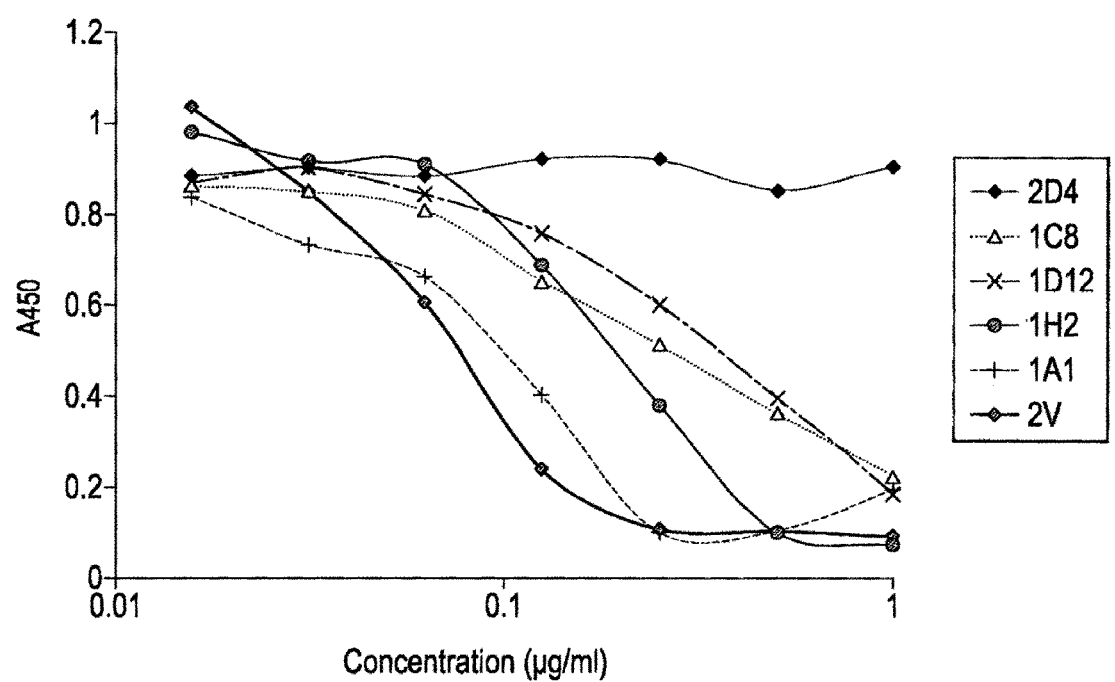

FIG. 7 demonstrates the ability of the anti-ICOSL VNAR domains isolated from the synthetic library and immunized library to inhibit the interaction between soluble ICOS and cell expressed ICOSL. Purified Fc fusion VNAR domains were expressed and purified and titrated in a cell based assay. Decreased absorbance levels indicate positive neutralization. The negative control was the VNAR domain, 2V-Fc. FIG. 7A shows the results with the lead anti-hICOSL VNAR domains from the immunized library and FIG. 7B, those leads from the synthetic library.

FIG. 8 shows the IC50 values measured when the anti-hICOSL VNARs were incorporated into primary human T-cell proliferation assays. 1C8, 1C4, 1G5, 1A1, 2D4, 1H2 and 1D12 were all VNAR domains isolated from ELSS1, re-formatted into Fc format and purified. A commercially available anti-hICOSL antibody, mAb165, is the positive control. Results are shown from two independent donors known as donor 450 and donor 452.

FIG. 9 lists both the amino acid and nucleic acid sequences of all the positive anti-hICOSL VNAR clones isolated from both synthetic (clones 1A9, 1C8, 1D12, 266, 2D3, 2D4, 2E8, 1G5, 1H02, 1A1, 1C04, 1A6, 1B2, 2C10, 2C7, 2G6, 3E8, 3G11, 465, 4G1, 5A12, 5610, 569, 5C1, 5E6, 5F3, 5F6 and 5G1) and immunized (clones 1, 2, 8, 11, 12, 13 and 17) libraries. FIG. 9A lists the amino acid sequences (SEQ ID NOs: 16-42) and FIG. 9B the nucleic acid sequences (SEQ ID NOs: 43-69) of the synthetic-library derived anti-hICOSL VNAR domains. FIG. 9C lists the amino acid sequences (SEQ ID NOs: 70-79) and FIG. 9D the nucleic acid sequences (SEQ ID NOs: 80-89) of the immunized-library derived anti-hICOSL VNAR domains.

FIG. 10 lists the CDR1 and CDR3 amino acid sequences from all the positive anti-hICOSL VNAR clones isolated from both synthetic and immunized libraries. FIG. 10A lists those isolated from the synthetic library (SEQ ID NOs: 90-143) and FIG. 10B, those isolated from the immunized library (SEQ ID NOs: 144-158). FIG. 10C shows the sequences of ICOSL positive VNAR clones isolated from ELSS2 synthetic VNAR library (SEQ ID NOs: 159-169). Positive hits were all-cross species and cross-isotype framework fusions as illustrated.

FIG. 11 demonstrates the binding of anti-ICOSL VNAR domains to target when re-formatted as a molecular fusion to an albumin binding VNAR domain (E06). FIG. 11A shows the binding of a trimer VNAR domain fusion protein consisting of the anti-murine ICOSL VNAR domain, CC3 linked via a (GGGS)$_4$ (SEQ ID NO: 170) amino acid stretch to the anti-human ICOSL VNAR domain, 2D4 linked via a (GGGS)$_4$ (SEQ ID NO: 170) amino acid stretch to the anti-human serum albumin VNAR domain, E06. The expressed trimer fusion protein was tested for binding to mICOSL, hICOSL and HSA by ELISA. The concentration dependant curves demonstrate that binding to each target was achieved and the protein fusion is therefore tri-functional. FIG. 11B shows a trimer variant where the order of the molecular fusions is altered resulting in E06 being both N and C-terminally fused between the anti-mICOSL and anti-hICOSL VNAR domains. In this orientation, binding by all VNAR domains to their specific target is also demonstrated.

FIG. 12 shows the GenBank database sequence for hICOSL recorded at 16 Apr. 2014 under accession no. 075144 (Version 075144.2 GI:19855066; DBSOURCE UniProtKB: locus ICOSL_HUMAN, accession 075144) (SEQ ID NO: 171).

The present invention will also be further described by way of reference to the following Examples which are present for the purposes of illustration only and are not to be construed as being limitations on the invention.

Abbreviations Used:

VNAR, Variable Novel Antigen Receptor; scFv, single chain antibody fragment; FW, framework; HV, Hypervariable loop; CDR, complementarity determining region; SOE-PCR, splice-by-overlap extension polymerase chain reaction.

EXAMPLE 1: ISOLATION OF ANTI-HICOSL VNAR DOMAINS BY BIOPANNING OF ELSS1 SYNTHETIC VNAR LIBRARY

To isolate anti-hICOSL domains, the ELSS1 synthetic library (prepared as described in co-pending international patent application no. PCT/EP2014/058251 filed 23 Apr. 2014 claiming priority from U.S. 61/815,043 filed 23 Apr. 2013 (incorporated by reference) was screened using both solid state and pre-coated bead based methods against monomeric human ICOSL. Positive hits were obtained using both methods. In brief, solid state selections were carried out as follows: an immunotube was coated with the target antigen at the desired concentration in 4 ml PBS. The tubes was then sealed and left to incubate O/N at 4° C. with rotation. After washing 3× with PBS, block the tube with 2% (w/v) M-PBS for 1 h. Block 0.5-1 ml input phage in M-PBS (2% (w/v) final concentration) with rotation for 1 h. Then add blocked phage to the tube, make up to 4 ml with 2% (w/v) M-PBS and incubate with rotation at 20 rpm for 1 hour followed by static incubation for a further 1 h. Unbound phage is discarded and the tube is washed 5-10× with PBST followed by 5-10× washes with PBS. Phage was eluted by adding 1 ml of 100 mM triethylamine with rotation at 20 rpm for up to 10 min. The output phage solution is neutralized by the addition 0.5 ml 1M Tris-HCl pH 7.5. The eluted phage is added to 10 ml of mid-log ER2738 cells, mixed and incubated without agitation at 37° C. for 30 mins followed by centrifugation at 2,500×g for 15 min. The pellet was re-suspended in 1 ml 2× TY-G and spread onto a Bio-Assay dish containing TYE-GA agar and incubated O/N at 30° C. O/N.

For the pre-coated bead assays, antigen was biotinylated as per manufacturer's instructions. Biotinylated material was incubated with 30 μl of Dynabeads M-280 Streptavidin (Invitrogen) for 30 minutes at R/T rotating at 20 rpm. Library selection with pre-decorated beads was carried out using essentially the same method described above for solid state selections where input phage and Dynabeads were pre-blocked with 4% (w/v) M-PBS for 1 hour rotating at R/T. Phage were then de-selected by the addition of blocked beads for 1 h, rotating at R/T followed by the addition of antigen coated beads for 1 hour at R/T at 20 rpm. After washing 5× with PBST, bound phage was eluted by rotating for 8 minutes in 400 μl 100 mM TEA and neutralised by the addition of 200 μl 1M Tris-HCl pH 7.5. E coli infection of eluted phage was carried out as described for the solid state selections.

Peri-plasmic expression of soluble VNAR protein was conducted as follows; overnight cultures of selected colonies were inoculated and grown for 5 hours at 37° C. and 250 rpm in deepwell plates (Greiner, Bio-One) containing 1 ml/well of 2×TY, 0.1% glucose, 100 μg/ml ampicillin. Transcription was induced by the addition of 1 mM IPTG, and incubated overnight at 28° C. and 250 rpm. Deepwell plates were centrifuged for 10 minutes at 3200 rpm, and the resulting pellets re-suspended in 200 µl ice-cold TES buffer then 200 µl ice-cold 1:5 TES buffer. After 30 minutes incubation on ice, centrifugation was repeated, with the soluble VNAR present in the resulting supernatant. Expression was assessed via standard binding ELISA, with 1 µg/ml antigen coated on immuno-plates (Nunc, Thermo Scientific) and anti-c-myc-HRP (Invitrogen) as the detection antibody. Soluble expressed monoclonals were assessed for both the ability to specifically bind target and the ability to block target from binding the receptor, ICOS in 96-well based cell neutralization assays. Ligand-receptor neutralisation assays were conducted as follows: CHO cells expressing human ICOS receptor were grown to confluency in DMEM/F12+ 5% FBS media in 96-well cell culture plates (Greiner, Bio-One). hICOSL-hFc (20 µl at 450 ng/ml) was pre-incubated for 1 h with 40 µl of anti-hICOSL-VNAR domains in DMEM/F12+2% FBS and then added to the cells. Following 1 hour incubation at 16° C. cells were gently washed 3 times with DMEM/F12+2% FBS and incubated for another 40 minutes at 16° C. with goat anti-human Fc-HRP (SIGMA) diluted 1:10000 in the same media. Afterwards the cells were washed again 3 times with DMEM/F12+2% FBS media and ones with PBS and developed with TMB substrate.

EXAMPLE 2: CONSTRUCTION OF A PHAGE DISPLAY LIBRARY FROM NURSE SHARKS IMMUNIZED WITH HICOSL

Nurse sharks (*Ginglymostoma cirratum*) were immunized subcutaneously with 250 µg total protein in Complete Freunds adjuvant followed by three monthly intravenous boosts of 250 µg total protein in PBS. Serum titre responses to human ICOSL were analysed using the anti-nurse shark IgNAR monoclonal antibody, GA8. The response detected is shown in FIG. 1. Peripheral blood lymphocytes were isolated from bleed 4 and total RNA was purified as per the SIGMA Amplification Grade DNase I protocol. cDNA was synthesised according to manufacturer's instructions (Invitrogen, SuperScript III) and VNAR DNA was amplified (NEB Phusion HF PCR Master Mix) according to manufacturer's protocols using the following nurse shark-specific primer combinations:

```
FW1
                                      (SEQ ID NO: 173)
5'-GAGGAGGAGGAGAGGCCCAGGCGGCCGCTCGAGTGGACCAAACAC
CG-3'
with either FW4r1
                                      (SEQ ID NO: 174)
5'-GAGGAGGAGGAGGAGGCCCCTGAGGCCGCATTCACAGTCACGACA
GTGCCACCTC-3'
or FW4r2
                                      (SEQ ID NO: 175)
5'-GAGGAGGAGGAGGAGGCCCCTGAGGCCGCATTCACAGTCACGGCA
GTGCCATCTC-3'.
```

Amplified PCR products were digested overnight with SfiI and cloned into a SfiI digested phagemid display vector. The ligated samples were transformed into electrocompetent TG1 cells (Lucigen) following the manufacturer's protocol. Estimated library size was 1×10⁸ clones. Library QC was conducted on library monoclonals by PCR with vector-specific primers 1082 (5'-TGTGTGGAATTGTGAGCG-3') (SEQ ID NO: 176) and 1059 (5'-GGCGACATTCAAC-CGATTGAG-3') (SEQ ID NO: 177).

Library monoclonals were grown with 800 µl 2xTY, 2% glucose, 100 µg/ml ampicillin for 2 hours at 37° C. and 285 rpm. Cultures were infected with 10⁹ M13K07 helper phage (NEB) for 30 minutes at 37° C., followed by a 1 hour incubation shaking at 150 rpm at 37° C. Cultures were centrifuged for 10 minutes at 3200 rpm. The pellet was re-suspended in 2xTY, 100 µg/ml ampicillin, 50 µg/ml kanamycin, and incubated overnight at 25° C. and 280 rpm. Plates were centrifuged for 20 minutes at 3200 rpm, and 600 µl of supernatant transferred to 150 µl ice-cold 20% PEG/2.5 M NaCl, and incubated on ice for 30 min. Phage was collected by centrifuging for 20 minutes at 3200 rpm and the pellet re-suspended in 200 µl 4% (w/v) MPBS.

EXAMPLE 3: SCREENING IMMUNIZED LIBRARIES FOR POSITIVE ANTI-HICOSL VNAR HITS

Pre-coated bead selections were conducted using biotinylated hICOSL and the same method employed for the synthetic library screening as described in Example 1. Positive phage hits were assessed for binding and neutralizing as peri-plasmic expressed soluble protein as described for the synthetic library screening in Example 1. FIG. 2 exemplifies positive hits that demonstrate the blocking of ICOSL and ICOS in cell based assays. The clones highlighted in the shaded oval were taken forward and sequenced.

EXAMPLE 4: IN VITRO BINDING AND SELECTIVITY OF SYNTHETIC-LIBRARY DERIVED AND IMMUNIZED-LIBRARY DERIVED VNAR HITS AGAINST HICOSL

Figure 3:
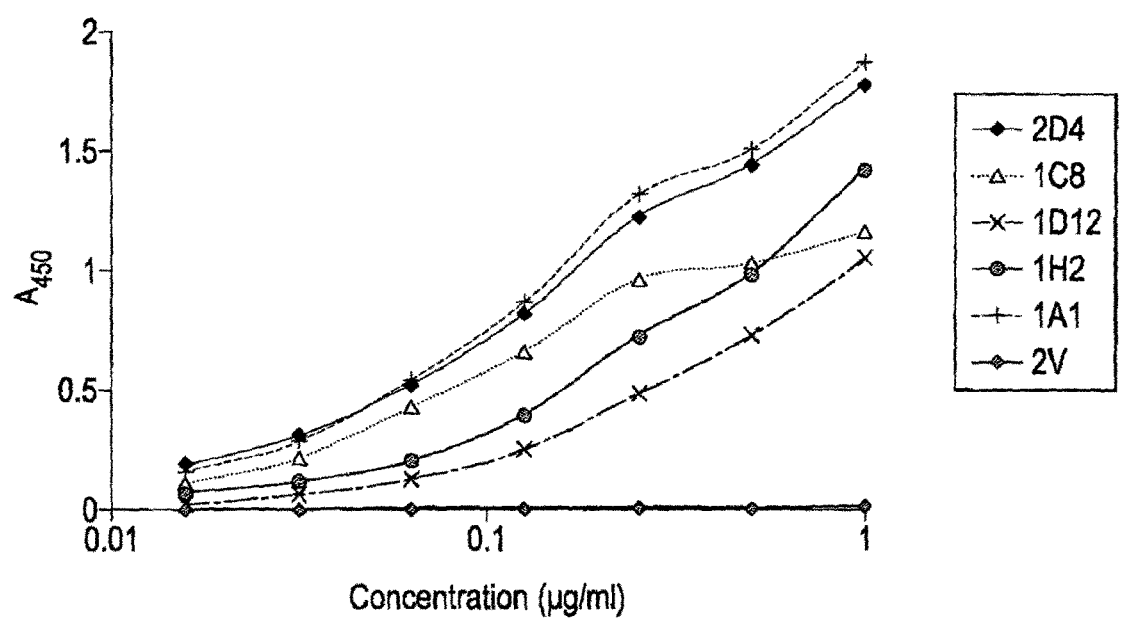

Positive binding and neutralizing unique domains were converted into Fc format for further analyses as follows: Selected positive monomeric VNAR domains were PCR amplified with primers introducing restriction sites and flanking sequences compatible for cloning into a proprietary Fc mammalian expression vector which facilitated Protein A affinity purification of expressed proteins post PEI-mediated transient expression in HEK 293 suspension culture. Expression levels of VNAR Fc fusion proteins were generally in the region of 50-70 mg per liter using serum free media. Essentially, post expression cell debris was removed from conditioned media by centrifugation and 0.2 µm filtration, then following affinity chromatography as detailed above proteins were subjected to a final polishing step by passage over a Superdex 200 26/60 size-exclusion column equilibrated with PBS. Eluted peaks from SEC were concentrated using Amicon ultra filtration units and protein concentrations determined by UV spectroscopy. Purified Fc proteins were then assessed for binding cell surface expressed hICOSL as illustrated in FIG. 3.

Figure 4:
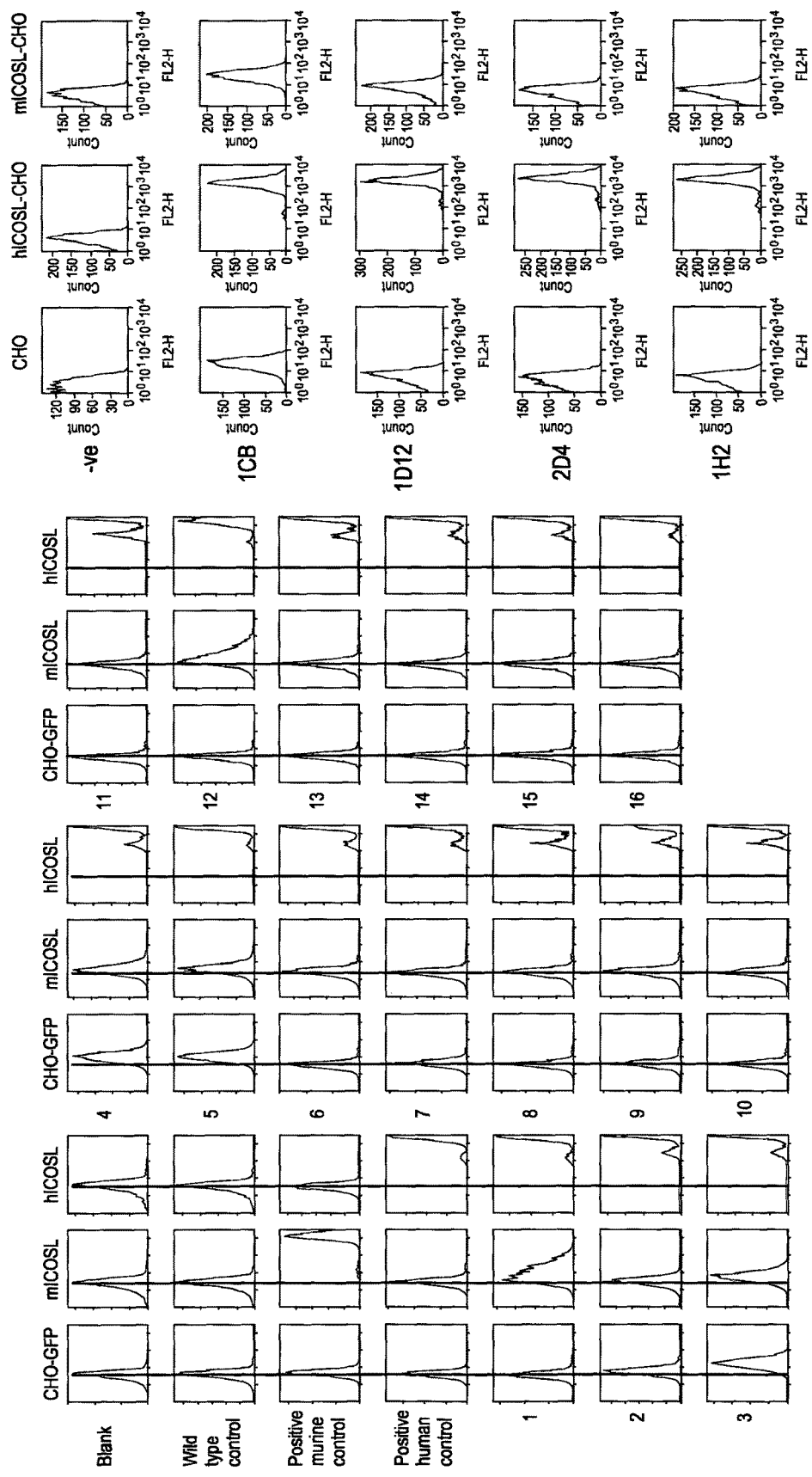

Selectivity of anti-hICOSL VNAR domains were assessed using FACS assays that were carried out as follows: parental, mICOSL and hICOSL ligand expressing CHO cells were washed in PBS and removed from flasks by the addition of PBS and 5% EDTA at 37° C. for 10-15 min. Cells were monodispersed by pipetting up and down against the surface of the flask, spun down at 1200 rpm and re-suspended in DMEM plus 5% FCS. Cells are aliquoted at a density of 0.5-1×10⁶ cells/well into a 96-well U-bottomed plate. Cells are incubated with 100 µl tissue culture supernatant containing HEK293 VNAR-hFc expressed proteins for 30 minutes at 16° C. followed by 3× washes with PBS plus 2% FCS. Cells were then incubated with 100 μl anti-hFc-biotin (eBioscience) at 1 μg/ml for 30 minutes at 16° C. After 3× washes with PBS plus 2% FCS, streptavidin-APC (eBioscience) was added at 1 μg/ml for 30 minutes at 16° C. After 1× wash with PBS plus 2% FCS, cells were resuspended in 400 μl PBS plus 2% FCS and transferred into FACS tubes for analyses on a FACS-Canto-2. FIG. 4a shows the FACS analysis of the synthetically-library derived anti-hICOSL VNAR domains and FIG. 4b shows the immunized-library derived domains. The together the data shows clear binding to the human ICOSL expressing CHO cells illustrated by a shift in readout to the left.

Figure 5:
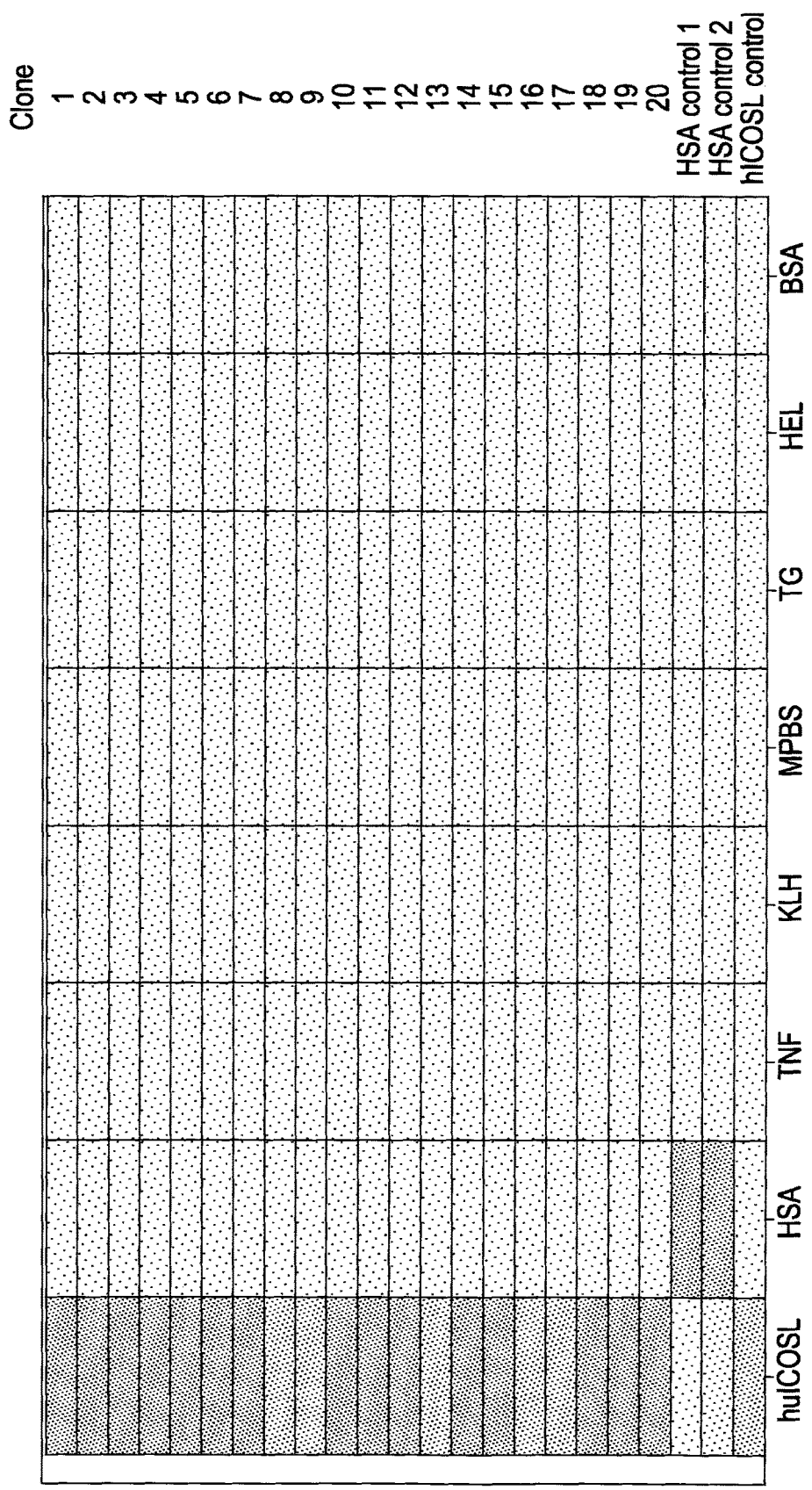

Selectivity of the synthetically-library derived anti-hICOSL VNAR domains was also clearly shown by binding ELISA against multiple unrelated proteins as exemplified in FIG. 5. Binding of all positive anti-hICOSL clones is visualized by dark shading on the left. No binding against the other included targets; human serum albumin (HSA), tumour necrosis factor-α (TNF-α), keyhole limpet hemocyanin (KLH), milk phosphate-buffered saline (MPBS), thyroglobulin (TG), hen-egg lysozyme (HEL) or bovine serum albumin (BSA) is detectable. Positive controls against HSA were included and can clearly be seen as dark regions representing positive binding.

Affinity measurements of hits were conducted on both monomeric and Fc formatted positive leads (FIG. 6): All BIAcore analysis was performed using the T-100 biosensor, series S CM5 chips, an amine-coupling kit, 10 mM Sodium acetate immobilization buffers at pH 4, 4.5, 5.0, and 5.5, 10× HBS-P running buffer and 50 mM NaOH (GE Healthcare). Assay conditions were established to minimize the influence of mass transfer, avidity and rebinding events. Targeted ligand immobilization programs were set to immobilize approximately 1000 response units (RU) of purified hICOSL-Fc (R & D Systems) and hICOSL monomer on flow cells (Fc) 2 & 3 respectively at pH 4. The purified VNAR proteins were diluted in HBS-P running buffer to a range of final concentrations (2-fold dilutions starting from 600-37.5 nM for calculation of kinetic constants using global fit analysis). Each concentration was injected for 3 minutes at a fast flow rate of 30 ml/minute and allowed to dissociate for 5 min, followed by a 5 sec regeneration pulse with 50 mM NaOH. Reference subtracted sensorgrams for each concentration were analyzed using BIAcore T100 evaluation software (1.1.1).

EXAMPLE 5: IN VITRO FUNCTIONAL VALIDATION OF HITS AGAINST HICOSL

In vitro efficacy of anti-hICOSL-Fc hits were measured by two cell based assays. The first was a ligand-receptor neutralization assay as described in Example 1. Purified anti-hICOSL-Fc VNAR domains from both synthetic and immunized libraries were titrated into neutralization assays demonstrating the ability to specifically block the ICOSL-ICOS interaction (FIGS. 7A and B). The second cell based functional assays conducted were T-cell proliferation assays using primary human T-cells isolated from normal healthy donors. The method, in brief, is as follows: for the primary plate coating add 1 μg/ml anti-huCD3 clone OKT3 (eBioscience cat. #16-5889aCD3) plus 10 μg/ml anti-hIgG (Jackson ImmunoResearch cat. #109-006-098) in PBS in a total of 100 μl/well. Leave overnight at 4° C. and then remove solution from wells and wash wells 2× with PBS. For the secondary coating add 4 μg/ml hB7-2.Ig (R&D Systems cat. #141-B2-100) plus 500 ng/ml hICOSL.Ig (R&D Systems cat.#165-B7-100) in PBS 100 μl/well. Leave for 3 hours at room temperature and then wash 2× with PBS. Add 50 μl media in all wells of assay plate. CD4+ T cells were diluted to give $2 \times 10^6$ cells/ail and test antibodies diluted to 3× the desired final concentration. To the 50 μl media in each well, 50 μl antibody solution and 50 μl cell suspension was added to give a final volume of 150 μl/well with a final concentration of $1 \times 10^5$ cells/well. The samples were left for 3 days and then pulsed with 1 μCi/well of $^3$H thymidine for 6-8 hours on day 3 and counts measured. FIG. 8 shows the calculated potency (IC50 values) of the anti-hICOSL VNAR domains from the synthetic library using T-cells isolated from two independent donors.

EXAMPLE 5: RE-FORMATTING ANTI-ICOSL VNAR DOMAINS AS MOLECULAR FUSION PROTEINS

The isolated anti-ICOSL domains from the synthetic library, ELSS1, can be cloned in tandem to form a trimer fusion product linked with (GGGS)$_4$ (SEQ ID NO: 170) amino acid stretches, be expressed, purified and demonstrate binding to all three individual targets by ELISA. FIG. 11 exemplifies two different orientations of trimer construct using the anti-murine ICOSL VNAR domain CC3 (prepared according to the method described in co-pending international patent application no. PCT/EP2014/058251 filed 23 Apr. 2014 claiming priority from U.S. 61/815,043 filed 23 Apr. 2013 (incorporated by reference), fused to both the anti-human ICOSL VNAR domain, 2D4, and the anti-HSA specific VNAR domain, E06 (prepared as described in WO 2013/167883). All three VNAR domains retain the ability to bind target when linked as a single molecular fusion protein.

The invention claimed is:

1. An ICOSL specific antigen binding molecule comprising an amino acid sequence represented by the formula (I)

A-X-B-Y-C     (I);

wherein:
A is SEQ ID NO: 1, SEQ ID NO: 4 or SEQ ID NO: 7, or a sequence at least 87% identical to SEQ ID NO: 1, SEQ ID NO: 4 or SEQ ID NO: 7,
X is a CDR1 region of SEQ ID NO: 95,
B is SEQ ID NO: 2, SEQ ID NO: 5 or SEQ ID NO: 8, or a sequence at least 87% identical to SEQ ID NO: 2, SEQ ID NO: 5 or SEQ ID NO: 8,
Y is a CDR3 region of SEQ ID NO: 122, and
C is SEQ ID NO: 3, SEQ ID NO: 6, or SEQ ID NO: 9, or a sequence at least 87% identical to SEQ ID NO: 3, SEQ ID NO: 6, or SEQ ID NO: 9,
in which:

SEQ ID NO: 1 is
TRVDQTPRTATKETGESLTINCVLTDT,
TRVDQTPRTATKETGESLTINCWTGA

SEQ ID NO: 2 is
TSWFRKNPGTTDWERMSIGGRYVESVNKGAKSFSLRIKDLTVADSATYYCKA
or

TSWFRKNPGTTDWERMSIGGRYVESVNKGAKSFSLRIKDLTVADSATYICRA

SEQ ID NO: 3 is
DGAGTVLTVN

SEQ ID NO: 4 is
ASVNQTPRTATKETGESLTINCVLTDT

SEQ ID NO: 5 is
TYWYRKNPGSSNQERISISGRYVESVNKRTMSFSLRIKDLTVADSATYYCKA
or

TYWYRKNPGSSNQERISISGRYVESVNKRTMSFSLRIKDLTVADSATYICRA

SEQ ID NO: 6 is
YGAGTVLTVN

SEQ ID NO: 7 is
ARVDQTPRSVTKETGESLTINCVLRDP or

ARVDQTPRSVTKETGESLTINCVLRDA or

ARVDQTPRSVTKETGESLTINCVLRDG or

ARVDQTPRSVTKETGESLTINCVLRES

SEQ ID NO: 8 is
TCWYRKKSGSTNEESISKGGRYVETVNSGSKSFSLRINDLTVEDGGTYRCGA
or

TCWSRKKSGSTNEESISKGGRYVETVNSGSKSFSLRINDLTVEDGGTYRCGL,

TCWTRKKSGSTNEESISKGGRYVETVNSGSKSFSLRINDLTVEDGGTYRCAL,

TCWYRKKSGSTNEESISKGGRYVETVNSGSKSFSLRINDLTVEDGGTYRCGV,

TCWYRKKSGSTNEESISKGGRYVETVNSGSKSFSLRINDLTVEDGGTYRCGH,

TCWYRKKSGSTNEESISKGGRYVETVNSGSKSFSLRISDLTVEDGGTYRCGH,

SEQ ID NO: 9 is
CGGGTVVTVN, CGGGTAVTVN, CGDGTAVTVN,
or

CGDGTAVTVN,

SEQ ID NO: 95 is DYGLFS, and
SEQ ID NO: 122 is FTWPWEWPDRWFRPWY.

2. The ICOSL specific antigen binding molecule as claimed in claim 1 which is humanized.

3. A fusion protein comprising the ICOSL specific antigen binding molecule as claimed in claim 1.

4. The fusion protein as claimed in claim 3, in which the ICOSL specific antigen binding molecule is fused to a biologically active protein.

5. A pharmaceutical composition comprising the ICOSL specific antigen binding molecule as defined in claim 1.

6. The ICOSL specific antigen binding molecule of claim 1, wherein the ICOSL specific antigen binding molecule comprises the amino acid sequence of SEQ ID NO: 21.

* * * * *

UNITED STATES PATENT AND TRADEMARK OFFICE
CERTIFICATE OF CORRECTION

PATENT NO. : 10,472,410 B2
APPLICATION NO. : 14/785975
DATED : November 12, 2019
INVENTOR(S) : Caroline Jane Barelle et al.

Page 1 of 1

It is certified that error appears in the above-identified patent and that said Letters Patent is hereby corrected as shown below:

In the Claims

Column 135, Line 44 delete "TRVDQTPRTATKETGESLTINCWTGA" and insert --"TRVDQTPRTATKETGESLTINCVVTGA--

Signed and Sealed this
Ninth Day of June, 2020

Andrei Iancu
*Director of the United States Patent and Trademark Office*